US012594062B2

(12) United States Patent
Watson et al.

(10) Patent No.: US 12,594,062 B2
(45) Date of Patent: Apr. 7, 2026

(54) FLUID COLLECTION ASSEMBLIES INCLUDING AN EXTENSION

(71) Applicant: PureWick Corporation, El Cajon, CA (US)

(72) Inventors: Kristin Louise Watson, Social Circle, GA (US); Matthew Jordan Rothberg, Atlanta, GA (US); Patrick Hudson Chancy, Dunwoody, GA (US)

(73) Assignee: PUREWICK CORPORATION, Covington, GA (US)

(*) Notice: Subject to any disclaimer, the term of this patent is extended or adjusted under 35 U.S.C. 154(b) by 710 days.

(21) Appl. No.: 17/930,238

(22) Filed: Sep. 7, 2022

(65) Prior Publication Data

US 2023/0070347 A1 Mar. 9, 2023

Related U.S. Application Data

(60) Provisional application No. 63/241,562, filed on Sep. 8, 2021.

(51) Int. Cl.
| | |
|---|---|
| *A61B 10/00* | (2006.01) |
| *A61F 5/44* | (2006.01) |
| *A61F 5/451* | (2006.01) |

(52) U.S. Cl.
CPC .......... *A61B 10/007* (2013.01); *A61F 5/4404* (2013.01); *A61F 5/451* (2013.01)

(58) Field of Classification Search
CPC ..... A61B 10/0045; A61F 5/4404; A61F 5/451
See application file for complete search history.

(56) References Cited

U.S. PATENT DOCUMENTS

| | | | |
|---|---|---|---|
| 670,602 | A | 3/1901 | Baker |
| 737,443 | A | 8/1903 | Mooers |
| 1,015,905 | A | 1/1912 | Northrop |
| 1,032,841 | A | 7/1912 | Koenig |

(Continued)

FOREIGN PATENT DOCUMENTS

| | | |
|---|---|---|
| AU | 2018216821 A1 | 8/2019 |
| AU | 2021299304 A1 | 2/2023 |

(Continued)

OTHER PUBLICATIONS

US 9,908,683 B2, 03/2018, Sandhausen et al. (withdrawn)

(Continued)

*Primary Examiner* — Daniel L Cerioni
(74) *Attorney, Agent, or Firm* — Ballard Spahr LLP

(57) ABSTRACT

An example fluid collection assembly includes a fluid impermeable layer. The fluid impermeable layer includes a proximal end region and a distal end region. The fluid impermeable layer also defines at least a chamber, at least one opening that may be between the proximal and distal end regions, and a fluid outlet that may be at the proximal end region. The fluid collection assembly may also include at least one porous material disposed in the chamber. The fluid collection assembly further includes an extension that is at least one of attachable or extends from the distal end region of the fluid impermeable layer. The extension is configured to be disposed within the gluteal cleft (e.g., between the buttocks) to help secure the fluid collection assembly to an individual using the fluid collection assembly.

20 Claims, 6 Drawing Sheets

(56) References Cited

U.S. PATENT DOCUMENTS

| | | | |
|---|---|---|---|
| 1,178,644 A | 4/1916 | Johnson |
| 1,387,726 A | 8/1921 | Karge |
| 1,742,080 A | 12/1929 | Jones |
| 1,979,899 A | 11/1934 | Obrien et al. |
| 2,241,010 A | 5/1941 | Chipley |
| 2,262,772 A | 11/1941 | Peder |
| 2,326,881 A | 8/1943 | Packer |
| 2,379,346 A | 6/1945 | Farrell |
| 2,485,555 A | 10/1949 | Bester |
| 2,571,357 A | 10/1951 | Charles |
| 2,613,670 A | 10/1952 | Edward |
| 2,616,426 A | 11/1952 | Adele |
| 2,644,234 A | 7/1953 | Earl |
| 2,648,335 A | 8/1953 | Chambers |
| 2,859,786 A | 11/1958 | Tupper |
| 2,944,551 A | 7/1960 | Carl |
| 2,968,046 A | 1/1961 | Duke |
| 2,971,512 A | 2/1961 | Reinhardt |
| 3,032,038 A | 5/1962 | Swinn |
| 3,077,883 A | 2/1963 | Hill |
| 3,087,938 A | 4/1963 | Hans et al. |
| 3,114,916 A | 12/1963 | Hadley |
| 3,169,528 A | 2/1965 | Knox et al. |
| 3,171,506 A | 3/1965 | Therkel |
| 3,175,719 A | 3/1965 | Herndon |
| 3,194,238 A | 7/1965 | Breece |
| 3,198,994 A | 8/1965 | Hildebrandt et al. |
| 3,221,742 A | 12/1965 | Egon |
| 3,312,221 A | 4/1967 | Overment |
| 3,312,981 A | 4/1967 | Mcguire et al. |
| 3,349,768 A | 10/1967 | Keane |
| 3,362,590 A | 1/1968 | Gene |
| 3,366,116 A | 1/1968 | Huck |
| 3,398,848 A | 8/1968 | Donovan |
| 3,400,717 A | 9/1968 | Bruce et al. |
| 3,406,688 A | 10/1968 | Bruce |
| 3,424,163 A | 1/1969 | Gravdahl |
| 3,425,471 A | 2/1969 | Yates |
| 3,434,565 A | 3/1969 | Fischer |
| 3,511,241 A | 5/1970 | Lee |
| 3,512,185 A | 5/1970 | Ellis |
| 3,520,300 A | 7/1970 | Flower |
| 3,528,423 A | 9/1970 | Lee |
| 3,608,552 A | 9/1971 | Broerman |
| 3,613,123 A | 10/1971 | Langstrom |
| 3,648,700 A | 3/1972 | Warner |
| 3,651,810 A | 3/1972 | Ormerod |
| 3,661,155 A | 5/1972 | Lindan |
| 3,683,918 A | 8/1972 | Pizzella |
| 3,699,815 A | 10/1972 | Holbrook |
| 3,726,277 A | 4/1973 | Hirschman |
| 3,742,952 A | 7/1973 | Magers et al. |
| 3,757,355 A | 9/1973 | Allen et al. |
| 3,788,324 A | 1/1974 | Lim |
| 3,843,016 A | 10/1974 | Bornhorst et al. |
| 3,863,638 A | 2/1975 | Rogers et al. |
| 3,863,798 A | 2/1975 | Kurihara et al. |
| 3,864,759 A | 2/1975 | Horiuchi |
| 3,865,109 A | 2/1975 | Elmore et al. |
| 3,881,486 A | 5/1975 | Fenton |
| 3,881,489 A | 5/1975 | Hartwell |
| 3,915,189 A | 10/1975 | Holbrook et al. |
| 3,931,650 A | 1/1976 | Miller |
| 3,998,228 A | 12/1976 | Poidomani |
| 3,999,550 A | 12/1976 | Martin |
| 4,006,793 A | 2/1977 | Robinson |
| 4,015,604 A | 4/1977 | Csillag |
| 4,020,843 A | 5/1977 | Kanall |
| 4,022,213 A | 5/1977 | Stein |
| 4,027,776 A | 6/1977 | Douglas |
| 4,031,897 A | 6/1977 | Graetz |
| 4,064,962 A | 12/1977 | Hunt |
| 4,069,817 A | 1/1978 | Fenole et al. |
| 4,084,589 A | 4/1978 | Kulvi |
| 4,096,897 A | 6/1978 | Cammarata |
| 4,116,197 A | 9/1978 | Bermingham |
| 4,180,178 A | 12/1979 | Turner |
| 4,187,953 A | 2/1980 | Turner |
| 4,194,508 A | 3/1980 | Anderson |
| 4,200,102 A | 4/1980 | Duhamel et al. |
| 4,202,058 A | 5/1980 | Anderson |
| 4,203,503 A | 5/1980 | Bertotti et al. |
| 4,209,076 A | 6/1980 | Bertotti et al. |
| 4,223,677 A | 9/1980 | Anderson |
| 4,233,025 A | 11/1980 | Larson et al. |
| 4,233,978 A | 11/1980 | Hickey |
| 4,246,901 A | 1/1981 | Frosch et al. |
| 4,253,542 A | 3/1981 | Ruspa et al. |
| 4,257,418 A | 3/1981 | Hessner |
| 4,270,539 A | 6/1981 | Frosch et al. |
| 4,280,498 A | 7/1981 | Jensen |
| 4,281,655 A | 8/1981 | Terauchi |
| 4,292,916 A | 10/1981 | Bradley et al. |
| 4,330,239 A | 5/1982 | Gannaway |
| 4,345,341 A | 8/1982 | Saito |
| 4,349,029 A | 9/1982 | Mott |
| 4,352,356 A | 10/1982 | Tong |
| 4,360,933 A | 11/1982 | Kimura et al. |
| 4,365,363 A | 12/1982 | Windauer |
| 4,375,841 A | 3/1983 | Vielbig |
| 4,387,726 A | 6/1983 | Denard |
| 4,403,991 A | 9/1983 | Hill |
| 4,421,511 A | 12/1983 | Steer et al. |
| 4,425,130 A | 1/1984 | Desmarais |
| 4,446,986 A | 5/1984 | Bowen et al. |
| 4,453,938 A | 6/1984 | Brendling |
| 4,457,314 A | 7/1984 | Knowles |
| 4,476,879 A | 10/1984 | Jackson |
| 4,526,688 A | 7/1985 | Schmidt et al. |
| 4,528,703 A | 7/1985 | Kraus |
| 4,533,354 A | 8/1985 | Jensen et al. |
| 4,533,357 A | 8/1985 | Hall |
| D280,438 S | 9/1985 | Wendt |
| 4,551,141 A | 11/1985 | Mcneil |
| 4,553,968 A | 11/1985 | Komis |
| 4,568,341 A | 2/1986 | Mitchell et al. |
| 4,581,026 A | 4/1986 | Schneider |
| 4,583,983 A | 4/1986 | Einhorn et al. |
| 4,589,516 A | 5/1986 | Inoue et al. |
| 4,601,716 A | 7/1986 | Smith |
| 4,610,675 A | 9/1986 | Triunfol |
| 4,620,333 A | 11/1986 | Ritter |
| 4,626,250 A | 12/1986 | Schneider |
| 4,627,846 A | 12/1986 | Ternstroem |
| 4,631,061 A | 12/1986 | Martin |
| 4,650,477 A | 3/1987 | Johnson |
| 4,655,754 A | 4/1987 | Richmond et al. |
| 4,656,675 A | 4/1987 | Fajnsztajn |
| 4,681,570 A | 7/1987 | Dalton |
| 4,681,572 A | 7/1987 | Tokarz et al. |
| 4,681,577 A | 7/1987 | Stern et al. |
| 4,692,160 A | 9/1987 | Nussbaumer |
| 4,707,864 A | 11/1987 | Ikematsu et al. |
| 4,713,065 A | 12/1987 | Koot |
| 4,713,066 A | 12/1987 | Komis |
| 4,723,953 A | 2/1988 | Pratt et al. |
| 4,735,841 A | 4/1988 | Sourdet |
| 4,743,236 A | 5/1988 | Manschot |
| 4,747,166 A | 5/1988 | Kuntz |
| 4,752,944 A | 6/1988 | Conrads et al. |
| 4,769,215 A | 9/1988 | Ehrenkranz |
| 4,771,484 A | 9/1988 | Mozell |
| 4,772,280 A | 9/1988 | Rooyakkers |
| 4,784,654 A | 11/1988 | Beecher |
| 4,790,830 A | 12/1988 | Hamacher |
| 4,790,835 A | 12/1988 | Elias |
| 4,791,686 A | 12/1988 | Taniguchi et al. |
| 4,795,449 A | 1/1989 | Schneider et al. |
| 4,798,603 A | 1/1989 | Meyer et al. |
| 4,799,928 A | 1/1989 | Crowley |
| 4,804,377 A | 2/1989 | Hanifl et al. |
| 4,812,053 A | 3/1989 | Bhattacharjee |
| 4,813,943 A | 3/1989 | Smith |
| 4,820,291 A | 4/1989 | Terauchi et al. |

(56) References Cited

U.S. PATENT DOCUMENTS

| | | | |
|---|---|---|---|
| 4,820,297 A | 4/1989 | Kaufman et al. | |
| 4,841,728 A | 6/1989 | Jean et al. | |
| 4,846,818 A | 7/1989 | Keldahl et al. | |
| 4,846,819 A | 7/1989 | Welch | |
| 4,846,824 A | 7/1989 | Schultz et al. | |
| 4,846,909 A | 7/1989 | Klug et al. | |
| 4,865,595 A | 9/1989 | Heyden | |
| 4,880,417 A | 11/1989 | Yabrov et al. | |
| 4,882,794 A | 11/1989 | Stewart | |
| 4,883,465 A | 11/1989 | Brennan | |
| 4,886,498 A | 12/1989 | Newton | |
| 4,886,508 A | 12/1989 | Washington | |
| 4,886,509 A | 12/1989 | Mattsson | |
| 4,889,532 A | 12/1989 | Metz et al. | |
| 4,889,533 A | 12/1989 | Beecher | |
| 4,890,691 A | 1/1990 | Ching-Ho | |
| 4,895,140 A | 1/1990 | Bellak | |
| 4,903,254 A | 2/1990 | Haas | |
| 4,904,248 A | 2/1990 | Vaillancourt | |
| 4,905,692 A | 3/1990 | More | |
| 4,911,262 A | 3/1990 | Tani et al. | |
| 4,930,997 A | 6/1990 | Bennett | |
| 4,936,838 A | 6/1990 | Cross et al. | |
| 4,950,262 A | 8/1990 | Takagi | |
| 4,955,922 A | 9/1990 | Terauchi | |
| 4,957,487 A | 9/1990 | Gerow | |
| 4,965,460 A | 10/1990 | Tanaka et al. | |
| 4,986,823 A | 1/1991 | Anderson et al. | |
| 4,987,849 A | 1/1991 | Sherman | |
| 5,002,541 A | 3/1991 | Conkling et al. | |
| 5,004,463 A | 4/1991 | Nigay | |
| 5,013,308 A | 5/1991 | Sullivan et al. | |
| 5,031,248 A | 7/1991 | Kemper | |
| 5,045,077 A | 9/1991 | Blake | |
| 5,045,283 A | 9/1991 | Patel | |
| 5,049,144 A | 9/1991 | Payton | |
| 5,053,339 A | 10/1991 | Patel | |
| 5,057,092 A | 10/1991 | Webster | |
| 5,058,088 A | 10/1991 | Haas et al. | |
| 5,071,347 A | 12/1991 | McGuire | |
| 5,078,707 A | 1/1992 | Peter | |
| 5,084,037 A | 1/1992 | Barnett | |
| 5,100,396 A | 3/1992 | Zamierowski | |
| 5,102,404 A | 4/1992 | Goldberg et al. | |
| 5,112,324 A | 5/1992 | Wallace | |
| 5,137,033 A | 8/1992 | Norton | |
| 5,147,301 A | 9/1992 | Ruvio | |
| 5,176,667 A | 1/1993 | Debring | |
| 5,195,997 A | 3/1993 | Carns | |
| 5,196,654 A | 3/1993 | Diflora et al. | |
| 5,199,444 A | 4/1993 | Wheeler | |
| 5,203,699 A | 4/1993 | McGuire | |
| 5,244,458 A | 9/1993 | Takasu | |
| 5,246,454 A | 9/1993 | Peterson | |
| 5,267,988 A | 12/1993 | Farkas | |
| 5,275,307 A | 1/1994 | Freese | |
| 5,282,795 A | 2/1994 | Finney | |
| 5,294,983 A | 3/1994 | Ersoz et al. | |
| 5,295,979 A | 3/1994 | Delaurentis et al. | |
| 5,295,983 A | 3/1994 | Kubo | |
| 5,300,052 A | 4/1994 | Kubo | |
| 5,304,749 A | 4/1994 | Crandell | |
| 5,312,383 A | 5/1994 | Kubalak | |
| 5,318,550 A | 6/1994 | Cermak et al. | |
| 5,330,457 A | 7/1994 | Cohen | |
| 5,330,459 A | 7/1994 | Lavon et al. | |
| 5,334,174 A | 8/1994 | Street | |
| 5,340,840 A | 8/1994 | Park et al. | |
| 5,382,244 A | 1/1995 | Telang | |
| 5,397,315 A | 3/1995 | Schmidt et al. | |
| 5,409,014 A | 4/1995 | Napoli et al. | |
| 5,409,475 A | 4/1995 | Steer | |
| 5,411,495 A | 5/1995 | Willingham | |
| 5,423,784 A | 6/1995 | Metz | |
| 5,423,788 A | 6/1995 | Rollins et al. | |
| 5,437,836 A | 8/1995 | Yamada | |
| 5,456,246 A | 10/1995 | Schmieding et al. | |
| 5,466,229 A | 11/1995 | Elson et al. | |
| 5,478,334 A | 12/1995 | Bernstein | |
| 5,499,977 A | 3/1996 | Marx | |
| 5,543,042 A | 8/1996 | Filan et al. | |
| D373,928 S | 9/1996 | Green | |
| 5,582,604 A | 12/1996 | Ahr et al. | |
| 5,592,950 A | 1/1997 | Kopelowicz | |
| 5,593,389 A | 1/1997 | Chang | |
| 5,605,161 A | 2/1997 | Cross | |
| 5,614,699 A | 3/1997 | Yashiro et al. | |
| 5,618,277 A | 4/1997 | Goulter | |
| 5,628,735 A | 5/1997 | Skow | |
| 5,632,736 A | 5/1997 | Block | |
| 5,636,643 A | 6/1997 | Argenta et al. | |
| 5,637,104 A | 6/1997 | Ball et al. | |
| 5,662,633 A | 9/1997 | Doak et al. | |
| 5,674,212 A | 10/1997 | Osborn et al. | |
| 5,678,564 A | 10/1997 | Lawrence et al. | |
| 5,678,654 A | 10/1997 | Uzawa | |
| 5,681,297 A | 10/1997 | Hashimoto et al. | |
| 5,687,429 A | 11/1997 | Rahlff | |
| 5,695,485 A | 12/1997 | Duperret et al. | |
| 5,700,254 A | 12/1997 | Mcdowall et al. | |
| 5,701,612 A | 12/1997 | Daneshvar | |
| 5,705,777 A | 1/1998 | Flanigan et al. | |
| 5,735,835 A | 4/1998 | Holland | |
| 5,752,944 A | 5/1998 | Dann et al. | |
| 5,763,333 A | 6/1998 | Suzuki et al. | |
| 5,772,644 A | 6/1998 | Bark et al. | |
| 5,792,132 A | 8/1998 | Garcia | |
| 5,827,243 A | 10/1998 | Palestrant | |
| 5,827,247 A | 10/1998 | Kay | |
| 5,827,250 A | 10/1998 | Fujioka et al. | |
| 5,827,257 A | 10/1998 | Fujioka et al. | |
| D401,699 S | 11/1998 | Herchenbach et al. | |
| 5,859,393 A | 1/1999 | Cummins et al. | |
| 5,865,378 A | 2/1999 | Hollinshead et al. | |
| 5,873,869 A | 2/1999 | Hammons et al. | |
| 5,876,393 A | 3/1999 | Ahr et al. | |
| 5,887,291 A | 3/1999 | Bellizzi | |
| 5,891,125 A | 4/1999 | Plumley | |
| 5,894,608 A | 4/1999 | Birbara | |
| 5,895,349 A | 4/1999 | Tihon | |
| D409,303 S | 5/1999 | Oepping | |
| 5,911,222 A | 6/1999 | Lawrence et al. | |
| 5,956,782 A | 9/1999 | Olguin | |
| 5,957,904 A | 9/1999 | Holland | |
| 5,968,026 A | 10/1999 | Osborn et al. | |
| 5,972,505 A | 10/1999 | Phillips et al. | |
| 6,007,526 A | 12/1999 | Passalaqua et al. | |
| 6,039,060 A | 3/2000 | Rower | |
| 6,050,983 A | 4/2000 | Moore et al. | |
| 6,059,762 A | 5/2000 | Boyer et al. | |
| 6,063,064 A | 5/2000 | Tuckey et al. | |
| 6,098,625 A | 8/2000 | Winkler | |
| 6,105,174 A | 8/2000 | Karlsten et al. | |
| 6,113,582 A | 9/2000 | Dwork | |
| 6,117,163 A | 9/2000 | Bierman | |
| 6,123,398 A | 9/2000 | Arai et al. | |
| 6,129,718 A | 10/2000 | Wada et al. | |
| 6,131,964 A | 10/2000 | Sareshwala | |
| 6,152,902 A | 11/2000 | Christian et al. | |
| 6,164,569 A | 12/2000 | Hollinshead et al. | |
| 6,177,606 B1 | 1/2001 | Etheredge et al. | |
| 6,209,142 B1 | 4/2001 | Mattsson et al. | |
| 6,220,050 B1 | 4/2001 | Cooksey | |
| 6,244,311 B1 | 6/2001 | Hand et al. | |
| 6,248,096 B1 | 6/2001 | Dwork et al. | |
| 6,263,887 B1 | 7/2001 | Dunn | |
| 6,283,246 B1 | 9/2001 | Nishikawa | |
| 6,296,627 B1 | 10/2001 | Edwards | |
| 6,311,339 B1 | 11/2001 | Kraus | |
| 6,316,688 B1 | 11/2001 | Hammons et al. | |
| 6,336,919 B1 | 1/2002 | Davis et al. | |
| 6,338,729 B1 | 1/2002 | Wada et al. | |
| 6,352,525 B1 | 3/2002 | Wakabayashi | |
| 6,394,988 B1 | 5/2002 | Hashimoto | |

(56)             References Cited

U.S. PATENT DOCUMENTS

| 6,395,956 | B1 | 5/2002 | Glasgow et al. |
| 6,398,742 | B1 | 6/2002 | Kim |
| 6,406,463 | B1 | 6/2002 | Brown |
| 6,409,712 | B1 | 6/2002 | Dutari et al. |
| 6,415,888 | B2 | 7/2002 | An et al. |
| 6,416,500 | B1 | 7/2002 | Wada et al. |
| 6,423,045 | B1 | 7/2002 | Wise et al. |
| 6,428,521 | B1 | 8/2002 | Droll |
| 6,428,522 | B1 | 8/2002 | Dipalma et al. |
| 6,446,454 | B1 | 9/2002 | Lee et al. |
| 6,461,340 | B1 | 10/2002 | Lenker et al. |
| 6,467,570 | B1 | 10/2002 | Herold |
| 6,475,198 | B1 | 11/2002 | Lipman et al. |
| 6,479,726 | B1 | 11/2002 | Cole et al. |
| 6,491,673 | B1 | 12/2002 | Palumbo et al. |
| 6,508,794 | B1 | 1/2003 | Palumbo et al. |
| 6,524,292 | B1 | 2/2003 | Dipalma et al. |
| 6,540,729 | B1 | 4/2003 | Wada et al. |
| 6,547,771 | B2 | 4/2003 | Robertson et al. |
| 6,551,293 | B1 | 4/2003 | Mitchell |
| 6,569,133 | B2 | 5/2003 | Cheng et al. |
| D476,518 | S | 7/2003 | Doppelt |
| 6,592,560 | B2 | 7/2003 | Snyder et al. |
| 6,610,038 | B1 | 8/2003 | Dipalma et al. |
| 6,618,868 | B2 | 9/2003 | Minnick |
| 6,620,142 | B1 | 9/2003 | Flueckiger |
| 6,629,651 | B1 | 10/2003 | Male et al. |
| 6,635,037 | B1 | 10/2003 | Bennett |
| 6,635,038 | B2 | 10/2003 | Scovel |
| 6,652,495 | B1 | 11/2003 | Walker |
| 6,666,850 | B1 | 12/2003 | Ahr et al. |
| 6,685,684 | B1 | 2/2004 | Falconer |
| 6,695,828 | B1 | 2/2004 | Dipalma et al. |
| 6,699,174 | B1 | 3/2004 | Bennett |
| 6,700,034 | B1 | 3/2004 | Lindsay et al. |
| 6,702,793 | B1 | 3/2004 | Sweetser et al. |
| 6,706,027 | B2 | 3/2004 | Harvie et al. |
| 6,732,384 | B2 | 5/2004 | Scott |
| 6,736,977 | B1 | 5/2004 | Hall et al. |
| 6,740,066 | B2 | 5/2004 | Wolff et al. |
| 6,764,477 | B1 | 7/2004 | Chen et al. |
| 6,783,519 | B2 | 8/2004 | Samuelsson |
| 6,796,974 | B2 | 9/2004 | Palumbo et al. |
| 6,814,547 | B2 | 11/2004 | Childers et al. |
| 6,849,065 | B2 | 2/2005 | Schmidt et al. |
| 6,857,137 | B2 | 2/2005 | Otto |
| 6,885,690 | B2 | 4/2005 | Aggerstam et al. |
| 6,888,044 | B2 | 5/2005 | Fell et al. |
| 6,893,425 | B2 | 5/2005 | Dunn et al. |
| 6,912,737 | B2 | 7/2005 | Ernest et al. |
| 6,918,899 | B2 | 7/2005 | Harvie |
| 6,979,324 | B2 | 12/2005 | Bybordi et al. |
| 7,018,366 | B2 | 3/2006 | Easter |
| 7,066,411 | B2 | 6/2006 | Male et al. |
| 7,122,023 | B1 | 10/2006 | Hinoki |
| 7,125,399 | B2 | 10/2006 | Miskie |
| 7,131,964 | B2 | 11/2006 | Harvie |
| 7,135,012 | B2 | 11/2006 | Harvie |
| 7,141,043 | B2 | 11/2006 | Harvie |
| D533,972 | S | 12/2006 | La |
| 7,160,273 | B2 | 1/2007 | Greter et al. |
| 7,166,092 | B2 | 1/2007 | Elson et al. |
| 7,171,699 | B2 | 2/2007 | Ernest et al. |
| 7,171,871 | B2 | 2/2007 | Kozak |
| 7,179,951 | B2 | 2/2007 | Krishnaswamy-Mirle et al. |
| 7,181,781 | B1 | 2/2007 | Trabold et al. |
| 7,186,245 | B1 | 3/2007 | Cheng et al. |
| 7,192,424 | B2 | 3/2007 | Cooper |
| 7,219,764 | B1 | 5/2007 | Forbes |
| 7,220,250 | B2 | 5/2007 | Suzuki et al. |
| D562,975 | S | 2/2008 | Otto |
| 7,335,189 | B2 | 2/2008 | Harvie |
| 7,358,282 | B2 | 4/2008 | Krueger et al. |
| 7,390,320 | B2 | 6/2008 | Machida et al. |
| 7,438,706 | B2 | 10/2008 | Koizumi et al. |
| 7,488,310 | B2 | 2/2009 | Yang |
| 7,491,194 | B1 | 2/2009 | Oliwa |
| D591,106 | S | 4/2009 | Dominique et al. |
| 7,513,381 | B2 | 4/2009 | Heng et al. |
| 7,520,872 | B2 | 4/2009 | Biggie et al. |
| D593,801 | S | 6/2009 | Wilson et al. |
| 7,540,364 | B2 | 6/2009 | Sanderson |
| 7,549,511 | B2 | 6/2009 | Marocco |
| 7,549,512 | B2 | 6/2009 | Newberry |
| 7,585,293 | B2 | 9/2009 | Vermaak |
| 7,588,560 | B1 | 9/2009 | Dunlop |
| 7,637,905 | B2 | 12/2009 | Saadat et al. |
| 7,658,730 | B2 | 2/2010 | Conley |
| 7,665,359 | B2 | 2/2010 | Barber |
| 7,682,347 | B2 | 3/2010 | Parks et al. |
| 7,687,004 | B2 | 3/2010 | Allen |
| 7,695,459 | B2 | 4/2010 | Gilbert et al. |
| 7,695,460 | B2 | 4/2010 | Wada et al. |
| 7,699,818 | B2 | 4/2010 | Gilbert |
| 7,699,831 | B2 | 4/2010 | Bengtson et al. |
| 7,722,584 | B2 | 5/2010 | Tanaka et al. |
| 7,727,206 | B2 | 6/2010 | Gorres |
| 7,740,620 | B2 | 6/2010 | Gilbert et al. |
| 7,749,205 | B2 | 7/2010 | Tazoe et al. |
| 7,755,497 | B2 | 7/2010 | Wada et al. |
| 7,766,887 | B2 | 8/2010 | Burns et al. |
| 7,803,144 | B1 | 9/2010 | Vollrath |
| D625,407 | S | 10/2010 | Koizumi et al. |
| 7,806,879 | B2 | 10/2010 | Brooks et al. |
| 7,811,272 | B2 | 10/2010 | Lindsay et al. |
| 7,815,067 | B2 | 10/2010 | Matsumoto et al. |
| 7,833,169 | B2 | 11/2010 | Hannon |
| 7,857,806 | B2 | 12/2010 | Karpowicz et al. |
| 7,866,942 | B2 | 1/2011 | Harvie |
| 7,871,385 | B2 | 1/2011 | Levinson et al. |
| 7,875,010 | B2 | 1/2011 | Frazier et al. |
| 7,901,389 | B2 | 3/2011 | Mombrinie |
| 7,927,320 | B2 | 4/2011 | Goldwasser et al. |
| 7,927,321 | B2 | 4/2011 | Marland |
| 7,931,634 | B2 | 4/2011 | Swiecicki et al. |
| 7,939,706 | B2 | 5/2011 | Okabe et al. |
| 7,946,443 | B2 | 5/2011 | Stull et al. |
| 7,947,025 | B2 | 5/2011 | Buglino et al. |
| 7,963,419 | B2 | 6/2011 | Burney et al. |
| 7,976,519 | B2 | 7/2011 | Bubb et al. |
| 7,993,318 | B2 | 8/2011 | Olsson et al. |
| 8,015,627 | B2 | 9/2011 | Baker et al. |
| 8,016,071 | B1 | 9/2011 | Martinus et al. |
| 8,028,460 | B2 | 10/2011 | Williams |
| 8,047,398 | B2 | 11/2011 | Dimartino et al. |
| 8,083,094 | B2 | 12/2011 | Caulfield et al. |
| 8,128,608 | B2 | 3/2012 | Thevenin |
| 8,167,860 | B1 | 5/2012 | Siegel |
| 8,181,651 | B2 | 5/2012 | Pinel |
| 8,181,819 | B2 | 5/2012 | Burney et al. |
| 8,211,063 | B2 | 7/2012 | Bierman et al. |
| 8,221,369 | B2 | 7/2012 | Parks et al. |
| 8,241,262 | B2 | 8/2012 | Mahnensmith |
| 8,277,426 | B2 | 10/2012 | Wilcox et al. |
| 8,287,508 | B1 | 10/2012 | Sanchez |
| 8,303,554 | B2 | 11/2012 | Tsai et al. |
| 8,322,565 | B2 | 12/2012 | Caulfield et al. |
| 8,337,477 | B2 | 12/2012 | Parks et al. |
| D674,241 | S | 1/2013 | Bickert et al. |
| 8,343,122 | B2 | 1/2013 | Gorres |
| 8,343,125 | B2 | 1/2013 | Kawazoe et al. |
| 8,353,074 | B2 | 1/2013 | Krebs |
| 8,353,886 | B2 | 1/2013 | Bester et al. |
| D676,241 | S | 2/2013 | Merrill |
| 8,388,587 | B1 | 3/2013 | Gmuer et al. |
| 8,388,588 | B2 | 3/2013 | Wada et al. |
| D679,807 | S | 4/2013 | Burgess et al. |
| 8,425,482 | B2 | 4/2013 | Khoubnazar |
| 8,434,586 | B2 | 5/2013 | Pawelski et al. |
| 8,449,510 | B2 | 5/2013 | Martini et al. |
| D684,260 | S | 6/2013 | Lund et al. |
| 8,470,230 | B2 | 6/2013 | Caulfield et al. |
| 8,479,941 | B2 | 7/2013 | Matsumoto et al. |
| 8,479,949 | B2 | 7/2013 | Henkel |

(56) References Cited

U.S. PATENT DOCUMENTS

| | | | |
|---|---|---|---|
| 8,500,719 B1 | 8/2013 | Simpson et al. |
| 8,512,301 B2 | 8/2013 | Ma |
| 8,529,530 B2 | 9/2013 | Koch et al. |
| 8,535,284 B2 | 9/2013 | Joder et al. |
| 8,546,639 B2 | 10/2013 | Wada et al. |
| 8,551,062 B2 | 10/2013 | Kay |
| 8,551,075 B2 | 10/2013 | Bengtson |
| 8,568,376 B2 | 10/2013 | Delattre et al. |
| D694,404 S | 11/2013 | Burgess et al. |
| 8,585,683 B2 | 11/2013 | Bengtson et al. |
| 8,586,583 B2 | 11/2013 | Hamblin et al. |
| 8,652,112 B2 | 2/2014 | Johannison et al. |
| 8,669,412 B2 | 3/2014 | Fernkvist et al. |
| D702,973 S | 4/2014 | Norland et al. |
| 8,703,032 B2 | 4/2014 | Menon et al. |
| D704,330 S | 5/2014 | Cicatelli |
| D704,510 S | 5/2014 | Mason et al. |
| D705,423 S | 5/2014 | Walsh Cutler |
| D705,926 S | 5/2014 | Burgess et al. |
| 8,714,394 B2 | 5/2014 | Wulf |
| 8,715,267 B2 | 5/2014 | Bengtson et al. |
| 8,757,425 B2 | 6/2014 | Copeland |
| 8,777,032 B2 | 7/2014 | Biesecker et al. |
| 8,808,260 B2 | 8/2014 | Koch et al. |
| 8,864,730 B2 | 10/2014 | Conway et al. |
| 8,881,923 B2 | 11/2014 | Higginson |
| 8,882,731 B2 | 11/2014 | Suzuki et al. |
| 8,936,585 B2 | 1/2015 | Carson et al. |
| D729,581 S | 5/2015 | Boroski |
| 9,028,460 B2 | 5/2015 | Medeiros |
| 9,056,698 B2 | 6/2015 | Noer |
| 9,078,792 B2 | 7/2015 | Ruiz |
| 9,145,879 B2 | 9/2015 | Pirovano et al. |
| 9,173,602 B2 | 11/2015 | Gilbert |
| 9,173,799 B2 | 11/2015 | Tanimoto et al. |
| 9,187,220 B2 | 11/2015 | Biesecker et al. |
| 9,199,772 B2 | 12/2015 | Krippendorf |
| 9,233,020 B2 | 1/2016 | Matsumiya |
| 9,248,058 B2 | 2/2016 | Conway et al. |
| 9,308,118 B1 | 4/2016 | Dupree et al. |
| 9,309,029 B2 | 4/2016 | Incorvia et al. |
| 9,333,281 B2 | 5/2016 | Giezendanner et al. |
| 9,381,108 B2 | 7/2016 | Longoni et al. |
| 9,382,047 B2 | 7/2016 | Schmidtner et al. |
| 9,402,424 B2 | 8/2016 | Roy |
| 9,456,937 B2 | 10/2016 | Ellis |
| 9,480,595 B2 | 11/2016 | Baham et al. |
| 9,517,865 B2 | 12/2016 | Albers et al. |
| D777,941 S | 1/2017 | Piramoon |
| 9,533,806 B2 | 1/2017 | Ding et al. |
| 9,550,611 B2 | 1/2017 | Hodge |
| 9,555,930 B2 | 1/2017 | Campbell et al. |
| 9,623,159 B2 | 4/2017 | Locke |
| D789,522 S | 6/2017 | Burgess et al. |
| 9,687,849 B2 | 6/2017 | Bruno et al. |
| 9,694,949 B2 | 7/2017 | Hendricks et al. |
| 9,709,048 B2 | 7/2017 | Kinjo |
| 9,713,547 B2 | 7/2017 | Lee et al. |
| 9,732,754 B2 | 8/2017 | Huang et al. |
| 9,737,433 B2 | 8/2017 | Joh |
| 9,752,564 B2 | 9/2017 | Arceno et al. |
| 9,788,992 B2 | 10/2017 | Harvie |
| D804,907 S | 12/2017 | Sandoval |
| 9,868,564 B2 | 1/2018 | Mcgirr et al. |
| D814,239 S | 4/2018 | Arora |
| D817,484 S | 5/2018 | Lafond |
| 9,968,908 B2 | 5/2018 | Ladrech et al. |
| 10,010,393 B1 | 7/2018 | Nguyen et al. |
| 10,037,640 B2 | 7/2018 | Gordon |
| 10,058,470 B2 | 8/2018 | Phillips |
| 10,098,990 B2 | 10/2018 | Koch et al. |
| D835,264 S | 12/2018 | Mozzicato et al. |
| D835,779 S | 12/2018 | Mozzicato et al. |
| D840,533 S | 2/2019 | Mozzicato et al. |
| D840,534 S | 2/2019 | Mozzicato et al. |
| 10,225,376 B2 | 3/2019 | Perez Martinez |
| 10,226,376 B2 | 3/2019 | Sanchez et al. |
| 10,258,517 B1 | 4/2019 | Maschino et al. |
| D848,612 S | 5/2019 | Mozzicato et al. |
| 10,307,305 B1 | 6/2019 | Hodges |
| 10,335,121 B2 | 7/2019 | Desai |
| D856,512 S | 8/2019 | Cowart et al. |
| 10,376,406 B2 | 8/2019 | Newton |
| 10,376,407 B2 | 8/2019 | Newton |
| 10,390,989 B2 | 8/2019 | Sanchez et al. |
| D858,144 S | 9/2019 | Fu |
| 10,406,039 B2 | 9/2019 | Mllarreal |
| 10,407,222 B2 | 9/2019 | Allen |
| 10,478,356 B2 | 11/2019 | Griffin |
| 10,500,108 B1 | 12/2019 | Maschino et al. |
| 10,502,198 B2 | 12/2019 | Stumpf et al. |
| 10,538,366 B2 | 1/2020 | Pentelovitch et al. |
| 10,569,938 B2 | 2/2020 | Zhao et al. |
| 10,577,156 B2 | 3/2020 | Dagnelie et al. |
| RE47,930 E | 4/2020 | Cho |
| 10,618,721 B2 | 4/2020 | Vazin |
| D884,390 S | 5/2020 | Wang |
| 10,669,079 B2 | 6/2020 | Freedman et al. |
| D892,315 S | 8/2020 | Airy |
| 10,730,672 B2 | 8/2020 | Bertram et al. |
| 10,737,848 B2 | 8/2020 | Philip et al. |
| 10,765,854 B2 | 9/2020 | Law et al. |
| 10,766,670 B2 | 9/2020 | Kittmann |
| 10,799,386 B1 | 10/2020 | Harrison |
| 10,806,642 B2 | 10/2020 | Tagomori et al. |
| D901,214 S | 11/2020 | Hu |
| 10,849,799 B2 | 12/2020 | Nishikawa et al. |
| 10,857,025 B2 | 12/2020 | Davis et al. |
| 10,865,017 B1 | 12/2020 | Cowart et al. |
| 10,889,412 B2 | 1/2021 | West et al. |
| 10,913,581 B2 | 2/2021 | Stahlecker |
| D912,244 S | 3/2021 | Rehm et al. |
| 10,952,889 B2 | 3/2021 | Newton et al. |
| 10,973,378 B2 | 4/2021 | Ryu et al. |
| 10,973,678 B2 | 4/2021 | Newton et al. |
| 10,974,874 B2 | 4/2021 | Ragias et al. |
| 11,000,401 B2 | 5/2021 | Ecklund et al. |
| 11,002,165 B2 | 5/2021 | Poulin |
| D923,365 S | 6/2021 | Wang |
| 11,026,829 B2 | 6/2021 | Harvie |
| 11,027,900 B2 | 6/2021 | Liu |
| 11,045,346 B2 | 6/2021 | Argent et al. |
| D928,946 S | 8/2021 | Sanchez et al. |
| 11,090,183 B2 | 8/2021 | Sanchez et al. |
| 11,160,695 B2 | 11/2021 | Febo et al. |
| 11,160,697 B2 | 11/2021 | Maschino et al. |
| 11,168,420 B2 | 11/2021 | Kinugasa et al. |
| 11,179,506 B2 | 11/2021 | Barr et al. |
| 11,199,116 B2 | 12/2021 | Ostromecki et al. |
| 11,207,206 B2 | 12/2021 | Sharma et al. |
| 11,226,376 B2 | 1/2022 | Yamauchi et al. |
| 11,253,389 B2 | 2/2022 | Sharma et al. |
| 11,253,407 B2 | 2/2022 | Miao et al. |
| 11,326,586 B2 | 5/2022 | Milner et al. |
| 11,369,508 B2 | 6/2022 | Ecklund et al. |
| 11,369,524 B2 | 6/2022 | Hubbard et al. |
| 11,376,152 B2 | 7/2022 | Sanchez et al. |
| 11,382,786 B2 | 7/2022 | Sanchez et al. |
| 11,382,788 B2 | 7/2022 | Hjorth et al. |
| 11,389,318 B2 | 7/2022 | Radl et al. |
| 11,395,871 B2 | 7/2022 | Radl et al. |
| 11,399,990 B2 | 8/2022 | Suyama |
| 11,426,303 B2 | 8/2022 | Davis et al. |
| 11,504,265 B2 | 11/2022 | Godinez et al. |
| 11,529,252 B2 | 12/2022 | Glithero et al. |
| 11,547,788 B2 | 1/2023 | Radl et al. |
| 11,806,266 B2 | 11/2023 | Sanchez et al. |
| 11,839,567 B2 | 12/2023 | Davis et al. |
| D1,010,109 S | 1/2024 | Ecklund et al. |
| 11,857,716 B2 | 1/2024 | Lee et al. |
| 11,865,030 B2 | 1/2024 | Davis et al. |
| 11,890,221 B2 | 2/2024 | Ulreich et al. |
| 11,911,160 B2 | 2/2024 | Woodard et al. |
| 11,925,575 B2 | 3/2024 | Newton |

(56) References Cited

U.S. PATENT DOCUMENTS

| | | |
|---|---|---|
| 11,938,053 B2 | 3/2024 | Austermann et al. |
| 11,944,740 B2 | 4/2024 | Hughett et al. |
| 11,994,122 B2 | 5/2024 | Bodain |
| 11,998,475 B2 | 6/2024 | Becker et al. |
| 12,023,457 B2 | 7/2024 | Mann et al. |
| 12,042,422 B2 | 7/2024 | Davis et al. |
| D1,038,385 S | 8/2024 | Ecklund et al. |
| 12,064,372 B2 | 8/2024 | Godinez et al. |
| 12,070,432 B2 | 8/2024 | Tourchak et al. |
| 12,090,083 B2 | 9/2024 | Ecklund et al. |
| 12,133,813 B2 | 11/2024 | Ulreich et al. |
| 12,138,195 B2 | 11/2024 | Alder et al. |
| 12,186,229 B2 | 1/2025 | Davis et al. |
| 2001/0037097 A1 | 11/2001 | Cheng et al. |
| 2001/0037098 A1 | 11/2001 | Snyder |
| 2001/0054426 A1 | 12/2001 | Knudson et al. |
| 2002/0019614 A1 | 2/2002 | Woon |
| 2002/0026161 A1 | 2/2002 | Grundke |
| 2002/0026163 A1 | 2/2002 | Grundke |
| 2002/0042945 A1 | 4/2002 | Sands |
| 2002/0087131 A1 | 7/2002 | Wolff et al. |
| 2002/0091364 A1 | 7/2002 | Prabhakar |
| 2002/0189992 A1 | 12/2002 | Schmidt et al. |
| 2002/0193760 A1 | 12/2002 | Thompson |
| 2002/0193762 A1 | 12/2002 | Suydam |
| 2003/0004436 A1 | 1/2003 | Schmidt et al. |
| 2003/0032931 A1 | 2/2003 | Grundke et al. |
| 2003/0032944 A1 | 2/2003 | Cawood |
| 2003/0073964 A1 | 4/2003 | Palumbo et al. |
| 2003/0074724 A1 | 4/2003 | Sands |
| 2003/0120178 A1 | 6/2003 | Heki |
| 2003/0129178 A1 | 7/2003 | Wegman et al. |
| 2003/0157859 A1 | 8/2003 | Ishikawa |
| 2003/0181880 A1 | 9/2003 | Schwartz |
| 2003/0195484 A1 | 10/2003 | Harvie |
| 2003/0204173 A1 | 10/2003 | Burns et al. |
| 2003/0233079 A1 | 12/2003 | Parks et al. |
| 2004/0006321 A1 | 1/2004 | Cheng et al. |
| 2004/0015141 A1 | 1/2004 | Cheng et al. |
| 2004/0056122 A1 | 3/2004 | Male et al. |
| 2004/0084465 A1 | 5/2004 | Luburic |
| 2004/0127872 A1 | 7/2004 | Petryk et al. |
| 2004/0128749 A1 | 7/2004 | Scott |
| 2004/0143229 A1 | 7/2004 | Easter |
| 2004/0147863 A1 | 7/2004 | Diaz et al. |
| 2004/0147894 A1 | 7/2004 | Mizutani et al. |
| 2004/0147895 A1 | 7/2004 | Mizutani et al. |
| 2004/0158221 A1 | 8/2004 | Mizutani et al. |
| 2004/0176731 A1 | 9/2004 | Cheng et al. |
| 2004/0176746 A1 | 9/2004 | Forral |
| 2004/0181201 A1 | 9/2004 | Mizutani et al. |
| 2004/0191919 A1 | 9/2004 | Unger et al. |
| 2004/0194792 A1 | 10/2004 | Zhuang et al. |
| 2004/0200936 A1 | 10/2004 | Opperthauser |
| 2004/0207530 A1 | 10/2004 | Nielsen |
| 2004/0236292 A1 | 11/2004 | Tazoe et al. |
| 2004/0243075 A1 | 12/2004 | Harvie |
| 2004/0254547 A1 | 12/2004 | Okabe et al. |
| 2005/0010182 A1 | 1/2005 | Parks et al. |
| 2005/0010197 A1 | 1/2005 | Lau et al. |
| 2005/0033248 A1 | 2/2005 | Machida et al. |
| 2005/0065471 A1 | 3/2005 | Kuntz |
| 2005/0070861 A1 | 3/2005 | Okabe et al. |
| 2005/0070862 A1 | 3/2005 | Tazoe et al. |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0119630 A1 | 6/2005 | Harvie |
| 2005/0131361 A1 | 6/2005 | Miskie |
| 2005/0137557 A1 | 6/2005 | Swiecicki et al. |
| 2005/0137560 A1 | 6/2005 | Mizutani et al. |
| 2005/0137561 A1 | 6/2005 | Mizutani et al. |
| 2005/0154360 A1 | 7/2005 | Harvie |
| 2005/0177070 A1 | 8/2005 | Levinson et al. |
| 2005/0197639 A1 | 9/2005 | Mombrinie |
| 2005/0197645 A1 | 9/2005 | Karpowicz et al. |
| 2005/0215969 A1 | 9/2005 | Mizutani et al. |
| 2005/0273069 A1 | 12/2005 | Mizutani et al. |
| 2005/0273920 A1 | 12/2005 | Marinas |
| 2005/0277903 A1 | 12/2005 | Mizutani et al. |
| 2005/0277904 A1 | 12/2005 | Chase et al. |
| 2005/0279359 A1 | 12/2005 | Leblanc et al. |
| 2006/0004332 A1 | 1/2006 | Marx |
| 2006/0015080 A1 | 1/2006 | Mahnensmith |
| 2006/0015081 A1 | 1/2006 | Suzuki et al. |
| 2006/0016778 A1 | 1/2006 | Park |
| 2006/0069359 A1 | 3/2006 | Dipalma et al. |
| 2006/0079854 A1 | 4/2006 | Kay et al. |
| 2006/0111648 A1 | 5/2006 | Vermaak |
| 2006/0113334 A1 | 6/2006 | Mikhail et al. |
| 2006/0155214 A1 | 7/2006 | Wightman |
| 2006/0171997 A1 | 8/2006 | Gruenbacher et al. |
| 2006/0180566 A1 | 8/2006 | Mataya |
| 2006/0200102 A1 | 9/2006 | Cooper |
| 2006/0229575 A1 | 10/2006 | Boiarski |
| 2006/0229576 A1 | 10/2006 | Conway et al. |
| 2006/0231648 A1 | 10/2006 | Male et al. |
| 2006/0235266 A1 | 10/2006 | Nan |
| 2006/0235359 A1 | 10/2006 | Marland |
| 2006/0241553 A1 | 10/2006 | Harvie |
| 2006/0269439 A1 | 11/2006 | White |
| 2006/0277670 A1 | 12/2006 | Baker et al. |
| 2007/0006368 A1 | 1/2007 | Key et al. |
| 2007/0010797 A1 | 1/2007 | Nishtala et al. |
| 2007/0016152 A1 | 1/2007 | Karpowicz et al. |
| 2007/0038194 A1 | 2/2007 | Wada et al. |
| 2007/0055209 A1 | 3/2007 | Patel et al. |
| 2007/0073252 A1 | 3/2007 | Forgrave |
| 2007/0117880 A1 | 5/2007 | Elson et al. |
| 2007/0118993 A1 | 5/2007 | Bates |
| 2007/0135786 A1 | 6/2007 | Schmidt et al. |
| 2007/0137718 A1 | 6/2007 | Rushlander et al. |
| 2007/0149935 A1 | 6/2007 | Dirico |
| 2007/0191804 A1 | 8/2007 | Coley |
| 2007/0203464 A1 | 8/2007 | Green et al. |
| 2007/0214553 A1 | 9/2007 | Carromba et al. |
| 2007/0225663 A1 | 9/2007 | Watt et al. |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0077099 A1 | 3/2008 | House |
| 2008/0091153 A1 | 4/2008 | Harvie |
| 2008/0091158 A1 | 4/2008 | Yang |
| 2008/0114327 A1 | 5/2008 | Barge |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0269703 A1 | 10/2008 | Collins et al. |
| 2008/0281282 A1 | 11/2008 | Finger et al. |
| 2008/0287894 A1 | 11/2008 | Van Den Heuvel et al. |
| 2008/0312550 A1 | 12/2008 | Nishtala et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0120179 A1 | 5/2009 | Nylander et al. |
| 2009/0192482 A1 | 7/2009 | Dodge et al. |
| 2009/0226541 A1 | 9/2009 | Scholz et al. |
| 2009/0234312 A1 | 9/2009 | Otoole et al. |
| 2009/0251510 A1 | 10/2009 | Noro et al. |
| 2009/0259206 A1 | 10/2009 | Kai et al. |
| 2009/0264840 A1 | 10/2009 | Mrginio |
| 2009/0270822 A1 | 10/2009 | Medeiros |
| 2009/0281510 A1 | 11/2009 | Fisher |
| 2009/0283982 A1 | 11/2009 | Thomas |
| 2009/0306610 A1 | 12/2009 | Van Den Heuvel et al. |

(56)            References Cited

U.S. PATENT DOCUMENTS

| | | |
|---|---|---|
| 2010/0004612 A1 | 1/2010 | Thevenin |
| 2010/0031429 A1 | 2/2010 | Kim et al. |
| 2010/0032789 A1 | 2/2010 | Schoen et al. |
| 2010/0058660 A1 | 3/2010 | Williams |
| 2010/0121289 A1 | 5/2010 | Parks et al. |
| 2010/0158168 A1 | 6/2010 | Murthy et al. |
| 2010/0160882 A1 | 6/2010 | Lowe |
| 2010/0174250 A1 | 7/2010 | Hu et al. |
| 2010/0179493 A1 | 7/2010 | Heagle et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060299 A1 | 3/2011 | Wada et al. |
| 2011/0060300 A1 | 3/2011 | Weig et al. |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0137273 A1 | 6/2011 | Muellejans et al. |
| 2011/0145993 A1 | 6/2011 | Rader et al. |
| 2011/0152802 A1 | 6/2011 | Dicamillo et al. |
| 2011/0164147 A1 | 7/2011 | Takahashi et al. |
| 2011/0172620 A1 | 7/2011 | Khambatta |
| 2011/0172625 A1 | 7/2011 | Wada et al. |
| 2011/0198904 A1 | 8/2011 | Thomas et al. |
| 2011/0202024 A1 | 8/2011 | Cozzens |
| 2011/0238023 A1 | 9/2011 | Slayton |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0029452 A1 | 2/2012 | Roedsten |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1 | 5/2012 | Wheaton et al. |
| 2012/0116336 A1 | 5/2012 | Sharma et al. |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0209216 A1 | 8/2012 | Jensen et al. |
| 2012/0209225 A1* | 8/2012 | Hu .......................... A61M 1/98 |
| | | 604/319 |
| 2012/0210503 A1 | 8/2012 | Anzivino et al. |
| 2012/0233761 A1 | 9/2012 | Huang |
| 2012/0245541 A1 | 9/2012 | Suzuki et al. |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |
| 2012/0271259 A1 | 10/2012 | Ulert |
| 2012/0296305 A1 | 11/2012 | Barraza Khaled et al. |
| 2012/0316522 A1 | 12/2012 | Carter et al. |
| 2012/0330256 A1 | 12/2012 | Wilcox et al. |
| 2013/0006206 A1 | 1/2013 | Wada et al. |
| 2013/0019374 A1 | 1/2013 | Schwartz |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0110059 A1 | 5/2013 | Kossow et al. |
| 2013/0138064 A1 | 5/2013 | Stroebech et al. |
| 2013/0150813 A1 | 6/2013 | Gordon et al. |
| 2013/0165880 A1 | 6/2013 | Amos et al. |
| 2013/0218112 A1 | 8/2013 | Thompson |
| 2013/0245496 A1 | 9/2013 | Wells et al. |
| 2013/0245586 A1 | 9/2013 | Jha |
| 2013/0292537 A1 | 11/2013 | Dirico |
| 2013/0330501 A1 | 12/2013 | Aizenberg et al. |
| 2014/0005647 A1 | 1/2014 | Shuffler et al. |
| 2014/0031774 A1 | 1/2014 | Bengtson |
| 2014/0039432 A1 | 2/2014 | Dunbar et al. |
| 2014/0039440 A1 | 2/2014 | Doescher |
| 2014/0058347 A1 | 2/2014 | Marquette |
| 2014/0107599 A1 | 4/2014 | Fink et al. |
| 2014/0157499 A1 | 6/2014 | Suzuki et al. |
| 2014/0171889 A1 | 6/2014 | Hopman et al. |
| 2014/0182051 A1 | 7/2014 | Tanimoto et al. |
| 2014/0196189 A1 | 7/2014 | Lee et al. |
| 2014/0276501 A1 | 9/2014 | Cisko |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209188 A1 | 7/2015 | Scheremet et al. |
| 2015/0209194 A1 | 7/2015 | Heyman |
| 2015/0267862 A1 | 9/2015 | Mishler |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0342799 A1 | 12/2015 | Michiels et al. |
| 2015/0359660 A1 | 12/2015 | Harvie |
| 2015/0359996 A1 | 12/2015 | Arora et al. |
| 2015/0366699 A1 | 12/2015 | Nelson |
| 2016/0029998 A1 | 2/2016 | Brister et al. |
| 2016/0030228 A1 | 2/2016 | Jones |
| 2016/0038356 A1 | 2/2016 | Yao et al. |
| 2016/0051395 A1 | 2/2016 | Ugarte |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1 | 4/2016 | Timm |
| 2016/0113809 A1 | 4/2016 | Kim |
| 2016/0136338 A1 | 5/2016 | Lee et al. |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0357400 A1 | 12/2016 | Penha et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0367726 A1 | 12/2016 | Gratzer |
| 2016/0374848 A1 | 12/2016 | Sanchez et al. |
| 2017/0007438 A1 | 1/2017 | Harvie |
| 2017/0014560 A1 | 1/2017 | Minskoff et al. |
| 2017/0042724 A1 | 2/2017 | Ugarte |
| 2017/0042748 A1 | 2/2017 | Griffin |
| 2017/0100276 A1 | 4/2017 | Joh |
| 2017/0107312 A1 | 4/2017 | Hinayama et al. |
| 2017/0128638 A1 | 5/2017 | Giezendanner et al. |
| 2017/0136209 A1 | 5/2017 | Burnett et al. |
| 2017/0143534 A1 | 5/2017 | Sanchez |
| 2017/0165100 A1 | 6/2017 | Jackson et al. |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0238911 A1 | 8/2017 | Duval |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1 | 9/2017 | Sanchez et al. |
| 2017/0266658 A1 | 9/2017 | Bruno et al. |
| 2017/0281399 A1 | 10/2017 | Vanmiddendorp et al. |
| 2017/0281419 A1 | 10/2017 | Pintado |
| 2017/0312116 A1 | 11/2017 | Laniado |
| 2017/0325788 A1 | 11/2017 | Ealovega et al. |

(56)                References Cited

U.S. PATENT DOCUMENTS

| | | |
|---|---|---|
| 2017/0333244 A1 | 11/2017 | Laniado |
| 2017/0348139 A1 | 12/2017 | Newton et al. |
| 2017/0354532 A1 | 12/2017 | Holt |
| 2017/0354551 A1 | 12/2017 | Gawley et al. |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0021218 A1 | 1/2018 | Brosch et al. |
| 2018/0028349 A1 | 2/2018 | Newton et al. |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0193215 A1 | 7/2018 | Davies et al. |
| 2018/0200101 A1 | 7/2018 | Su |
| 2018/0228642 A1 | 8/2018 | Davis et al. |
| 2018/0256384 A1 | 9/2018 | Kasirye |
| 2018/0271694 A1 | 9/2018 | Fernandez et al. |
| 2018/0317892 A1 | 11/2018 | Catlin |
| 2018/0325748 A1 | 11/2018 | Sharma et al. |
| 2019/0001030 A1 | 1/2019 | Braga et al. |
| 2019/0021899 A1 | 1/2019 | Vlet |
| 2019/0038451 A1 | 2/2019 | Harvie |
| 2019/0046102 A1 | 2/2019 | Kushnir et al. |
| 2019/0059938 A1 | 2/2019 | Holsten |
| 2019/0091059 A1 | 3/2019 | Gabriel |
| 2019/0100362 A1 | 4/2019 | Meyers et al. |
| 2019/0133126 A1 | 5/2019 | Modak et al. |
| 2019/0133814 A1 | 5/2019 | Tammen et al. |
| 2019/0142624 A1 | 5/2019 | Sanchez et al. |
| 2019/0224036 A1 | 7/2019 | Sanchez et al. |
| 2019/0226189 A1 | 7/2019 | Braxton |
| 2019/0240079 A1 | 8/2019 | Tuli |
| 2019/0247222 A1 | 8/2019 | Ecklund et al. |
| 2019/0247223 A1 | 8/2019 | Brun et al. |
| 2019/0247623 A1 | 8/2019 | Helm et al. |
| 2019/0282391 A1 | 9/2019 | Johannes et al. |
| 2019/0314189 A1 | 10/2019 | Acosta |
| 2019/0314190 A1 | 10/2019 | Sanchez et al. |
| 2019/0321587 A1 | 10/2019 | Mcmenamin et al. |
| 2019/0344934 A1 | 11/2019 | Faerber et al. |
| 2019/0365303 A1 | 12/2019 | Bullington et al. |
| 2019/0365307 A1 | 12/2019 | Laing et al. |
| 2019/0365561 A1 | 12/2019 | Newton et al. |
| 2019/0374373 A1 | 12/2019 | Joh |
| 2020/0008985 A1 | 1/2020 | Nguyen et al. |
| 2020/0016012 A1 | 1/2020 | Dutkiewicz |
| 2020/0030595 A1 | 1/2020 | Boukidjian et al. |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085609 A1 | 3/2020 | Schelch et al. |
| 2020/0085610 A1 | 3/2020 | Cohn et al. |
| 2020/0086090 A1 | 3/2020 | Von Weymarn-Schärli et al. |
| 2020/0107518 A1 | 4/2020 | Hiroshima et al. |
| 2020/0129322 A1 | 4/2020 | Leuckel |
| 2020/0171217 A9 | 6/2020 | Braga et al. |
| 2020/0179177 A1 | 6/2020 | Erdem et al. |
| 2020/0187918 A1 | 6/2020 | Wiygul |
| 2020/0206015 A1 | 7/2020 | Langer |
| 2020/0206039 A1 | 7/2020 | Mclain |
| 2020/0214910 A1 | 7/2020 | Varona et al. |
| 2020/0216898 A1 | 7/2020 | Hubbell |
| 2020/0216989 A1 | 7/2020 | Kinugasa et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0246172 A1 | 8/2020 | Ho |
| 2020/0246203 A1 | 8/2020 | Tulk et al. |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315837 A1 | 10/2020 | Radl et al. |
| 2020/0315838 A1 | 10/2020 | Eckert |
| 2020/0315872 A1 | 10/2020 | Viens et al. |
| 2020/0315874 A1 | 10/2020 | Viens et al. |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1 | 12/2020 | Staali et al. |
| 2020/0375810 A1 | 12/2020 | Carlin et al. |
| 2020/0384242 A1 | 12/2020 | Havard et al. |
| 2020/0385179 A1 | 12/2020 | Mccourt |
| 2020/0390591 A1 | 12/2020 | Glithero et al. |
| 2020/0390592 A1 | 12/2020 | Merrill |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0020072 A1 | 1/2021 | Moehring et al. |
| 2021/0023279 A1 | 1/2021 | Radl et al. |
| 2021/0059853 A1 | 3/2021 | Davis et al. |
| 2021/0061523 A1 | 3/2021 | Bytheway |
| 2021/0069005 A1 | 3/2021 | Sanchez et al. |
| 2021/0069008 A1 | 3/2021 | Blabas et al. |
| 2021/0069009 A1 | 3/2021 | Im |
| 2021/0069030 A1 | 3/2021 | Nishikawa et al. |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Villarreal |
| 2021/0170079 A1 | 6/2021 | Radl et al. |
| 2021/0178390 A1 | 6/2021 | Oueslati et al. |
| 2021/0186742 A1 | 6/2021 | Newton et al. |
| 2021/0211568 A1 | 7/2021 | Zhou et al. |
| 2021/0212865 A1 | 7/2021 | Wallajapet et al. |
| 2021/0220162 A1 | 7/2021 | Jamison |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1 | 7/2021 | Hughett et al. |
| 2021/0229877 A1 | 7/2021 | Ragias et al. |
| 2021/0236323 A1 | 8/2021 | Austermann et al. |
| 2021/0236324 A1 | 8/2021 | Sweeney |
| 2021/0251814 A1 | 8/2021 | Jönegren et al. |
| 2021/0267787 A1 | 9/2021 | Nazemi |
| 2021/0275343 A1 | 9/2021 | Sanchez et al. |
| 2021/0275344 A1 | 9/2021 | Wing |
| 2021/0290454 A1 | 9/2021 | Yamada |
| 2021/0315726 A1 | 10/2021 | Lin |
| 2021/0315727 A1 | 10/2021 | Jiang |
| 2021/0353449 A1 | 11/2021 | Sharma et al. |
| 2021/0353450 A1* | 11/2021 | Sharma ........... A61F 5/4408 |
| 2021/0361469 A1 | 11/2021 | Liu et al. |
| 2021/0369495 A1 | 12/2021 | Cheng et al. |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |
| 2022/0031290 A1 | 2/2022 | Weed |
| 2022/0031523 A1 | 2/2022 | Pierpoint |
| 2022/0039995 A1 | 2/2022 | Johannes et al. |
| 2022/0047410 A1* | 2/2022 | Walthall ........... A61M 1/73 |
| 2022/0062027 A1 | 3/2022 | Mitchell et al. |
| 2022/0062028 A1 | 3/2022 | Mitchell et al. |
| 2022/0062029 A1 | 3/2022 | Johannes et al. |
| 2022/0066825 A1 | 3/2022 | Saraf et al. |
| 2022/0071811 A1 | 3/2022 | Cheng et al. |
| 2022/0071826 A1 | 3/2022 | Kulkarni et al. |
| 2022/0104965 A1 | 4/2022 | Vaninetti et al. |
| 2022/0104976 A1 | 4/2022 | Hoeger et al. |
| 2022/0104981 A1 | 4/2022 | Jones |
| 2022/0117773 A1 | 4/2022 | Davis et al. |
| 2022/0117774 A1 | 4/2022 | Meyer et al. |
| 2022/0117775 A1 | 4/2022 | Jones et al. |
| 2022/0118165 A1 | 4/2022 | Knapp et al. |
| 2022/0133524 A1 | 5/2022 | Davis |
| 2022/0151817 A1 | 5/2022 | Mann |
| 2022/0160949 A1 | 5/2022 | Simiele et al. |

(56) References Cited

U.S. PATENT DOCUMENTS

| | | |
|---|---|---|
| 2022/0168159 A1 | 6/2022 | Triado et al. |
| 2022/0193312 A1 | 6/2022 | Lee et al. |
| 2022/0211536 A1 | 7/2022 | Johannes et al. |
| 2022/0218510 A1 | 7/2022 | Metzger et al. |
| 2022/0229053 A1 | 7/2022 | Levin et al. |
| 2022/0241106 A1 | 8/2022 | Johannes et al. |
| 2022/0247407 A1 | 8/2022 | Yamamoto et al. |
| 2022/0248836 A1 | 8/2022 | Cagle et al. |
| 2022/0257407 A1 | 8/2022 | Johannes et al. |
| 2022/0265460 A1 | 8/2022 | Coker |
| 2022/0265462 A1 | 8/2022 | Alder et al. |
| 2022/0270711 A1 | 8/2022 | Feala et al. |
| 2022/0273482 A1 | 9/2022 | Johannes et al. |
| 2022/0280357 A1 | 9/2022 | Jagannathan et al. |
| 2022/0280710 A1 | 9/2022 | Agrawal et al. |
| 2022/0287689 A1 | 9/2022 | Johannes |
| 2022/0287867 A1 | 9/2022 | Jones et al. |
| 2022/0287868 A1 | 9/2022 | Garvey et al. |
| 2022/0296408 A1 | 9/2022 | Evans et al. |
| 2022/0305191 A1 | 9/2022 | Joseph et al. |
| 2022/0313222 A1 | 10/2022 | Austermann et al. |
| 2022/0313474 A1 | 10/2022 | Kriscovich et al. |
| 2022/0331170 A1 | 10/2022 | Erdem et al. |
| 2022/0339023 A1 | 10/2022 | Davis et al. |
| 2022/0339024 A1 | 10/2022 | Johannes et al. |
| 2022/0354685 A1 | 11/2022 | Davis et al. |
| 2022/0362049 A1 | 11/2022 | Austermann et al. |
| 2022/0370231 A1 | 11/2022 | Wang et al. |
| 2022/0370234 A1 | 11/2022 | Hughett et al. |
| 2022/0370235 A1 | 11/2022 | Johannes et al. |
| 2022/0370237 A1 | 11/2022 | Parmar et al. |
| 2022/0387001 A1 | 12/2022 | Askenazi et al. |
| 2022/0387693 A1 | 12/2022 | Bannwart et al. |
| 2022/0395390 A1 | 12/2022 | Brooks |
| 2022/0395391 A1 | 12/2022 | Saunders et al. |
| 2022/0401252 A1 | 12/2022 | Warren |
| 2022/0409419 A1 | 12/2022 | Garvey et al. |
| 2022/0409422 A1 | 12/2022 | Schneider et al. |
| 2023/0018845 A1 | 1/2023 | Lee |
| 2023/0020563 A1 | 1/2023 | Sharma et al. |
| 2023/0031640 A1 | 2/2023 | Hughett et al. |
| 2023/0037159 A1 | 2/2023 | Brennan et al. |
| 2023/0049924 A1 | 2/2023 | Johannes et al. |
| 2023/0052238 A1 | 2/2023 | Oluwasogo |
| 2023/0062994 A1 | 3/2023 | Ecklund et al. |
| 2023/0070347 A1 | 3/2023 | Watson et al. |
| 2023/0073708 A1 | 3/2023 | Xu et al. |
| 2023/0089032 A1 | 3/2023 | Hughett et al. |
| 2023/0091118 A1 | 3/2023 | Watson |
| 2023/0099821 A1 | 3/2023 | Radl et al. |
| 2023/0099991 A1 | 3/2023 | Bianchi et al. |
| 2023/0105001 A1 | 4/2023 | Whittome et al. |
| 2023/0110577 A1 | 4/2023 | Choi |
| 2023/0138269 A1 | 5/2023 | Abdelal et al. |
| 2023/0145365 A1* | 5/2023 | Martin .................... A61F 5/455 604/347 |
| 2023/0155253 A1 | 5/2023 | Mn et al. |
| 2023/0190511 A1* | 6/2023 | Sharma .................... A61F 5/453 604/349 |
| 2023/0210504 A1 | 7/2023 | Kuroda et al. |
| 2023/0210685 A1 | 7/2023 | Fallows et al. |
| 2023/0218426 A1 | 7/2023 | Hughett |
| 2023/0240884 A1 | 8/2023 | Davis et al. |
| 2023/0248562 A1 | 8/2023 | Sanchez et al. |
| 2023/0248564 A1 | 8/2023 | Mann et al. |
| 2023/0255812 A1 | 8/2023 | Sanchez et al. |
| 2023/0255813 A1 | 8/2023 | Sanchez et al. |
| 2023/0255815 A1 | 8/2023 | Newton |
| 2023/0263650 A1 | 8/2023 | Sanchez et al. |
| 2023/0263655 A1 | 8/2023 | Johannes et al. |
| 2023/0277360 A1 | 9/2023 | Lambert et al. |
| 2023/0277362 A1 | 9/2023 | Davis et al. |
| 2023/0285178 A1 | 9/2023 | Sanchez et al. |
| 2023/0293339 A1 | 9/2023 | James |
| 2023/0301846 A1 | 9/2023 | Greenwood |
| 2023/0355423 A1 | 11/2023 | Stevenson et al. |
| 2023/0404791 A1 | 12/2023 | Ecklund et al. |
| 2024/0008444 A1 | 1/2024 | Su et al. |
| 2024/0009023 A1 | 1/2024 | Johannes et al. |
| 2024/0024170 A1 | 1/2024 | Scott |
| 2024/0033148 A1 | 2/2024 | Gordon et al. |
| 2024/0041638 A1 | 2/2024 | Johannes et al. |
| 2024/0058160 A1 | 2/2024 | Young Joyner et al. |
| 2024/0058161 A1 | 2/2024 | Ulreich et al. |
| 2024/0058520 A1 | 2/2024 | Mn et al. |
| 2024/0065881 A1 | 2/2024 | Kuroda et al. |
| 2024/0082044 A1 | 3/2024 | Nguyen et al. |
| 2024/0099874 A1 | 3/2024 | Sanchez et al. |
| 2024/0108268 A1 | 4/2024 | Woodard et al. |
| 2024/0110318 A1 | 4/2024 | Bendt et al. |
| 2024/0122773 A1 | 4/2024 | Nguyen et al. |
| 2024/0123134 A1 | 4/2024 | Kharkar et al. |
| 2024/0148539 A1 | 5/2024 | Austermann et al. |
| 2024/0156633 A1 | 5/2024 | Fallows et al. |
| 2024/0252343 A1 | 8/2024 | Voda |
| 2024/0261131 A1 | 8/2024 | Garvey et al. |
| 2024/0268986 A1 | 8/2024 | Barnes et al. |
| 2024/0268989 A1 | 8/2024 | Martin et al. |
| 2024/0269027 A1 | 8/2024 | Tourchak et al. |
| 2024/0285425 A1 | 8/2024 | Donohoe et al. |
| 2024/0325190 A1 | 10/2024 | Minchew et al. |
| 2024/0358539 A1 | 10/2024 | Gallup |
| 2024/0358542 A1 | 10/2024 | Richardson et al. |
| 2024/0374414 A1 | 11/2024 | Richardson et al. |
| 2025/0009552 A1 | 1/2025 | Blabas et al. |
| 2025/0073055 A1 | 3/2025 | Ecklund et al. |
| 2025/0107920 A1 | 4/2025 | Fallows et al. |
| 2025/0107921 A1 | 4/2025 | Sanchez et al. |

FOREIGN PATENT DOCUMENTS

| | | |
|---|---|---|
| AU | 2022349367 A1 | 4/2024 |
| CA | 2165286 C | 9/1999 |
| CA | 2354132 A1 | 6/2000 |
| CA | 2359091 C | 9/2003 |
| CA | 2488867 C | 8/2007 |
| CA | 3050918 A1 | 8/2018 |
| CA | 3098571 A1 | 11/2019 |
| CA | 3188651 A1 | 7/2023 |
| CN | 2269203 Y | 12/1997 |
| CN | 1332620 A | 1/2002 |
| CN | 1434693 A | 8/2003 |
| CN | 1533755 A | 10/2004 |
| CN | 1602825 A | 4/2005 |
| CN | 1720888 A | 1/2006 |
| CN | 2936204 Y | 8/2007 |
| CN | 101262836 A | 9/2008 |
| CN | 101522148 A | 9/2009 |
| CN | 102159159 A | 8/2011 |
| CN | 202184840 U | 4/2012 |
| CN | 102481441 A | 5/2012 |
| CN | 202463712 U | 10/2012 |
| CN | 202950810 U | 5/2013 |
| CN | 103533968 A | 1/2014 |
| CN | 103717180 A | 4/2014 |
| CN | 204562697 U | 8/2015 |
| CN | 105411783 A | 3/2016 |
| CN | 105451693 A | 3/2016 |
| CN | 105534632 A | 5/2016 |
| CN | 106132360 A | 11/2016 |
| CN | 205849719 U | 1/2017 |
| CN | 205924282 U | 2/2017 |
| CN | 106726089 A | 5/2017 |
| CN | 107847384 A | 3/2018 |
| CN | 107920912 A | 4/2018 |
| CN | 108420590 A | 8/2018 |
| CN | 209285902 U | 8/2019 |
| CN | 110381883 A | 10/2019 |
| CN | 211198839 U | 8/2020 |
| CN | 111991136 A | 11/2020 |
| CN | 112022488 A | 12/2020 |
| CN | 212234893 U | 12/2020 |
| CN | 212466312 U | 2/2021 |
| CN | 112566550 A | 3/2021 |

(56) References Cited

FOREIGN PATENT DOCUMENTS

| | | | |
|---|---|---|---|
| CN | 112603184 | A | 4/2021 |
| CN | 213490035 | U | 6/2021 |
| CN | 114007493 | A | 2/2022 |
| CN | 114375187 | A | 4/2022 |
| CN | 116096332 | A | 5/2023 |
| DE | 79818 | C | 10/1893 |
| DE | 1516466 | A1 | 6/1969 |
| DE | 2721330 | A1 | 11/1977 |
| DE | 2742298 | A1 | 3/1978 |
| DE | 9407554.9 | U1 | 5/1995 |
| DE | 4443710 | A1 | 6/1995 |
| DE | 4416094 | A1 | 11/1995 |
| DE | 4236097 | C2 | 10/1996 |
| DE | 19619597 | A1 | 11/1997 |
| DE | 102005037762 | B3 | 9/2006 |
| DE | 102011103783 | A1 | 12/2012 |
| DE | 102012112818 | A1 | 6/2014 |
| DE | 202015104597 | U1 | 7/2016 |
| DE | 102020121462 | B3 | 1/2022 |
| DK | 9600118 | | 11/1996 |
| EP | 0032138 | A2 | 7/1981 |
| EP | 0066070 | B1 | 12/1982 |
| EP | 0068712 | A1 | 1/1983 |
| EP | 0140470 | A1 | 5/1985 |
| EP | 0220962 | A1 | 5/1987 |
| EP | 0140471 | B1 | 5/1988 |
| EP | 0274753 | A2 | 7/1988 |
| EP | 0119143 | B1 | 11/1988 |
| EP | 0483592 | A1 | 5/1992 |
| EP | 0483730 | A1 | 5/1992 |
| EP | 0610638 | A1 | 8/1994 |
| EP | 0613355 | A1 | 9/1994 |
| EP | 0613355 | B1 | 1/1997 |
| EP | 0787472 | A1 | 8/1997 |
| EP | 0966936 | A1 | 12/1999 |
| EP | 0987293 | A1 | 3/2000 |
| EP | 1063953 | A1 | 1/2001 |
| EP | 0653928 | B1 | 10/2002 |
| EP | 1332738 | A1 | 8/2003 |
| EP | 1382318 | A1 | 1/2004 |
| EP | 1089684 | B1 | 10/2004 |
| EP | 1616542 | A1 | 1/2006 |
| EP | 1382318 | B1 | 5/2006 |
| EP | 1063953 | B1 | 1/2007 |
| EP | 1658831 | B1 | 1/2008 |
| EP | 1872752 | A1 | 1/2008 |
| EP | 2180907 | A1 | 5/2010 |
| EP | 2380532 | A1 | 10/2011 |
| EP | 2389908 | A1 | 11/2011 |
| EP | 2601916 | A1 | 6/2013 |
| EP | 2676643 | A1 | 12/2013 |
| EP | 2997950 | A2 | 3/2016 |
| EP | 2879534 | B1 | 3/2017 |
| EP | 3424471 | A1 | 1/2019 |
| EP | 3169292 | B1 | 11/2019 |
| EP | 3753492 | A1 | 12/2020 |
| EP | 3788992 | A1 | 3/2021 |
| EP | 3576689 | B1 | 3/2022 |
| EP | 3752110 | B1 | 3/2022 |
| EP | 3787570 | B1 | 3/2022 |
| EP | 4025163 | A1 | 7/2022 |
| EP | 3463180 | B1 | 3/2023 |
| EP | 3569205 | B1 | 6/2023 |
| EP | 4382082 | A2 | 6/2024 |
| EP | 4445881 | A2 | 10/2024 |
| EP | 4464288 | A2 | 11/2024 |
| EP | 4527361 | A2 | 3/2025 |
| FR | 2826704 | A1 | 1/2003 |
| GB | 871820 | A | 7/1961 |
| GB | 873045 | A | 7/1961 |
| GB | 1011517 | A | 12/1965 |
| GB | 1467144 | A | 3/1977 |
| GB | 2106395 | A | 4/1983 |
| GB | 2106784 | A | 4/1983 |
| GB | 2148126 | A | 5/1985 |
| GB | 2171315 | A | 8/1986 |
| GB | 2181953 | A | 5/1987 |
| GB | 2148126 | B | 7/1987 |
| GB | 2191095 | A | 12/1987 |
| GB | 2199750 | A | 7/1988 |
| GB | 2260907 | A | 5/1993 |
| GB | 2462267 | A | 2/2010 |
| GB | 2469496 | A | 10/2010 |
| GB | 2490327 | A | 10/2012 |
| GB | 2507318 | A | 4/2014 |
| GB | 2612752 | A | 5/2023 |
| IT | 201800009129 | A1 | 4/2020 |
| JP | S498638 | U | 1/1974 |
| JP | S5410596 | A | 1/1979 |
| JP | S5410596 | Y2 | 5/1979 |
| JP | S54155729 | U | 10/1979 |
| JP | S55155618 | A | 12/1980 |
| JP | S57142534 | U | 9/1982 |
| JP | S5888596 | U | 6/1983 |
| JP | S58188016 | U | 12/1983 |
| JP | S63107780 | U | 7/1988 |
| JP | H0267530 | A | 3/1990 |
| JP | H02103871 | A | 4/1990 |
| JP | H02131422 | A | 5/1990 |
| JP | H02131422 | U | 11/1990 |
| JP | H0460220 | A | 2/1992 |
| JP | H05123349 | A | 5/1993 |
| JP | H05123350 | A | 5/1993 |
| JP | H0626264 | U | 4/1994 |
| JP | 3087938 | B2 | 10/1995 |
| JP | H085630 | A | 1/1996 |
| JP | H1040141 | A | 2/1998 |
| JP | H10225430 | A | 8/1998 |
| JP | H11113946 | A | 4/1999 |
| JP | H11290365 | A | 10/1999 |
| JP | 2000116690 | A | 4/2000 |
| JP | 2000185068 | A | 7/2000 |
| JP | 2000225139 | A | 8/2000 |
| JP | 2001054531 | A | 2/2001 |
| JP | 2001070331 | A | 3/2001 |
| JP | 2001224616 | A | 8/2001 |
| JP | 2001276107 | A | 10/2001 |
| JP | 2001276108 | A | 10/2001 |
| JP | 2002028173 | A | 1/2002 |
| JP | 2003038563 | A | 2/2003 |
| JP | 2003505152 | A | 2/2003 |
| JP | 2003126242 | A | 5/2003 |
| JP | 2003180722 | A | 7/2003 |
| JP | 2003528691 | A | 9/2003 |
| JP | 2004057578 | A | 2/2004 |
| JP | 2004130056 | A | 4/2004 |
| JP | 2004267530 | A | 9/2004 |
| JP | 2005052219 | A | 3/2005 |
| JP | 2005066011 | A | 3/2005 |
| JP | 2005066325 | A | 3/2005 |
| JP | 2005102978 | A | 4/2005 |
| JP | 2005518237 | A | 6/2005 |
| JP | 2005518901 | A | 6/2005 |
| JP | 3749097 | B2 | 12/2005 |
| JP | 2006026108 | A | 2/2006 |
| JP | 3123547 | B2 | 6/2006 |
| JP | 2006136492 | A | 6/2006 |
| JP | 2006204868 | A | 8/2006 |
| JP | 2007044494 | A | 2/2007 |
| JP | 3132659 | B2 | 5/2007 |
| JP | 2007209687 | A | 8/2007 |
| JP | 2007259898 | A | 10/2007 |
| JP | 4039641 | B2 | 11/2007 |
| JP | 2008005975 | A | 1/2008 |
| JP | 2009509570 | A | 3/2009 |
| JP | 2009165887 | A | 7/2009 |
| JP | 2009525776 | A | 7/2009 |
| JP | 2010504150 | A | 2/2010 |
| JP | 2010058795 | A | 3/2010 |
| JP | 2010081981 | A | 4/2010 |
| JP | 2010166954 | A | 8/2010 |
| JP | 4640772 | B2 | 12/2010 |
| JP | 2010536439 | A | 12/2010 |
| JP | 2011500225 | A | 1/2011 |

(56) References Cited

FOREIGN PATENT DOCUMENTS

| | | | |
|---|---|---|---|
| JP | 2011030962 A | | 2/2011 |
| JP | 4747166 B2 | | 5/2011 |
| JP | 2011087823 A | | 5/2011 |
| JP | 4801218 B1 | | 8/2011 |
| JP | 2011218130 A | | 11/2011 |
| JP | 2011224070 A | | 11/2011 |
| JP | 3175719 U | | 4/2012 |
| JP | 2012523869 A | | 10/2012 |
| JP | 2013238608 A | | 11/2013 |
| JP | 2014521960 A | | 8/2014 |
| JP | 2015092945 A | | 5/2015 |
| JP | 2015513678 A | | 5/2015 |
| JP | 3198994 B2 | | 7/2015 |
| JP | 2015221390 A | | 12/2015 |
| JP | 2016521191 A | | 7/2016 |
| JP | 2017014698 A | | 1/2017 |
| JP | 2017070400 A | | 4/2017 |
| JP | 2017512603 A | | 5/2017 |
| JP | 2017201272 A | | 11/2017 |
| JP | 2019010375 A | | 1/2019 |
| JP | 2019076342 A | | 5/2019 |
| JP | 2019525811 A | | 9/2019 |
| JP | 2019170942 A | | 10/2019 |
| JP | 2019533492 A | | 11/2019 |
| JP | 2020520775 A | | 7/2020 |
| JP | 2021007472 A | | 1/2021 |
| JP | 2021120686 A | | 8/2021 |
| JP | 2021522009 A | | 8/2021 |
| JP | 2021522013 A | | 8/2021 |
| JP | 7129493 B2 | | 8/2022 |
| JP | 2023532132 A | | 7/2023 |
| KR | 200290061 Y1 | | 9/2002 |
| KR | 20030047451 A | | 6/2003 |
| KR | 20080005516 A | | 1/2008 |
| KR | 20090072069 A | | 7/2009 |
| KR | 20090104426 A | | 10/2009 |
| KR | 20090110359 A | | 10/2009 |
| KR | 20120005922 A | | 1/2012 |
| KR | 20140039485 A | | 4/2014 |
| KR | 101432639 B1 | | 8/2014 |
| KR | 20180106659 A | | 10/2018 |
| KR | 20180108774 A | | 10/2018 |
| KR | 20230034343 A | | 3/2023 |
| NO | 2022076427 A2 | | 4/2022 |
| PT | 2068717 E | | 6/2013 |
| SE | 505542 C2 | | 9/1997 |
| WO | 8101957 A1 | | 7/1981 |
| WO | 8804558 A1 | | 6/1988 |
| WO | 9104714 A2 | | 4/1991 |
| WO | 9104714 A3 | | 6/1991 |
| WO | 9220299 A3 | | 2/1993 |
| WO | 9303690 A1 | | 3/1993 |
| WO | 9307839 A1 | | 4/1993 |
| WO | 9309736 A2 | | 5/1993 |
| WO | 9309736 A3 | | 6/1993 |
| WO | 9514448 A2 | | 6/1995 |
| WO | 9600096 A1 | | 1/1996 |
| WO | 9634636 A1 | | 11/1996 |
| WO | 9817211 A1 | | 4/1998 |
| WO | 9830336 A1 | | 7/1998 |
| WO | 0000112 A1 | | 1/2000 |
| WO | 0000113 A1 | | 1/2000 |
| WO | 0025651 A1 | | 5/2000 |
| WO | 0033773 A1 | | 6/2000 |
| WO | 0057784 A1 | | 10/2000 |
| WO | 0069377 A1 | | 11/2000 |
| WO | 0079497 A1 | | 12/2000 |
| WO | 0145618 A1 | | 6/2001 |
| WO | 0145621 A1 | | 6/2001 |
| WO | 02094160 A1 | | 11/2002 |
| WO | 03013967 A1 | | 2/2003 |
| WO | 03024824 A1 | | 3/2003 |
| WO | 03055423 A1 | | 7/2003 |
| WO | 03071931 A2 | | 9/2003 |
| WO | 03079942 A1 | | 10/2003 |
| WO | 03071931 A3 | | 2/2004 |
| WO | 2004019836 A1 | | 3/2004 |
| WO | 2004024046 A1 | | 3/2004 |
| WO | 2004026195 A1 | | 4/2004 |
| WO | 2005051252 A1 | | 6/2005 |
| WO | 2005060558 A2 | | 7/2005 |
| WO | 2005074571 A3 | | 9/2005 |
| WO | 2005089687 A2 | | 9/2005 |
| WO | 2005107661 A2 | | 11/2005 |
| WO | 2006021220 A1 | | 3/2006 |
| WO | 2006037140 A2 | | 4/2006 |
| WO | 2007005851 A2 | | 1/2007 |
| WO | 2007007845 A1 | | 1/2007 |
| WO | 2007042823 A2 | | 4/2007 |
| WO | 2007055651 A1 | | 5/2007 |
| WO | 2006098950 A3 | | 11/2007 |
| WO | 2007134608 A2 | | 11/2007 |
| WO | 2007128156 A3 | | 2/2008 |
| WO | 2008026106 A2 | | 3/2008 |
| WO | 2008078117 A1 | | 7/2008 |
| WO | 2008104019 A1 | | 9/2008 |
| WO | 2008141471 A1 | | 11/2008 |
| WO | 2009004368 A1 | | 1/2009 |
| WO | 2009004369 A1 | | 1/2009 |
| WO | 2009052496 A1 | | 4/2009 |
| WO | 2009052502 A1 | | 4/2009 |
| WO | 2009007702 A4 | | 7/2009 |
| WO | 2009101738 A1 | | 8/2009 |
| WO | 2010058192 A1 | | 5/2010 |
| WO | 2010030122 A3 | | 7/2010 |
| WO | 2010101915 A3 | | 1/2011 |
| WO | 2011018132 A1 | | 2/2011 |
| WO | 2011018133 A1 | | 2/2011 |
| WO | 2011024864 A1 | | 3/2011 |
| WO | 2011054118 A1 | | 5/2011 |
| WO | 2011079132 A1 | | 6/2011 |
| WO | 2011107972 A1 | | 9/2011 |
| WO | 2011108972 A1 | | 9/2011 |
| WO | 2011117292 A1 | | 9/2011 |
| WO | 2011123219 A1 | | 10/2011 |
| WO | 2011132043 A1 | | 10/2011 |
| WO | 2012012908 A1 | | 2/2012 |
| WO | 2012020506 A1 | | 2/2012 |
| WO | 2012065274 A1 | | 5/2012 |
| WO | 2012097462 A1 | | 7/2012 |
| WO | 2012098796 A1 | | 7/2012 |
| WO | 2012101288 A1 | | 8/2012 |
| WO | 2012175916 A1 | | 12/2012 |
| WO | 2013018435 A1 | | 2/2013 |
| WO | 2013033429 A1 | | 3/2013 |
| WO | 2013055434 A1 | | 4/2013 |
| WO | 2013082397 A1 | | 6/2013 |
| WO | 2013103291 A2 | | 7/2013 |
| WO | 2013131109 A1 | | 9/2013 |
| WO | 2013167478 A1 | | 11/2013 |
| WO | 2013177716 A1 | | 12/2013 |
| WO | 2014041534 A1 | | 3/2014 |
| WO | 2014046420 A1 | | 3/2014 |
| WO | 2014118518 A1 | | 8/2014 |
| WO | 2014160852 A1 | | 10/2014 |
| WO | 2015023599 A1 | | 2/2015 |
| WO | 2015052348 A1 | | 4/2015 |
| WO | 2015068384 A1 | | 5/2015 |
| WO | 2015169403 A1 | | 11/2015 |
| WO | 2015170307 A1 | | 11/2015 |
| WO | 2015197462 A1 | | 12/2015 |
| WO | 2016051385 A1 | | 4/2016 |
| WO | 2016055989 A1 | | 4/2016 |
| WO | 2016071894 A1 | | 5/2016 |
| WO | 2016103242 A1 | | 6/2016 |
| WO | 2016116915 A1 | | 7/2016 |
| WO | 2016124203 A1 | | 8/2016 |
| WO | 2016139448 A1 | | 9/2016 |
| WO | 2016166562 A1 | | 10/2016 |
| WO | 2016167535 A1 | | 10/2016 |
| WO | 2016191574 A1 | | 12/2016 |
| WO | 2016200088 A1 | | 12/2016 |
| WO | 2016200361 A1 | | 12/2016 |
| WO | 2016204731 A1 | | 12/2016 |

(56) References Cited

FOREIGN PATENT DOCUMENTS

| | | | |
|---|---|---|---|
| WO | 2017001532 | A2 | 1/2017 |
| WO | 2017001846 | A1 | 1/2017 |
| WO | 2017075226 | A1 | 5/2017 |
| WO | 2017152198 | A1 | 9/2017 |
| WO | 2017153357 | A1 | 9/2017 |
| WO | 2017162559 | A1 | 9/2017 |
| WO | 2017205446 | A1 | 11/2017 |
| WO | 2017209779 | A1 | 12/2017 |
| WO | 2017210524 | A1 | 12/2017 |
| WO | 2018022414 | A1 | 2/2018 |
| WO | 2018044781 | A1 | 3/2018 |
| WO | 2018056953 | A1 | 3/2018 |
| WO | 2018090550 | A1 | 5/2018 |
| WO | 2018138513 | A1 | 8/2018 |
| WO | 2018144318 | A1 | 8/2018 |
| WO | 2018144463 | A1 | 8/2018 |
| WO | 2018150263 | A1 | 8/2018 |
| WO | 2018150268 | A1 | 8/2018 |
| WO | 2018152156 | A1 | 8/2018 |
| WO | 2018183791 | A1 | 10/2018 |
| WO | 2018150267 | A3 | 11/2018 |
| WO | 2018235026 | A1 | 12/2018 |
| WO | 2018235065 | A1 | 12/2018 |
| WO | 2019004404 | A1 | 1/2019 |
| WO | 2019041005 | A1 | 3/2019 |
| WO | 2019044217 | A1 | 3/2019 |
| WO | 2019044218 | A1 | 3/2019 |
| WO | 2019044219 | A1 | 3/2019 |
| WO | 2019050959 | A1 | 3/2019 |
| WO | 2019065541 | A1 | 4/2019 |
| WO | 2019096845 | A1 | 5/2019 |
| WO | 2019150385 | A1 | 8/2019 |
| WO | 2019161094 | A1 | 8/2019 |
| WO | 2019188566 | A1 | 10/2019 |
| WO | 2019190593 | A1 | 10/2019 |
| WO | 2019212949 | A1 | 11/2019 |
| WO | 2019212950 | A1 | 11/2019 |
| WO | 2019212951 | A1 | 11/2019 |
| WO | 2019212952 | A1 | 11/2019 |
| WO | 2019212954 | A1 | 11/2019 |
| WO | 2019212955 | A1 | 11/2019 |
| WO | 2019212956 | A1 | 11/2019 |
| WO | 2019214787 | A1 | 11/2019 |
| WO | 2019214788 | A1 | 11/2019 |
| WO | 2019226826 | A1 | 11/2019 |
| WO | 2019239433 | A1 | 12/2019 |
| WO | 2020000994 | A1 | 1/2020 |
| WO | 2020020618 | A1 | 1/2020 |
| WO | 2020033752 | A1 | 2/2020 |
| WO | 2020038822 | A1 | 2/2020 |
| WO | 2020088409 | A1 | 5/2020 |
| WO | 2020049394 | A3 | 6/2020 |
| WO | 2020120657 | A1 | 6/2020 |
| WO | 2020152575 | A1 | 7/2020 |
| WO | 2020182923 | A1 | 9/2020 |
| WO | 2020204967 | A1 | 10/2020 |
| WO | 2020205939 | A1 | 10/2020 |
| WO | 2020209898 | A1 | 10/2020 |
| WO | 2020242790 | A1 | 12/2020 |
| WO | 2020251893 | A1 | 12/2020 |
| WO | 2020256865 | A1 | 12/2020 |
| WO | 2021007144 | A1 | 1/2021 |
| WO | 2021007345 | A1 | 1/2021 |
| WO | 2021010844 | A1 | 1/2021 |
| WO | 2021016026 | A1 | 1/2021 |
| WO | 2021016056 | A1 | 1/2021 |
| WO | 2021016300 | A1 | 1/2021 |
| WO | 2021025919 | A1 | 2/2021 |
| WO | 2021034886 | A1 | 2/2021 |
| WO | 2021041123 | A1 | 3/2021 |
| WO | 2021046501 | A1 | 3/2021 |
| WO | 2021086868 | A1 | 5/2021 |
| WO | 2021094352 | A1 | 5/2021 |
| WO | 2021094639 | A1 | 5/2021 |
| WO | 2021097067 | A1 | 5/2021 |
| WO | 2021102296 | A1 | 5/2021 |
| WO | 2021107025 | A1 | 6/2021 |
| WO | 2021138411 | A1 | 7/2021 |
| WO | 2021138414 | A1 | 7/2021 |
| WO | 2021154686 | A1 | 8/2021 |
| WO | 2021155206 | A1 | 8/2021 |
| WO | 2021170075 | A1 | 9/2021 |
| WO | 2021173436 | A1 | 9/2021 |
| WO | 2021188817 | A1 | 9/2021 |
| WO | 2021195384 | A1 | 9/2021 |
| WO | 2021205995 | A1 | 10/2021 |
| WO | 2021207621 | A1 | 10/2021 |
| WO | 2021211568 | A1 | 10/2021 |
| WO | 2021211801 | A1 | 10/2021 |
| WO | 2021211914 | A1 | 10/2021 |
| WO | 2021216419 | A1 | 10/2021 |
| WO | 2021216422 | A1 | 10/2021 |
| WO | 2021231532 | A1 | 11/2021 |
| WO | 2021247523 | A1 | 12/2021 |
| WO | 2021257202 | A1 | 12/2021 |
| WO | 2022006256 | A1 | 1/2022 |
| WO | 2022029662 | A1 | 2/2022 |
| WO | 2022031943 | A1 | 2/2022 |
| WO | 2022035745 | A1 | 2/2022 |
| WO | 2022051220 | A1 | 3/2022 |
| WO | 2022051360 | A1 | 3/2022 |
| WO | 2022054613 | A1 | 3/2022 |
| WO | 2022066704 | A1 | 3/2022 |
| WO | 2022067392 | A1 | 4/2022 |
| WO | 2022069950 | A1 | 4/2022 |
| WO | 2022071429 | A1 | 4/2022 |
| WO | 2022076322 | A1 | 4/2022 |
| WO | 2022086898 | A1 | 4/2022 |
| WO | 2022090199 | A1 | 5/2022 |
| WO | 2022098536 | A1 | 5/2022 |
| WO | 2022099087 | A1 | 5/2022 |
| WO | 2022101999 | A1 | 5/2022 |
| WO | 2022115692 | A1 | 6/2022 |
| WO | 2022125685 | A1 | 6/2022 |
| WO | 2022140545 | A1 | 6/2022 |
| WO | 2022145231 | A1 | 7/2022 |
| WO | 2022150290 | A1 | 7/2022 |
| WO | 2022150360 | A1 | 7/2022 |
| WO | 2022150463 | A1 | 7/2022 |
| WO | 2022159392 | A1 | 7/2022 |
| WO | 2022170182 | A1 | 8/2022 |
| WO | 2022173803 | A1 | 8/2022 |
| WO | 2022182385 | A1 | 9/2022 |
| WO | 2022187152 | A1 | 9/2022 |
| WO | 2022192188 | A1 | 9/2022 |
| WO | 2022192347 | A1 | 9/2022 |
| WO | 2022204000 | A1 | 9/2022 |
| WO | 2022216507 | A1 | 10/2022 |
| WO | 2022216776 | A1 | 10/2022 |
| WO | 2022222030 | A1 | 10/2022 |
| WO | 2022251184 | A1 | 12/2022 |
| WO | 2022251425 | A1 | 12/2022 |
| WO | 2022271783 | A1 | 12/2022 |
| WO | 2023286058 | A1 | 1/2023 |
| WO | 2023014639 | A1 | 2/2023 |
| WO | 2023014641 | A1 | 2/2023 |
| WO | 2023018475 | A2 | 2/2023 |
| WO | 2023018656 | A1 | 2/2023 |
| WO | 2023018657 | A1 | 2/2023 |
| WO | 2023023777 | A1 | 3/2023 |
| WO | 2023034139 | A1 | 3/2023 |
| WO | 2023034453 | A1 | 3/2023 |
| WO | 2023038945 | A1 | 3/2023 |
| WO | 2023038950 | A1 | 3/2023 |
| WO | 2023049109 | A1 | 3/2023 |
| WO | 2023049156 | A1 | 3/2023 |
| WO | 2023049175 | A1 | 3/2023 |
| WO | 2023086394 | A1 | 5/2023 |
| WO | 2023149884 | A1 | 8/2023 |
| WO | 2023149902 | A1 | 8/2023 |
| WO | 2023149903 | A1 | 8/2023 |
| WO | 2023154390 | A1 | 8/2023 |
| WO | 2023163725 | A1 | 8/2023 |
| WO | 2023191764 | A1 | 10/2023 |

(56) References Cited

FOREIGN PATENT DOCUMENTS

| WO | 2023244238 A1 | 12/2023 |
| WO | 2024043871 A1 | 2/2024 |
| WO | 2024058788 A1 | 3/2024 |
| WO | 2024253655 A1 | 12/2024 |
| WO | 2025034959 A1 | 2/2025 |
| WO | 2025038087 A1 | 2/2025 |
| WO | 2025038088 A1 | 2/2025 |
| WO | 2025071622 A1 | 4/2025 |

OTHER PUBLICATIONS

Advisory Action for U.S. Appl. No. 16/452,258 mailed Oct. 26, 2022.
Advisory Action for U.S. Appl. No. 16/478,180 mailed Sep. 21, 2022.
Final Office Action for U.S. Appl. No. 16/245,726 mailed Nov. 25, 2022.
Final Office Action for U.S. Appl. No. 16/369,676 mailed Dec. 5, 2022.
Final Office Action for U.S. Appl. No. 16/433,773 mailed Oct. 25, 2022.
Final Office Action for U.S. Appl. No. 17/662,700 mailed Sep. 30, 2022.
International Search Report and Written Opinion from International Application No. PCT/IB2021/057173 mailed Nov. 5, 2021.
International Search Report and Written Opinion from International Application No. PCT/US2021/039866 mailed Oct. 7, 2021.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418_mailed Nov. 11, 2022.
International Search Report and Written Opinion from International Application No. PCT/US2022/015781 mailed May 6, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/034457 mailed Oct. 12, 2022.
Issue Notification for U.S. Appl. No. 16,905,400 mailed Nov. 30, 2022.
Non-Final Office Action for U.S. Appl. No. 17/451,345 mailed Dec. 7, 2022.
Notice of Allowance for U.S. Appl. No. 16/899,956 mailed Dec. 1, 2022.
Notice of Allowance for U.S. Appl. No. 17/461,036 mailed Oct. 6, 2022.
U.S. Appl. No. 17/907,125, filed Sep. 23, 2022.
U.S. Appl. No. 17/912,147, filed Sep. 16, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 17/999,648, filed Nov. 22, 2022.
U.S. Appl. No. 62/991,754, filed Mar. 19, 2020.

Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/904,868 mailed Jun. 15, 2022.
Advisory Action for U.S. Appl. No. 16/905,400 mailed Feb. 16, 2022.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Corrected Notice of Allowability for U.S. Appl. No. 17/330,657 mailed Dec. 9, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/449,039 mailed Aug. 1, 2022.
Final Office Action for U.S. Appl. No. 16/452,145 mailed Mar. 25, 2022.
Final Office Action for U.S. Appl. No. 16/452,258 mailed Jun. 14, 2022.
Final Office Action for U.S. Appl. No. 16/478,180 mailed Jun. 22, 2022.
Final Office Action for U.S. Appl. No. 16/899,956 mailed Apr. 19, 2021.
Final Office Action for U.S. Appl. No. 16/904,868 mailed Mar. 10, 2022.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 16/905,400 mailed Dec. 9, 2021.
Final Office Action for U.S. Appl. No. 17/088,272 mailed May 25, 2021.
Final Office Action for U.S. Appl. No. 29/624,661 mailed Feb. 18, 2020.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.

(56)　　　　　References Cited

OTHER PUBLICATIONS

International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/057562 mailed Jan. 27, 2021.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/026607 mailed Jul. 29, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.

International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/035181 mailed Sep. 16, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/015471 mailed May 16, 2022.
International Search Report and Written Opinion from International Application No. PCT/US2022/015492 mailed Apr. 26, 2022.
International Search Report and Written Opinion from International Application No. PCT/US2022/016942 mailed Jun. 8, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 17/088,272 mailed Jun. 15, 2022.

(56)        References Cited

OTHER PUBLICATIONS

Issue Notification for U.S. Appl. No. 17/330,657 mailed Jun. 22, 2022.

Issue Notification for U.S. Appl. No. 29/624,661 mailed Aug. 4, 2021.

Non-Final Office Action for U.S. Appl. No. 14/592,591 mailed Mar. 20, 2020.

Non-Final Office Action for U.S. Appl. No. 14/722,613 mailed Jun. 13, 2019.

Non-Final Office Action for U.S. Appl. No. 14/947,759 mailed Mar. 17, 2016.

Non-Final Office Action for U.S. Appl. No. 14/952,591 mailed Aug. 1, 2017.

Non-Final Office Action for U.S. Appl. No. 14/952,591 mailed Mar. 20, 2020.

Non-Final Office Action for U.S. Appl. No. 14/952,591 mailed Mar. 21, 2019.

Non-Final Office Action for U.S. Appl. No. 14/952,591 mailed Sep. 28, 2018.

Non-Final Office Action for U.S. Appl. No. 15/171,968 mailed May 11, 2020.

Non-Final Office Action for U.S. Appl. No. 15/171,968 mailed Aug. 20, 2019.

Non-Final Office Action for U.S. Appl. No. 15/171,968 mailed Jun. 12, 2018.

Non-Final Office Action for U.S. Appl. No. 15/221,106 mailed Jun. 5, 2018.

Non-Final Office Action for U.S. Appl. No. 15/238,427 mailed Aug. 8, 2018.

Non-Final Office Action for U.S. Appl. No. 15/260,103 mailed Sep. 26, 2018.

Non-Final Office Action for U.S. Appl. No. 15/611,587 mailed Dec. 29, 2017.

Non-Final Office Action for U.S. Appl. No. 15/611,587 mailed Jul. 13, 2018.

Non-Final Office Action for U.S. Appl. No. 15/612,325 mailed Mar. 19, 2020.

Non-Final Office Action for U.S. Appl. No. 16/245,726 mailed Jan. 21, 2022.

Non-Final Office Action for U.S. Appl. No. 16/369,676 mailed Mar. 31, 2022.

Non-Final Office Action for U.S. Appl. No. 16/433,773 mailed Apr. 21, 2022.

Non-Final Office Action for U.S. Appl. No. 16/449,039 mailed Dec. 8, 2021.

Non-Final Office Action for U.S. Appl. No. 16/452,145 mailed Sep. 28, 2021.

Non-Final Office Action for U.S. Appl. No. 16/452,258 mailed Sep. 28, 2021.

Non-Final Office Action for U.S. Appl. No. 16/478,180 mailed Oct. 22, 2021.

Non-Final Office Action for U.S. Appl. No. 16/899,956 mailed Oct. 16, 2020.

Non-Final Office Action for U.S. Appl. No. 16/899,956 mailed Sep. 2, 2021.

Non-Final Office Action for U.S. Appl. No. 16/904,868 mailed Nov. 25, 2020.

Non-Final Office Action for U.S. Appl. No. 16/904,868 mailed Oct. 5, 2021.

Non-Final Office Action for U.S. Appl. No. 16/905,400 mailed Apr. 27, 2022.

Non-Final Office Action for U.S. Appl. No. 16/905,400 mailed Dec. 2, 2020.

Non-Final Office Action for U.S. Appl. No. 16/905,400 mailed Jul. 22, 2021.

Non-Final Office Action for U.S. Appl. No. 17/088,272 mailed Jan. 25, 2021.

Non-Final Office Action for U.S. Appl. No. 17/330,657 mailed Aug. 11, 2021.

Non-Final Office Action for U.S. Appl. No. 17/662,700 mailed Jul. 22, 2022.

Non-Final Office Action for U.S. Appl. No. 29/624,661 mailed Jul. 18, 2019.

Non-Final Office Action for U.S. Appl. No. 29/694,002 mailed Jun. 24, 2020.

Non-Final Office Action for U.S. Appl. No. 29/741,751 mailed Jan. 18, 2022.

Notice of Allowance for U.S. Appl. No. 14/952,591 mailed Apr. 5, 2021.

Notice of Allowance for U.S. Appl. No. 14/952,591 mailed Jul. 8, 2021.

Notice of Allowance for U.S. Appl. No. 15/171,968 mailed Feb. 16, 2021.

Notice of Allowance for U.S. Appl. No. 15/171,968 mailed Nov. 6, 2020.

Notice of Allowance for U.S. Appl. No. 15/221,106 mailed May 1, 2019.

Notice of Allowance for U.S. Appl. No. 15/238,427 mailed May 23, 2019.

Notice of Allowance for U.S. Appl. No. 15/260,103 mailed Jun. 7, 2019.

Notice of Allowance for U.S. Appl. No. 15/611,587 mailed Dec. 21, 2018.

Notice of Allowance for U.S. Appl. No. 15/612,325 mailed Feb. 19, 2021.

Notice of Allowance for U.S. Appl. No. 15/612,325 mailed Jan. 21, 2021.

Notice of Allowance for U.S. Appl. No. 16/899,956 mailed Apr. 19, 2022.

Notice of Allowance for U.S. Appl. No. 16/899,956 mailed Aug. 10, 2022.

Notice of Allowance for U.S. Appl. No. 16/899,956 mailed Dec. 29, 2021.

Notice of Allowance for U.S. Appl. No. 16/905,400 mailed Aug. 17, 2022.

Notice of Allowance for U.S. Appl. No. 17/088,272 mailed Aug. 5, 2021.

Notice of Allowance for U.S. Appl. No. 17/088,272 mailed Mar. 4, 2022.

Notice of Allowance for U.S. Appl. No. 17/088,272 mailed Nov. 24, 2021.

Notice of Allowance for U.S. Appl. No. 17/330,657 mailed Mar. 16, 2022.

Notice of Allowance for U.S. Appl. No. 17/330,657 mailed Nov. 26, 2021.

Notice of Allowance for U.S. Appl. No. 29/624,661 mailed Apr. 28, 2021.

Notice of Allowance for U.S. Appl. No. 29/624,661 mailed Jul. 10, 2020.

Notice of Allowance for U.S. Appl. No. 29/624,661 mailed May 14, 2020.

Notice of Allowance for U.S. Appl. No. 29/624,661 mailed Sep. 29, 2020.

Notice of Allowance for U.S. Appl. No. 29/694,002 mailed Apr. 29, 2021.

Notice of Allowance for U.S. Appl. No. 29/694,002 mailed Jan. 29, 2021.

Notice of Allowance for U.S. Appl. No. 29/694,002 mailed Oct. 16, 2020.

Notice of Allowance for U.S. Appl. No. 29/741,751 mailed Jun. 9, 2022.

Notice to File Missing Parts for U.S. Appl. No. 17/179,116 mailed Mar. 3, 2021.

Restriction Requirement for U.S. Appl. No. 16/433,773 mailed Dec. 7, 2021.

Restriction Requirement for U.S. Appl. No. 16/478,180 mailed May 25, 2021.

U.S. Appl. No. 14/625,469, filed Feb. 28, 2015.

U.S. Appl. No. 14/947,759, filed Nov. 20, 2015.

U.S. Appl. No. 14/952,591, filed Nov. 25, 2015.

U.S. Appl. No. 15/171,968, filed Jun. 2, 2016.

U.S. Appl. No. 15/221,106, filed Jul. 27, 2016.

(56) References Cited

OTHER PUBLICATIONS

U.S. Appl. No. 15/260,103, filed Sep. 8, 2016.
U.S. Appl. No. 15/384,196, filed Dec. 19, 2016.
U.S. Appl. No. 15/611,587, filed Jun. 1, 2017.
U.S. Appl. No. 15/612,325, filed Jun. 2, 2017.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/494,578, filed Oct. 5, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/654,156, filed Mar. 9, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/929,887, filed Sep. 6, 2022.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.

U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,158, filed Jan. 26, 2020.
U.S. Appl. No. 62/967,977, filed Jan. 30, 2020.
U.S. Appl. No. 62/994,912, filed Mar. 26, 2020.
U.S. Appl. No. 63/008,112, filed Apr. 10, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/094,646, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/146,946, filed Feb. 8, 2021.
U.S. Appl. No. 63/147,013, filed Feb. 8, 2021.

(56)                References Cited

OTHER PUBLICATIONS

U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/159,280, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/191,558, filed May 21, 2021.
U.S. Appl. No. 63/192,274, filed May 24, 2021.
U.S. Appl. No. 63/192,289, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,328, filed Sep. 7, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
Sage's Second Supplemental Invalidity Contentions Regarding U.S. Pat. Nos. 8,287,508, 10,226,375, 10,390,989, and 10,376,407, 292 pages.
Plaintiff's Identification of Claim Terms and Proposed Constructions, 3 pages.
Sage's Preliminary Identification of Claim Elements and Proposed Constructions for U.S. Pat. Nos. 8,287,508, 10,226,376, 10,390,989 and 10,376,407, 7 pages.
Corrected Certificate of Service, 2020, 2 pages.
Excerpts from the 508 (U.S. Pat. No. 8,278,508) Patent's Prosecution History, 2020, 99 pages.
Declaration of Diane K. Newman Curriculum Vitae, 2020, pp. 1-199.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Decision Granting Institution of Inter Partes Review for U.S. Pat. No. 8,287,508, Feb. 17, 2021, 39 pages.
Memorandum Order, Feb. 2021, 14 pgs.
Boehringer CareDry System—Second Generation for Non-Invasive Urinary Management for Females, Mar. 2021, 3 pgs.
PureWick's Response to Interrogatory No. 9 in *PureWick, LLC* v. *Sage Products, LLC*, Mar. 23, 2020, 6 pages.
Sage's Initial Invalidity Contentions Regarding U.S. Pat. Nos. 8,287,508; 10,226,375; and 10,390,989, May 29, 2020, 193 pages.

Defendant and Counterclaim Plaintiff Sage Products, Llc's Answer, Defenses, and Counterclaims to Plaintiff's Amended Complaint, Nov. 1, 2019.
Plaintiff's Opening Claim Construction Brief, Oct. 16, 2020, 26 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Rising Warrior Insulated Gallon Jug Cover", https://www.amazon.com/Rising-Warrior-Insulated-Sleeve, 2021, 2 pages.
"Step by Step How Ur24 WorksHome", http://medicalpatentur24.com, Aug. 30, 2017, 4 pages.
"Underwear that absorbs your period", Thinx!, 7 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"User & Maintenance Guide", Omni Medical, 2007, 16 pages.
"Vinyl Dust Cover, Janome #741811000, Janome, Sewing Parts Online", https://www.sewingpartsonline.com/vinyl-dust-cover-janome-74181000, 2020, 2 pages.
"Winners Announced for Dare-to-Dream Medtech Design Challenge", https://www.mddionline.com/design-engineering/winners-announced-dare-dream-medtech-design-challenge, 2014, 4 pages.
Ali , "Sustainability Assessment: Seventh Generation Diapers versus gDiapers", The University of Vermont, Dec. 6, 2011, pp. 1-31.
Autumn , et al., "Frictional adhesion: a new angle on gecko attachment", The Journal of Experimental Biology, 2006, pp. 3569-3579.
Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Dec. 29, 2023.
Advisory Action for U.S. Appl. No. 16/433,773 mailed Feb. 15, 2023.
Advisory Action for U.S. Appl. No. 16/449,039 mailed Jan. 25, 2024.
Advisory Action for U.S. Appl. No. 16/452,258 mailed Apr. 8, 2024.
Advisory Action for U.S. Appl. No. 16/478,180 mailed Sep. 7, 2023.
Advisory Action for U.S. Appl. No. 16/904,868 mailed Jan. 2, 2024.
Advisory Action for U.S. Appl. No. 17/051,550 mailed Sep. 8, 2023.
Advisory Action for U.S. Appl. No. 17/051,585 mailed Oct. 17, 2023.

(56) References Cited

OTHER PUBLICATIONS

Advisory Action for U.S. Appl. No. 17/179,116 mailed Jan. 8, 2024.
Advisory Action for U.S. Appl. No. 17/444,792 mailed Aug. 25, 2023.
Advisory Action for U.S. Appl. No. 17/446,256 mailed Dec. 8, 2023.
Advisory Action for U.S. Appl. No. 17/446,654 mailed Apr. 15, 2024.
Advisory Action for U.S. Appl. No. 17/448,811 mailed Nov. 15, 2023.
Advisory Action for U.S. Appl. No. 17/450,864 mailed Mar. 21, 2024.
Advisory Action for U.S. Appl. No. 17/451,345 mailed Oct. 20, 2023.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/501,591 mailed Feb. 22, 2024.
Advisory Action for U.S. Appl. No. 17/646,771 mailed Feb. 29, 2024.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 17/661,090 mailed Feb. 26, 2024.
Advisory Action for U.S. Appl. No. 17/662,700 mailed Jan. 30, 2023.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 18/139,523 mailed Apr. 24, 2024.
Advisory Action for U.S. Appl. No. 18/140,751 mailed Apr. 24, 2024.
Advisory Action for U.S. Appl. No. 18/164,800 mailed Feb. 12, 2024.
Communication of Notice of Opposition of European Application No. 17807547.9 mailed Jan. 5, 2024.
Corrected Notice of Allowability for U.S. Appl. No. 16/369,676 mailed Dec. 7, 2023.
Corrected Notice of Allowability for U.S. Appl. No. 17/326,980 mailed Feb. 8, 2024.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Final Office Action for U.S. Appl. No. 16/369,676 mailed Aug. 31, 2023.
Final Office Action for U.S. Appl. No. 16/433,773 mailed Oct. 10, 2023.
Final Office Action for U.S. Appl. No. 16/449,039 mailed Nov. 21, 2023.
Final Office Action for U.S. Appl. No. 16/452,258 mailed Dec. 21, 2023.
Final Office Action for U.S. Appl. No. 16/478,180 mailed Feb. 28, 2024.
Final Office Action for U.S. Appl. No. 16/478,180 mailed May 31, 2023.
Final Office Action for U.S. Appl. No. 16/904,868 mailed Nov. 2, 2023.
Final Office Action for U.S. Appl. No. 17/051,399 mailed Jan. 8, 2024.
Final Office Action for U.S. Appl. No. 17/051,399 mailed Mar. 9, 2023.
Final Office Action for U.S. Appl. No. 17/051,550 mailed May 23, 2023.

Final Office Action for U.S. Appl. No. 17/051,585 mailed Jul. 27, 2023.
Final Office Action for U.S. Appl. No. 17/179,116 mailed Oct. 31, 2023.
Final Office Action for U.S. Appl. No. 17/444,792 mailed Apr. 3, 2024.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/446,654 mailed Jan. 31, 2024.
Final Office Action for U.S. Appl. No. 17/447,123 mailed May 14, 2024.
Final Office Action for U.S. Appl. No. 17/448,811 mailed Aug. 3, 2023.
Final Office Action for U.S. Appl. No. 17/450,864 mailed Dec. 28, 2023.
Final Office Action for U.S. Appl. No. 17/451,345 mailed Apr. 18, 2024.
Final Office Action for U.S. Appl. No. 17/451,345 mailed May 3, 2023.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/645,821 mailed Apr. 3, 2024.
Final Office Action for U.S. Appl. No. 17/646,771 mailed Dec. 21, 2023.
Final Office Action for U.S. Appl. No. 17/653,137 mailed Sep. 21, 2023.
Final Office Action for U.S. Appl. No. 17/655,464 mailed Sep. 1, 2023.
Final Office Action for U.S. Appl. No. 17/661,090 mailed Dec. 11, 2023.
Final Office Action for U.S. Appl. No. 17/663,330 mailed Dec. 12, 2023.
Final Office Action for U.S. Appl. No. 17/664,487 mailed Jan. 4, 2024.
Final Office Action for U.S. Appl. No. 17/808,354 mailed Apr. 10, 2024.
Final Office Action for U.S. Appl. No. 18/139,523 mailed Dec. 22, 2023.
Final Office Action for U.S. Appl. No. 18/140,163 mailed Mar. 27, 2024.
Final Office Action for U.S. Appl. No. 18/140,751 mailed Jan. 17, 2024.
Final Office Action for U.S. Appl. No. 18/164,800 mailed Dec. 6, 2023.
International Search Report and Written Opinion from International Application No. PCT/US2022/015026 mailed Oct. 31, 2022.
International Search Report and Written Opinion from International Application No. PCT/US2022/015420 mailed Nov. 18, 2022.
International Search Report and Written Opinion from International Application No. PCT/US2022/018159 mailed Dec. 12, 2022.
International Search Report and Written Opinion from International Application No. PCT/US2022/032424 mailed Oct. 11, 2022.
International Search Report and Written Opinion from International Application No. PCT/US2022/034744 mailed Dec. 9, 2022.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/041085 mailed Mar. 16, 2023.

(56) References Cited

OTHER PUBLICATIONS

International Search Report and Written Opinion from International Application No. PCT/US2022/041688 mailed Nov. 21, 2022.

International Search Report and Written Opinion from International Application No. PCT/US2022/042719 mailed Dec. 5, 2022.

International Search Report and Written Opinion from International Application No. PCT/US2022/042725 mailed Dec. 19, 2022.

International Search Report and Written Opinion from International Application No. PCT/US2022/043818 mailed Mar. 24, 2023.

International Search Report and Written Opinion from International Application No. PCT/US2022/044107 mailed Dec. 23, 2022.

International Search Report and Written Opinion from International Application No. PCT/US2022/044208 mailed May 8, 2023.

International Search Report and Written Opinion from International Application No. PCT/US2022/044212 mailed Jan. 20, 2023.

International Search Report and Written Opinion from International Application No. PCT/US2022/044243 mailed Feb. 24, 2023.

International Search Report and Written Opinion from International Application No. PCT/US2022/049300 mailed Jun. 6, 2023.

International Search Report and Written Opinion from International Application No. PCT/US2022/050909 mailed Jul. 24, 2023.

International Search Report and Written Opinion from International Application No. PCT/US2023/012696 mailed Jul. 6, 2023.

International Search Report and Written Opinion from International Application No. PCT/US2023/018474 mailed Sep. 11, 2023.

International Search Report and Written Opinion from International Application No. PCT/US2023/024805 mailed Dec. 14, 2023.

International Search Report and Written Opinion from International Application No. PCT/US2023/025192 mailed Feb. 7, 2024.

International Search Report and Written Opinion from International Application No. PCT/US2023/025939 mailed Feb. 7, 2024.

International Search Report and Written Opinion from International Application No. PCT/US2023/030365 mailed Mar. 13, 2024.

International Search Report and Written Opinion from International Application No. PCT/US2023/030373 mailed Mar. 13, 2024.

International Search Report and Written Opinion from International Application No. PCT/US2023/031433 mailed Mar. 4, 2024.

International Search Report and Written Opinion from International Application No. PCT/US2023/031740 mailed Mar. 4, 2024.

Issue Notification for U.S. Appl. No. 16/245,726 mailed Oct. 18, 2023.

Issue Notification for U.S. Appl. No. 16/899,956 mailed Mar. 29, 2023.

Issue Notification for U.S. Appl. No. 17/051,550 mailed Mar. 13, 2024.

Issue Notification for U.S. Appl. No. 17/051,554 mailed Mar. 6, 2024.

Issue Notification for U.S. Appl. No. 17/461,036 mailed Oct. 11, 2023.

Issue Notification for U.S. Appl. No. 17/663,046 mailed Dec. 20, 2023.

Issue Notification for U.S. Appl. No. 18/299,788 mailed Feb. 21, 2024.

Non-Final Office Action for U.S. Appl. No. 16/369,676 mailed Feb. 29, 2024.

Non-Final Office Action for U.S. Appl. No. 16/433,773 mailed Apr. 11, 2023.

Non-Final Office Action for U.S. Appl. No. 16/433,773 mailed Feb. 26, 2024.

Non-Final Office Action for U.S. Appl. No. 16/449,039 mailed Apr. 27, 2023.

Non-Final Office Action for U.S. Appl. No. 16/452,145 mailed Mar. 28, 2023.

Non-Final Office Action for U.S. Appl. No. 16/452,145 mailed Nov. 2, 2023.

Non-Final Office Action for U.S. Appl. No. 16/452,258 mailed Apr. 26, 2023.

Non-Final Office Action for U.S. Appl. No. 16/478,180 mailed Dec. 20, 2022.

Non-Final Office Action for U.S. Appl. No. 16/478,180 mailed Nov. 7, 2023.

Non-Final Office Action for U.S. Appl. No. 16/904,868 mailed Mar. 12, 2024.

Non-Final Office Action for U.S. Appl. No. 16/904,868 mailed Mar. 15, 2023.

Non-Final Office Action for U.S. Appl. No. 17/051,399 mailed Aug. 18, 2023.

Non-Final Office Action for U.S. Appl. No. 17/051,550 mailed Dec. 15, 2022.

Non-Final Office Action for U.S. Appl. No. 17/051,550 mailed Oct. 24, 2023.

Non-Final Office Action for U.S. Appl. No. 17/051,585 mailed Jan. 8, 2024.

Non-Final Office Action for U.S. Appl. No. 17/051,585 mailed Mar. 29, 2023.

Non-Final Office Action for U.S. Appl. No. 17/051,600 mailed Jan. 17, 2024.

Non-Final Office Action for U.S. Appl. No. 17/179,116 mailed Feb. 26, 2024.

Non-Final Office Action for U.S. Appl. No. 17/179,116 mailed Mar. 24, 2023.

Non-Final Office Action for U.S. Appl. No. 17/326,980 mailed Jul. 11, 2023.

Non-Final Office Action for U.S. Appl. No. 17/444,792 mailed Feb. 10, 2023.

Non-Final Office Action for U.S. Appl. No. 17/444,792 mailed Nov. 17, 2023.

Non-Final Office Action for U.S. Appl. No. 17/446,256 mailed Apr. 13, 2023.

Non-Final Office Action for U.S. Appl. No. 17/446,256 mailed Feb. 13, 2024.

Non-Final Office Action for U.S. Appl. No. 17/446,654 mailed Sep. 8, 2023.

Non-Final Office Action for U.S. Appl. No. 17/447,123 mailed Jan. 24, 2024.

Non-Final Office Action for U.S. Appl. No. 17/448,811 mailed Jan. 17, 2024.

Non-Final Office Action for U.S. Appl. No. 17/448,811 mailed Mar. 1, 2023.

Non-Final Office Action for U.S. Appl. No. 17/450,864 mailed May 10, 2023.

Non-Final Office Action for U.S. Appl. No. 17/451,345 mailed Jan. 17, 2024.

Non-Final Office Action for U.S. Appl. No. 17/451,354 mailed Apr. 4, 2024.

Non-Final Office Action for U.S. Appl. No. 17/451,354 mailed May 3, 2023.

Non-Final Office Action for U.S. Appl. No. 17/453,260 mailed Mar. 14, 2023.

Non-Final Office Action for U.S. Appl. No. 17/453,560 mailed Oct. 16, 2023.

Non-Final Office Action for U.S. Appl. No. 17/501,591 mailed Apr. 25, 2023.

Non-Final Office Action for U.S. Appl. No. 17/597,673 mailed Mar. 20, 2024.

Non-Final Office Action for U.S. Appl. No. 17/645,821 mailed Oct. 25, 2023.

Non-Final Office Action for U.S. Appl. No. 17/646,771 mailed Apr. 24, 2024.

Non-Final Office Action for U.S. Appl. No. 17/646,771 mailed Jul. 5, 2023.

Non-Final Office Action for U.S. Appl. No. 17/653,137 mailed Apr. 7, 2023.

Non-Final Office Action for U.S. Appl. No. 17/653,137 mailed Jan. 18, 2024.

Non-Final Office Action for U.S. Appl. No. 17/653,920 mailed Mar. 15, 2024.

Non-Final Office Action for U.S. Appl. No. 17/655,464 mailed Mar. 14, 2023.

Non-Final Office Action for U.S. Appl. No. 17/655,464 mailed Mar. 26, 2024.

(56) References Cited

OTHER PUBLICATIONS

Non-Final Office Action for U.S. Appl. No. 17/657,474 mailed Sep. 12, 2023.
Non-Final Office Action for U.S. Appl. No. 17/661,090 mailed Jul. 6, 2023.
Non-Final Office Action for U.S. Appl. No. 17/661,090 mailed May 22, 2024.
Non-Final Office Action for U.S. Appl. No. 17/663,330 mailed Jun. 29, 2023.
Non-Final Office Action for U.S. Appl. No. 17/664,487 mailed Jun. 8, 2023.
Non-Final Office Action for U.S. Appl. No. 17/664,914 mailed Jan. 31, 2024.
Non-Final Office Action for U.S. Appl. No. 17/808,354 mailed Nov. 28, 2023.
Non-Final Office Action for U.S. Appl. No. 18/003,029 mailed Mar. 26, 2024.
Non-Final Office Action for U.S. Appl. No. 18/134,857 mailed Jan. 25, 2024.
Non-Final Office Action for U.S. Appl. No. 18/139,523 mailed Aug. 17, 2023.
Non-Final Office Action for U.S. Appl. No. 18/140,163 mailed Nov. 9, 2023.
Non-Final Office Action for U.S. Appl. No. 18/140,751 mailed Sep. 14, 2023.
Non-Final Office Action for U.S. Appl. No. 18/164,800 mailed Mar. 22, 2024.
Non-Final Office Action for U.S. Appl. No. 18/198,464 mailed Dec. 7, 2023.
Notice of Allowance for U.S. Appl. No. 16/245,726 mailed Jul. 6, 2023.
Notice of Allowance for U.S. Appl. No. 16/369,676 mailed Nov. 14, 2023.
Notice of Allowance for U.S. Appl. No. 16/449,039 mailed Dec. 15, 2022.
Notice of Allowance for U.S. Appl. No. 16/449,039 mailed Mar. 28, 2024.
Notice of Allowance for U.S. Appl. No. 17/051,550 mailed Feb. 7, 2024.
Notice of Allowance for U.S. Appl. No. 17/051,554 mailed Jul. 6, 2023.
Notice of Allowance for U.S. Appl. No. 17/051,554 mailed Oct. 18, 2023.
Notice of Allowance for U.S. Appl. No. 17/326,980 mailed Apr. 5, 2024.
Notice of Allowance for U.S. Appl. No. 17/326,980 mailed Jan. 29, 2024.
Notice of Allowance for U.S. Appl. No. 17/453,260 mailed Apr. 8, 2024.
Notice of Allowance for U.S. Appl. No. 17/453,560 mailed Jan. 31, 2024.
Notice of Allowance for U.S. Appl. No. 17/461,036 mailed Feb. 22, 2023.
Notice of Allowance for U.S. Appl. No. 17/461,036 mailed Jun. 30, 2023.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/662,700 mailed Jul. 28, 2023.
Notice of Allowance for U.S. Appl. No. 17/662,700 mailed Mar. 28, 2023.
Notice of Allowance for U.S. Appl. No. 17/662,700 mailed Mar. 6, 2024.
Notice of Allowance for U.S. Appl. No. 17/662,700 mailed Nov. 15, 2023.
Notice of Allowance for U.S. Appl. No. 17/663,046 mailed Jan. 30, 2023.
Notice of Allowance for U.S. Appl. No. 18/198,464 mailed Apr. 17, 2024.
Notice of Allowance for U.S. Appl. No. 18/299,788 mailed Jul. 24, 2023.
Notice of Allowance for U.S. Appl. No. 18/299,788 mailed Nov. 6, 2023.
Restriction Requirement for U.S. Appl. No. 17/051,600 mailed Sep. 21, 2023.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.
Restriction Requirement for U.S. Appl. No. 17/667,097 mailed Mar. 20, 2024.
Restriction Requirement for U.S. Appl. No. 18/134,857 mailed Oct. 23, 2023.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
Text Messages to Lorena Eckert Re Prototype PureWick Holder dated Apr. 16, 2022.
U.S. Appl. No. 17/444,792, filed Aug. 10, 2021.
U.S. Appl. No. 17/451,719, filed Oct. 19, 2021.
U.S. Appl. No. 17/664,487, filed May 23, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/249,577, filed Oct. 19, 2021.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/294,370, filed Feb. 1, 2024.
U.S. Appl. No. 18/294,403, filed Feb. 1, 2024.
U.S. Appl. No. 18/299,788, filed Apr. 13, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.

(56)  References Cited

OTHER PUBLICATIONS

U.S. Appl. No. 18/569,778, filed Dec. 13, 2023.
U.S. Appl. No. 18/584,002, filed Feb. 22, 2024.
U.S. Appl. No. 18/610,523, filed Mar. 20, 2024.
U.S. Appl. No. 18/662,216, filed May 13, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 63/150,640, filed Feb. 18, 2021.
U.S. Appl. No. 63/308,190, filed Feb. 9, 2022.
U.S. Appl. No. 63/561,893, filed Dec. 11, 2023.
U.S. Appl. No. 63/596,012, filed Nov. 3, 2023.
U.S. Appl. No. 63/608,553, filed Dec. 11, 2023.
*PureWick Corporation* v. *Sage Products, LLC* Transcripts vol. 2, Mar. 29, 2022.
*PureWick Corporation* v. *Sage Products, LLC* Transcripts vol. 3, Mar. 30, 2022.
*PureWick Corporation* v. *Sage Products, LLC* Transcripts vol. 4, Mar. 31, 2022.
*PureWick Corporation* v. *Sage Products, LLC* Transcripts vol. 5, Apr. 1, 2022.
*PureWick Corporation* v. *Sage Products, LLC* Transcripts vol. 1, Mar. 28, 2022.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
Merriam-Webster Dictionary,, "Embed Definition & Meaning", https://www.merriam-webster.com/dictionary/embed last accessed Aug. 3, 2023, 2003.
Pieper, et al., "An external urine-collection device for women: A clinical trial", Journal of ER Nursing, vol. 20, No. 2, March/Apr. 1993, pp. 51-55.
Mnas, "A Solution for an Awkward—But Serious—Subject", http://www.aero-news.net/index.cfm?do=main.textpost&id=69ae2bb1-838b-4098-a7b5-7fbb2505688 last accessed Feb. 8, 2021.
Wikipedia Article, "Decibel" https://web.archive.org/web/2020041521917/https://en.wikipedia/org/wiki/Decibel last accessed Mar. 11, 2024, 21 pages.
Wikipedia Article, "Fiberglass", https://web.archive.org.web/20200309194847/https://en.wikipedia.org/wiki/Fiberglass last accessed Mar. 11, 2024.
Wikipedia Article, "Zylinder (Geometrie)", https://de.wikipedia.org/w/index.php?title=Zylinder (Geometrie)&oldid=154862081, version of Jun. 1, 2016, 7 pages.
Advisory Action for U.S. Appl. No. 16/452,258 mailed May 5, 2025.
Advisory Action for U.S. Appl. No. 16/478,180 mailed Jun. 7, 2024.
Advisory Action for U.S. Appl. No. 17/051,585 mailed Oct. 8, 2024.
Advisory Action for U.S. Appl. No. 17/444,792 mailed Jul. 8, 2024.
Advisory Action for U.S. Appl. No. 17/446,256 mailed Nov. 19, 2024.
Advisory Action for U.S. Appl. No. 17/446,654 mailed Feb. 28, 2025.

Advisory Action for U.S. Appl. No. 17/451,345 mailed Jul. 3, 2024.
Advisory Action for U.S. Appl. No. 17/451,345 mailed May 13, 2025.
Advisory Action for U.S. Appl. No. 17/595,747 mailed Mar. 17, 2025.
Advisory Action for U.S. Appl. No. 17/597,673 mailed Jan. 7, 2025.
Advisory Action for U.S. Appl. No. 17/645,821 mailed Jul. 2, 2024.
Advisory Action for U.S. Appl. No. 17/653,137 mailed Nov. 20, 2024.
Advisory Action for U.S. Appl. No. 17/653,314 mailed Apr. 8, 2025.
Advisory Action for U.S. Appl. No. 17/653,920 mailed Oct. 28, 2024.
Advisory Action for U.S. Appl. No. 17/655,464 mailed Feb. 25, 2025.
Advisory Action for U.S. Appl. No. 17/664,487 mailed Apr. 24, 2025.
Advisory Action for U.S. Appl. No. 17/808,354 mailed Jun. 12, 2024.
Advisory Action for U.S. Appl. No. 18/003,029 mailed Jan. 8, 2025.
Advisory Action for U.S. Appl. No. 18/134,857 mailed Oct. 23, 2024.
Advisory Action for U.S. Appl. No. 18/140,163 mailed Jun. 3, 2024.
Advisory Action for U.S. Appl. No. 18/164,800 mailed Jan. 8, 2025.
Corrected Notice of Allowability for U.S. Appl. No. 17/450,864 mailed Oct. 24, 2024.
Corrected Notice of Allowability for U.S. Appl. No. 17/501,591 mailed Aug. 9, 2024.
Corrected Notice of Allowability for U.S. Appl. No. 17/646,771 mailed Jan. 17, 2025.
Corrected Notice of Allowability for U.S. Appl. No. 17/664,914 mailed Aug. 9, 2024.
Corrected Notice of Allowability for U.S. Appl. No. 17/996,253 mailed Apr. 28, 2025.
Corrected Notice of Allowability for U.S. Appl. No. 18/134,857 mailed Mar. 14, 2025.
Corrected Notice of Allowability for U.S. Appl. No. 18/426,795 mailed Dec. 4, 2024.
Final Office Action for U.S. Appl. No. 16/433,773 mailed Sep. 9, 2024.
Final Office Action for U.S. Appl. No. 16/452,258 mailed Jan. 6, 2025.
Final Office Action for U.S. Appl. No. 17/051,585 mailed Jul. 5, 2024.
Final Office Action for U.S. Appl. No. 17/051,600 mailed Jun. 27, 2024.
Final Office Action for U.S. Appl. No. 17/446,256 mailed Aug. 7, 2024.
Final Office Action for U.S. Appl. No. 17/446,256 mailed Jun. 11, 2025.
Final Office Action for U.S. Appl. No. 17/446,654 mailed Dec. 18, 2024.
Final Office Action for U.S. Appl. No. 17/451,345 mailed Feb. 6, 2025.
Final Office Action for U.S. Appl. No. 17/451,354 mailed Oct. 28, 2024.
Final Office Action for U.S. Appl. No. 17/595,747 mailed Dec. 12, 2024.
Final Office Action for U.S. Appl. No. 17/597,408 mailed Mar. 24, 2025.
Final Office Action for U.S. Appl. No. 17/597,673 mailed Oct. 22, 2024.
Final Office Action for U.S. Appl. No. 17/614,173 mailed May 20, 2025.
Final Office Action for U.S. Appl. No. 17/625,941 mailed Feb. 18, 2025.
Final Office Action for U.S. Appl. No. 17/628,411 mailed Apr. 30, 2025.
Final Office Action for U.S. Appl. No. 17/653,137 mailed Aug. 7, 2024.
Final Office Action for U.S. Appl. No. 17/653,314 mailed Jan. 30, 2025.
Final Office Action for U.S. Appl. No. 17/653,920 mailed Apr. 24, 2025.

(56) References Cited

OTHER PUBLICATIONS

Final Office Action for U.S. Appl. No. 17/653,920 mailed Aug. 14, 2024.
Final Office Action for U.S. Appl. No. 17/655,464 mailed Nov. 29, 2024.
Final Office Action for U.S. Appl. No. 17/664,487 mailed Jan. 13, 2025.
Final Office Action for U.S. Appl. No. 17/757,311 mailed Mar. 31, 2025.
Final Office Action for U.S. Appl. No. 17/759,697 mailed Jun. 4, 2025.
Final Office Action for U.S. Appl. No. 17/808,354 mailed Jun. 13, 2025.
Final Office Action for U.S. Appl. No. 17/907,125 mailed Apr. 30, 2025.
Final Office Action for U.S. Appl. No. 18/003,029 mailed Oct. 22, 2024.
Final Office Action for U.S. Appl. No. 18/134,857 mailed Jul. 25, 2024.
Final Office Action for U.S. Appl. No. 18/139,523 mailed May 8, 2025.
Final Office Action for U.S. Appl. No. 18/164,800 mailed Oct. 22, 2024.
International Search Report and Written Opinion from International Application No. PCT/US2023/031432 mailed Feb. 29, 2024.
International Search Report and Written Opinion from International Application No. PCT/US2023/036238 mailed Jul. 22, 2024.
International Search Report and Written Opinion from International Application No. PCT/US2023/036868 mailed Jun. 5, 2024.
International Search Report and Written Opinion from International Application No. PCT/US2023/036875 mailed May 31, 2024.
International Search Report and Written Opinion from International Application No. PCT/US2023/075507 mailed Jun. 13, 2024.
International Search Report and Written Opinion from International Application No. PCT/US2023/077168 mailed Jun. 24, 2024.
International Search Report and Written Opinion from International Application No. PCT/US2023/077205 mailed Jul. 19, 2024.
International Search Report and Written Opinion from International Application No. PCT/US2023/077208 mailed May 10, 2024.
International Search Report and Written Opinion from International Application No. PCT/US2023/080680 mailed Jul. 22, 2024.
International Search Report and Written Opinion from International Application No. PCT/US2023/085516 mailed Aug. 26, 2024.
International Search Report and Written Opinion from International Application No. PCT/US2024/053681 mailed Jan. 27, 2025.
International Search Report and Written Opinion from International Application No. PCT/US2024/058598 mailed Mar. 28, 2025.
International Search Report and Written Opinion from International Application No. PCT/US2025/018907 mailed May 16, 2025.
International Search Report and Written Opinion from International Application No. PCT/US2025/018909 mailed May 20, 2025.
Issue Notification for U.S. Appl. No. 16/369,676 mailed Oct. 2, 2024.
Issue Notification for U.S. Appl. No. 16/449,039 mailed Jun. 19, 2024.
Issue Notification for U.S. Appl. No. 16/452,145 mailed Oct. 23, 2024.
Issue Notification for U.S. Appl. No. 16/478,180 mailed Mar. 5, 2025.
Issue Notification for U.S. Appl. No. 16/904,868 mailed Apr. 30, 2025.
Issue Notification for U.S. Appl. No. 17/051,585 mailed Mar. 26, 2025.
Issue Notification for U.S. Appl. No. 17/179,116 mailed Dec. 25, 2024.
Issue Notification for U.S. Appl. No. 17/326,980 mailed Jul. 10, 2024.
Issue Notification for U.S. Appl. No. 17/447,123 mailed Nov. 13, 2024.

Issue Notification for U.S. Appl. No. 17/448,811 mailed Jul. 3, 2024.
Issue Notification for U.S. Appl. No. 17/450,864 mailed Jan. 8, 2025.
Issue Notification for U.S. Appl. No. 17/453,260 mailed Jul. 10, 2024.
Issue Notification for U.S. Appl. No. 17/453,560 mailed Aug. 7, 2024.
Issue Notification for U.S. Appl. No. 17/501,591 mailed Mar. 5, 2025.
Issue Notification for U.S. Appl. No. 17/529,769 mailed Feb. 19, 2025.
Issue Notification for U.S. Appl. No. 17/597,673 mailed Jun. 4, 2025.
Issue Notification for U.S. Appl. No. 17/646,771 mailed Mar. 19, 2025.
Issue Notification for U.S. Appl. No. 17/657,474 mailed Jun. 19, 2024.
Issue Notification for U.S. Appl. No. 17/661,090 mailed Feb. 5, 2025.
Issue Notification for U.S. Appl. No. 17/662,700 mailed Oct. 23, 2024.
Issue Notification for U.S. Appl. No. 17/663,330 mailed Feb. 26, 2025.
Issue Notification for U.S. Appl. No. 17/664,914 mailed Nov. 6, 2024.
Issue Notification for U.S. Appl. No. 17/667,097 mailed Dec. 11, 2024.
Issue Notification for U.S. Appl. No. 17/749,340 mailed May 28, 2025.
Issue Notification for U.S. Appl. No. 18/134,857 mailed May 28, 2025.
Issue Notification for U.S. Appl. No. 18/140,163 mailed Dec. 4, 2024.
Issue Notification for U.S. Appl. No. 18/140,751 mailed Feb. 12, 2025.
Issue Notification for U.S. Appl. No. 18/198,464 mailed Nov. 20, 2024.
Issue Notification for U.S. Appl. No. 18/389,009 mailed Dec. 18, 2024.
Issue Notification for U.S. Appl. No. 18/415,080 mailed Apr. 9, 2025.
Issue Notification for U.S. Appl. No. 18/426,795 mailed Feb. 19, 2025.
Issue Notification for U.S. Appl. No. 18/584,002 mailed Apr. 16, 2025.
Non-Final Office Action for U.S. Appl. No. 16/433,773 mailed Feb. 28, 2025.
Non-Final Office Action for U.S. Appl. No. 16/452,258 mailed Jun. 20, 2024.
Non-Final Office Action for U.S. Appl. No. 16/478,180 mailed Aug. 7, 2024.
Non-Final Office Action for U.S. Appl. No. 17/051,600 mailed Feb. 28, 2025.
Non-Final Office Action for U.S. Appl. No. 17/378,015 mailed Jul. 5, 2024.
Non-Final Office Action for U.S. Appl. No. 17/394,055 mailed Mar. 13, 2025.
Non-Final Office Action for U.S. Appl. No. 17/394,055 mailed Mar. 19, 2025.
Non-Final Office Action for U.S. Appl. No. 17/444,792 mailed Oct. 30, 2024.
Non-Final Office Action for U.S. Appl. No. 17/446,256 mailed Dec. 13, 2024.
Non-Final Office Action for U.S. Appl. No. 17/446,654 mailed Jun. 25, 2024.
Non-Final Office Action for U.S. Appl. No. 17/446,654 mailed May 1, 2025.
Non-Final Office Action for U.S. Appl. No. 17/450,864 mailed May 29, 2024.
Non-Final Office Action for U.S. Appl. No. 17/451,345 mailed Jul. 25, 2024.

(56) References Cited

OTHER PUBLICATIONS

Non-Final Office Action for U.S. Appl. No. 17/451,354 mailed Mar. 19, 2025.
Non-Final Office Action for U.S. Appl. No. 17/595,747 mailed Jun. 12, 2025.
Non-Final Office Action for U.S. Appl. No. 17/595,747 mailed Jun. 7, 2024.
Non-Final Office Action for U.S. Appl. No. 17/597,408 mailed Aug. 15, 2024.
Non-Final Office Action for U.S. Appl. No. 17/614,173 mailed Sep. 24, 2024.
Non-Final Office Action for U.S. Appl. No. 17/625,941 mailed Nov. 4, 2024.
Non-Final Office Action for U.S. Appl. No. 17/628,411 mailed Sep. 23, 2024.
Non-Final Office Action for U.S. Appl. No. 17/631,619 mailed Mar. 19, 2025.
Non-Final Office Action for U.S. Appl. No. 17/645,821 mailed Mar. 31, 2025.
Non-Final Office Action for U.S. Appl. No. 17/645,821 mailed Sep. 6, 2024.
Non-Final Office Action for U.S. Appl. No. 17/653,137 mailed Jan. 28, 2025.
Non-Final Office Action for U.S. Appl. No. 17/653,314 mailed Aug. 29, 2024.
Non-Final Office Action for U.S. Appl. No. 17/653,314 mailed May 8, 2025.
Non-Final Office Action for U.S. Appl. No. 17/653,920 mailed Nov. 27, 2024.
Non-Final Office Action for U.S. Appl. No. 17/655,464 mailed Mar. 20, 2025.
Non-Final Office Action for U.S. Appl. No. 17/663,330 mailed Jul. 1, 2024.
Non-Final Office Action for U.S. Appl. No. 17/664,487 mailed Jun. 17, 2024.
Non-Final Office Action for U.S. Appl. No. 17/664,487 mailed May 19, 2025.
Non-Final Office Action for U.S. Appl. No. 17/749,340 mailed Aug. 14, 2024.
Non-Final Office Action for U.S. Appl. No. 17/754,736 mailed Mar. 31, 2025.
Non-Final Office Action for U.S. Appl. No. 17/756,201 mailed Apr. 24, 2025.
Non-Final Office Action for U.S. Appl. No. 17/757,311 mailed Oct. 22, 2024.
Non-Final Office Action for U.S. Appl. No. 17/758,152 mailed Apr. 8, 2025.
Non-Final Office Action for U.S. Appl. No. 17/758,316 mailed Aug. 28, 2024.
Non-Final Office Action for U.S. Appl. No. 17/759,697 mailed Dec. 4, 2024.
Non-Final Office Action for U.S. Appl. No. 17/808,354 mailed Dec. 13, 2024.
Non-Final Office Action for U.S. Appl. No. 17/809,083 mailed Apr. 2, 2025.
Non-Final Office Action for U.S. Appl. No. 17/809,083 mailed Mar. 7, 2025.
Non-Final Office Action for U.S. Appl. No. 17/878,268 mailed Mar. 17, 2025.
Non-Final Office Action for U.S. Appl. No. 17/907,125 mailed Dec. 13, 2024.
Non-Final Office Action for U.S. Appl. No. 17/912,147 mailed May 29, 2025.
Non-Final Office Action for U.S. Appl. No. 17/996,064 mailed Mar. 6, 2025.
Non-Final Office Action for U.S. Appl. No. 18/003,029 mailed Apr. 18, 2025.
Non-Final Office Action for U.S. Appl. No. 18/006,807 mailed May 29, 2025.

Non-Final Office Action for U.S. Appl. No. 18/042,842 mailed May 22, 2025.
Non-Final Office Action for U.S. Appl. No. 18/043,618 mailed May 19, 2025.
Non-Final Office Action for U.S. Appl. No. 18/139,523 mailed Aug. 26, 2024.
Non-Final Office Action for U.S. Appl. No. 18/140,751 mailed Jun. 21, 2024.
Non-Final Office Action for U.S. Appl. No. 18/164,800 mailed Apr. 25, 2025.
Non-Final Office Action for U.S. Appl. No. 18/247,986 mailed Jun. 4, 2025.
Non-Final Office Action for U.S. Appl. No. 18/264,004 mailed May 15, 2025.
Non-Final Office Action for U.S. Appl. No. 18/389,009 mailed May 24, 2024.
Non-Final Office Action for U.S. Appl. No. 18/426,795 mailed Aug. 9, 2024.
Non-Final Office Action for U.S. Appl. No. 18/451,080 mailed Jul. 30, 2024.
Non-Final Office Action for U.S. Appl. No. 18/584,002 mailed Sep. 19, 2024.
Notice of Allowance for U.S. Appl. No. 16/369,676 mailed Jun. 17, 2024.
Notice of Allowance for U.S. Appl. No. 16/452,145 mailed Jul. 11, 2024.
Notice of Allowance for U.S. Appl. No. 16/478,180 mailed Dec. 16, 2024.
Notice of Allowance for U.S. Appl. No. 16/904,868 mailed Jan. 21, 2025.
Notice of Allowance for U.S. Appl. No. 16/904,868 mailed Sep. 29, 2024.
Notice of Allowance for U.S. Appl. No. 17/051,585 mailed Dec. 26, 2024.
Notice of Allowance for U.S. Appl. No. 17/179,116 mailed Sep. 13, 2024.
Notice of Allowance for U.S. Appl. No. 17/444,792 mailed Mar. 28, 2025.
Notice of Allowance for U.S. Appl. No. 17/447,123 mailed Jul. 26, 2024.
Notice of Allowance for U.S. Appl. No. 17/448,811 mailed Jun. 14, 2024.
Notice of Allowance for U.S. Appl. No. 17/450,864 mailed Sep. 18, 2024.
Notice of Allowance for U.S. Appl. No. 17/501,591 mailed Jul. 31, 2024.
Notice of Allowance for U.S. Appl. No. 17/501,591 mailed Nov. 20, 2024.
Notice of Allowance for U.S. Appl. No. 17/527,769 mailed Nov. 20, 2024.
Notice of Allowance for U.S. Appl. No. 17/596,629 mailed Jan. 29, 2025.
Notice of Allowance for U.S. Appl. No. 17/596,629 mailed May 27, 2025.
Notice of Allowance for U.S. Appl. No. 17/597,673 mailed Feb. 26, 2025.
Notice of Allowance for U.S. Appl. No. 17/646,771 mailed Dec. 17, 2024.
Notice of Allowance for U.S. Appl. No. 17/661,090 mailed Oct. 30, 2024.
Notice of Allowance for U.S. Appl. No. 17/662,700 mailed Jun. 12, 2024.
Notice of Allowance for U.S. Appl. No. 17/663,330 mailed Nov. 20, 2024.
Notice of Allowance for U.S. Appl. No. 17/664,914 mailed Jul. 26, 2024.
Notice of Allowance for U.S. Appl. No. 17/667,097 mailed Aug. 28, 2024.
Notice of Allowance for U.S. Appl. No. 17/749,340 mailed Feb. 14, 2025.
Notice of Allowance for U.S. Appl. No. 17/758,316 mailed Mar. 24, 2025.

(56) References Cited

OTHER PUBLICATIONS

Notice of Allowance for U.S. Appl. No. 17/996,155 mailed Mar. 11, 2025.
Notice of Allowance for U.S. Appl. No. 17/996,253 mailed Apr. 11, 2025.
Notice of Allowance for U.S. Appl. No. 17/996,468 mailed Apr. 14, 2025.
Notice of Allowance for U.S. Appl. No. 18/134,857 mailed Feb. 20, 2025.
Notice of Allowance for U.S. Appl. No. 18/140,163 mailed Aug. 21, 2024.
Notice of Allowance for U.S. Appl. No. 18/140,751 mailed Nov. 1, 2024.
Notice of Allowance for U.S. Appl. No. 18/198,464 mailed Jul. 30, 2024.
Notice of Allowance for U.S. Appl. No. 18/389,009 mailed Aug. 28, 2024.
Notice of Allowance for U.S. Appl. No. 18/415,080 mailed Dec. 30, 2024.
Notice of Allowance for U.S. Appl. No. 18/426,795 mailed Nov. 20, 2024.
Notice of Allowance for U.S. Appl. No. 18/584,002 mailed Jan. 8, 2025.
Restriction Requirement for U.S. Appl. No. 17/527,769 mailed Jun. 17, 2024.
Restriction Requirement for U.S. Appl. No. 17/596,629 mailed Sep. 19, 2024.
Restriction Requirement for U.S. Appl. No. 17/625,941 mailed Aug. 7, 2024.
Restriction Requirement for U.S. Appl. No. 17/754,736 mailed Nov. 20, 2024.
Restriction Requirement for U.S. Appl. No. 17/755,236 mailed Apr. 24, 2025.
Restriction Requirement for U.S. Appl. No. 17/756,201 mailed Oct. 4, 2024.
Restriction Requirement for U.S. Appl. No. 17/758,152 mailed Nov. 5, 2024.
Restriction Requirement for U.S. Appl. No. 17/809,083 mailed Dec. 31, 2024.
Restriction Requirement for U.S. Appl. No. 17/878,268 mailed Sep. 20, 2024.
Restriction Requirement for U.S. Appl. No. 17/929,887 mailed Mar. 10, 2025.
Restriction Requirement for U.S. Appl. No. 18/041,109 mailed Jun. 4, 2025.
Restriction Requirement for U.S. Appl. No. 18/150,360 mailed May 19, 2025.
Supplemental Notice of Allowance for U.S. Appl. No. 17/597,673 mailed Apr. 10, 2025.
U.S. Appl. No. 17/013,822, filed Sep. 7, 2020.
U.S. Appl. No. 17/596,629, filed Dec. 15, 2021.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.

U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/851,197, filed Sep. 26, 2024.
U.S. Appl. No. 18/886,306, filed Sep. 16, 2024.
U.S. Appl. No. 18/903,592, filed Oct. 1, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.
U.S. Appl. No. 18/951,944, filed Nov. 19, 2024.
U.S. Appl. No. 18/957,011, filed Nov. 22, 2024.
U.S. Appl. No. 18/974,367, filed Dec. 9, 2024.
U.S. Appl. No. 18/982,930, filed Dec. 16, 2024.
U.S. Appl. No. 19/038,774, filed Jan. 28, 2025.
U.S. Appl. No. 19/039,165, filed Jan. 28, 2025.
U.S. Appl. No. 19/046,047, filed Feb. 5, 2025.
U.S. Appl. No. 19/047,728, filed Feb. 7, 2025.
U.S. Appl. No. 19/048,004, filed Feb. 7, 2025.
U.S. Appl. No. 19/049,501, filed Feb. 10, 2025.
U.S. Appl. No. 19/049,783, filed Feb. 10, 2025.
U.S. Appl. No. 19/058,726, filed Feb. 20, 2025.
U.S. Appl. No. 19/069,480, filed Mar. 4, 2025.
U.S. Appl. No. 19/078,602, filed Mar. 13, 2025.
U.S. Appl. No. 19/092,262, filed Mar. 27, 2025.
U.S. Appl. No. 19/103,165, filed Feb. 11, 2025.
U.S. Appl. No. 19/110,938, filed Mar. 12, 2025.
U.S. Appl. No. 19/111,921, filed Mar. 14, 2025.
U.S. Appl. No. 19/127,234, filed May 5, 2025.
U.S. Appl. No. 19/171,983, filed Apr. 7, 2025.
U.S. Appl. No. 19/179,540, filed Apr. 15, 2025.
U.S. Appl. No. 19/202,862, filed May 8, 2025.
U.S. Appl. No. 19/207,699, filed May 14, 2025.
U.S. Appl. No. 19/215,723, filed May 22, 2025.
U.S. Appl. No. 19/237,368, filed Jun. 13, 2025.
U.S. Appl. No. 63/181,709, filed Apr. 29, 2021.
U.S. Appl. No. 63/564,696, filed Mar. 13, 2024.
U.S. Appl. No. 63/568,615, filed Mar. 22, 2024.
U.S. Appl. No. 63/683,428, filed Aug. 15, 2024.
U.S. Appl. No. 63/711,438, filed Oct. 24, 2024.
U.S. Appl. No. 63/711,445, filed Oct. 24, 2024.
U.S. Appl. No. 63/720,004, filed Nov. 13, 2024.
"Dictionary.com, ABUT Definition and Meaning", Dictionary.com, https://www.dictionary.com/browse/abut, 2024, 1 page.
"OBLONG", Cambridge Dictionary, https://dictionary.cambridge.org/dictionary/english/oblong, 2024, 1 page.
Britannica, "Polyolefin", Britannica Online Encyclopedia, T. Editors of Encyclopaedia, https://www.britannica.com/science/polyolefin, Jul. 26, 2012.
FOAMTECH, "Foam Packaging Isnert: Best Selection Guide", https://web/archive.org/web/20170922162235/http://www.foamtechchina/com:80/foam-packaging-insert/, Sep. 22, 2017, 25 pages.
Martin, "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.

* cited by examiner

FLUID COLLECTION ASSEMBLIES INCLUDING AN EXTENSION

CROSS-REFERENCE TO RELATED APPLICATION(S)

This application claims priority to U.S. Provisional Patent Application No. 63/241,562 filed on Sep. 8, 2021, the disclosure of which is incorporated herein, in its entirety, by this reference.

BACKGROUND

A person or animal may have limited or impaired mobility so typical urination processes are challenging or impossible. For example, a person may experience or have a disability that impairs mobility. A person may have restricted travel conditions such as those experienced by pilots, drivers, and workers in hazardous areas. Additionally, sometimes bodily fluids collection is needed for monitoring purposes or clinical testing.

Urinary catheters, such as a Foley catheter, can address some of these circumstances, such as incontinence. Unfortunately, urinary catheters can be uncomfortable, painful, and can lead to complications, such as infections. Additionally, bed pans, which are receptacles used for the toileting of bedridden individuals are sometimes used. However, bedpans can be prone to discomfort, spills, and other hygiene issues.

SUMMARY

Embodiments are directed to fluid collection assemblies including an extension, fluid collection systems including the same, and methods of using the same. In an embodiment, a fluid collection assembly is disclosed. The fluid collection assembly includes a fluid impermeable layer including a proximal end region and a distal end region spaced from the proximal end region. The fluid impermeable layer defines at least a chamber, at least one opening, and a fluid outlet. The fluid collection assembly also includes at least one porous material disposed in the chamber and an extension extending from or near the distal end region. The extension is configured to be positioned in a gluteal cleft on an individual. The extension is at least one of reversibly attachable to the fluid impermeable layer, inflatable, or configured to change a distance that the extension extends from the distal end region of the fluid impermeable layer.

In an embodiment, a fluid collection system is disclosed. The fluid collection system includes a fluid collection assembly. The fluid collection assembly includes a fluid impermeable layer including a proximal end region and a distal end region spaced from the proximal end region. The fluid impermeable layer defines at least a chamber, at least one opening, and a fluid outlet. The fluid collection assembly also includes at least one porous material disposed in the chamber and an extension extending from or near the distal end region. The extension is configured to be positioned in a gluteal cleft on an individual. The extension is at least one of reversibly attachable to the fluid impermeable layer, inflatable, or configured to change a distance that the extension extends from the distal end region of the fluid impermeable layer. The fluid collection system also includes a fluid storage container and a vacuum source. the chamber of the fluid collection assembly is in fluid communication with the fluid storage container and the vacuum source via one or more conduits In an embodiment, a method of using a fluid collection assembly is disclosed. The method includes positioning an opening of a fluid collection assembly adjacent to a urethral opening of an individual. The fluid collection assembly includes a fluid impermeable layer including a proximal end region and a distal end region spaced from the proximal end region. The fluid impermeable layer defines at least a chamber, at least one opening, and a fluid outlet. The fluid collection assembly also includes at least one porous material disposed in the chamber. The method also includes positioning an extension of the fluid collection assembly in a gluteal cleft of the individual. The extension extends from or near the distal end region of the fluid impermeable layer. The extension is at least one of reversibly attachable to the fluid impermeable layer, inflatable, or configured to change a distance that the extension extends from the distal end region of the fluid impermeable layer.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Figure 1A:
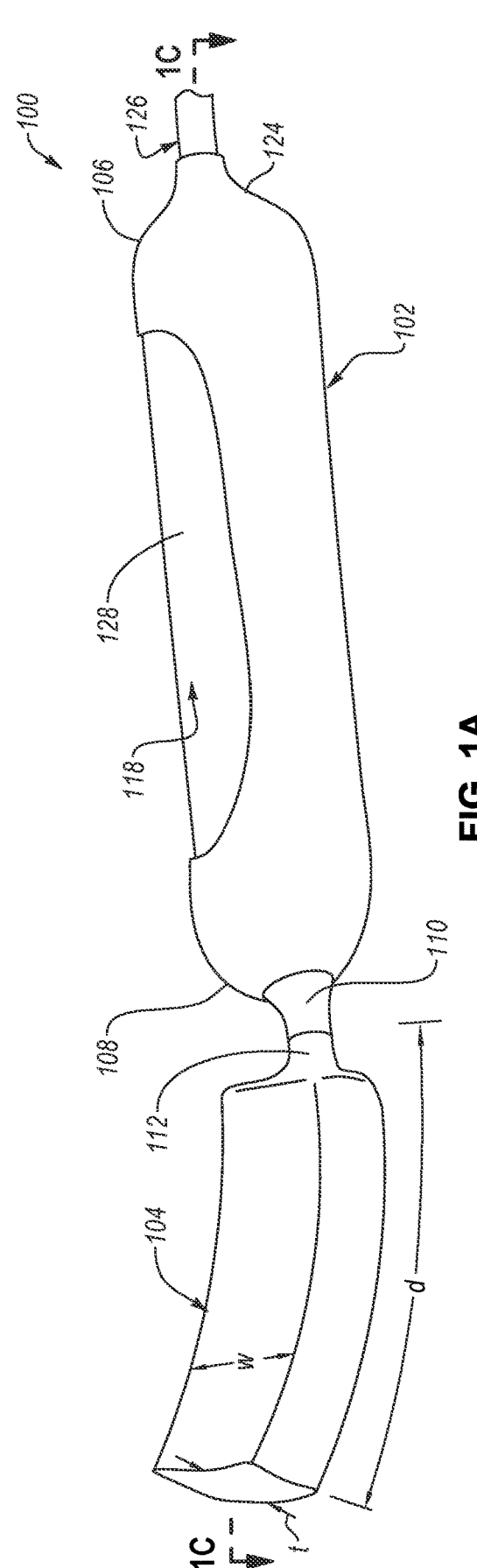
FIGS. 1A and 1B are isometric views of a fluid collection assembly that includes a fluid impermeable layer and an extension reversibly attached to and reversibly detached from the fluid impermeable layer, respectively, according to an embodiment.

Embodiments are directed to fluid collection assemblies including an extension, fluid collection systems including the same, and methods of using the same. An example fluid collection assembly includes a fluid impermeable layer (e.g., a fluid impermeable barrier). The fluid impermeable layer includes a proximal end region and a distal end region. The fluid impermeable layer also defines at least a chamber, at least one opening that may be between the proximal and distal end regions, and a fluid outlet that may be at the proximal end region. The fluid collection assembly may also include at least one porous material disposed in the chamber.

The fluid collection assembly further includes an extension that is at least one of attachable or extends from or near the distal end region of the fluid impermeable layer. The extension is configured to be disposed within the gluteal cleft (e.g., between the buttocks) to help secure the fluid collection assembly to an individual using the fluid collection assembly.

During use, the fluid collection assembly may be disposed on the individual such that the opening defined by the fluid impermeable layer is adjacent to the urethral opening of the individual. The fluid collection assembly may receive one or more bodily fluids (e.g., urine, blood, sweat, etc.) discharged from the urethral opening and the region about the urethral opening. The bodily fluids discharged from the individual may be received through the opening, into the porous material, and may be temporarily stored in the chamber. The bodily fluids may be removed from the chamber through the fluid outlet, such as by a conduit that is in fluid communication with the chamber through the fluid outlet. In an embodiment, the chamber of the fluid collection assembly may be in fluid communication with a vacuum source and a fluid storage container via the conduit. The vacuum source may apply a suction force to the chamber through the conduit that facilitates removal of the bodily fluids from the chamber and the bodily fluids removed from the chamber may be deposited in the fluid storage container.

The fluid collection assembly may be disposed and maintained adjacent to the urethral opening to prevent or at least inhibit the formation of gaps between the fluid collection assembly and the individual. Bodily fluids may leak from the fluid collection assembly or fail to be received into the chamber (e.g., into the porous material) when there are gaps between the fluid collection assembly and the individual. Some conventional fluid collection assemblies rely on contact between the thighs of the individual and the fluid impermeable layer to maintain the fluid collection assembly adjacent to the urethral opening and to prevent or at least inhibit the formation of gaps between the fluid collection assembly and the individual. Some of these convention fluid collection assemblies may also include an extension extending from a portion of the conventional fluid collection assemblies. The extension may be configured to be disposed in the gluteal cleft of the individual thereby helping maintain the fluid collection assembly adjacent to the urethral opening. Some individuals may find the extension of such conventional fluid collection assemblies to be uncomfortable and, thus, prefer to use fluid collection assemblies without extensions. Other individuals may only like using extensions of such conventional fluid collection assemblies in certain situations. For example, the individuals may only like using conventional fluid collection assemblies with extensions when in one or more first positions (e.g., one or more of lying down, sitting, or standing) and may not like using conventional fluid collection assemblies when in one or more second positions since the extensions may move or put pressure in the gluteal cleft when the individual changes positions. Further, an extension of the conventional fluid collection assembly that is correctly positioned when the individual is lying down may contact or be otherwise influenced by a surface when the individual sits up which may cause the conventional fluid collection assembly to move. Causing the conventional fluid collection assembly to move may cause discomfort to the individual and may result in the formation of gaps between the conventional fluid collection assembly and the individual.

The fluid collection assemblies disclosed herein include at least one extension that is at least one of reversibly attachable to the fluid impermeable layer, inflatable and/or deflatable, or may selectively change a distance that the extension extends from the fluid impermeable layer. These extensions resolve at least some of the issues associated with the extensions of the conventional fluid collection assemblies disclosed above. In an example, an individual that wants to use a fluid collection assembly that does not include an extension may at least one of detach the extension from the fluid impermeable layer, deflate or fail to inflate the extension, or may decrease the distance that the extension extends from the fluid impermeable layer. In such an example, each of the extensions may prevent or at least inhibit any discomfort to the individual that would otherwise be caused by the extension. In an example, an individual that originally has an extension disposed in the gluteal cleft may, upon changing their position, at least one of detach the extension from the fluid impermeable layer, deflate the extension, or may decrease the distance that the extension extends from the fluid impermeable layer. In such an example, each of the extensions may prevent or at least inhibit issues (e.g., discomfort, contact a surface, etc.) that would otherwise be caused by the extension of a conventional fluid collection assembly when the individual changes positions.

The extensions disclosed herein allow for greater configurability depending on the preferences of the individual. In an example, an extension that is reversibly attachable to the fluid collection assembly may allow the individual to select an extension (e.g., based on size and/or shape of the extension) that the individual prefers. Further, reversibly detaching the extension allows the extension to be reused with another fluid collection assembly (e.g., after washing the extension) thereby decreasing waste and allowing the individual to reuse a preferred extension. In an example, an extension that is inflatable and/or deflatable allows the individual to select the size and firmness of the extension depending on the individual's preference. For instance, the individual may inflate the extension if the individual prefers a larger and/or more firm extension or may deflate the extension if the individual prefers a smaller and/or less firm extension. In an example, the extension that may change a distance that the extension extends from the fluid impermeable layer allows the individual to select where the extension is positioned within the gluteal cleft.

Figure 1B:
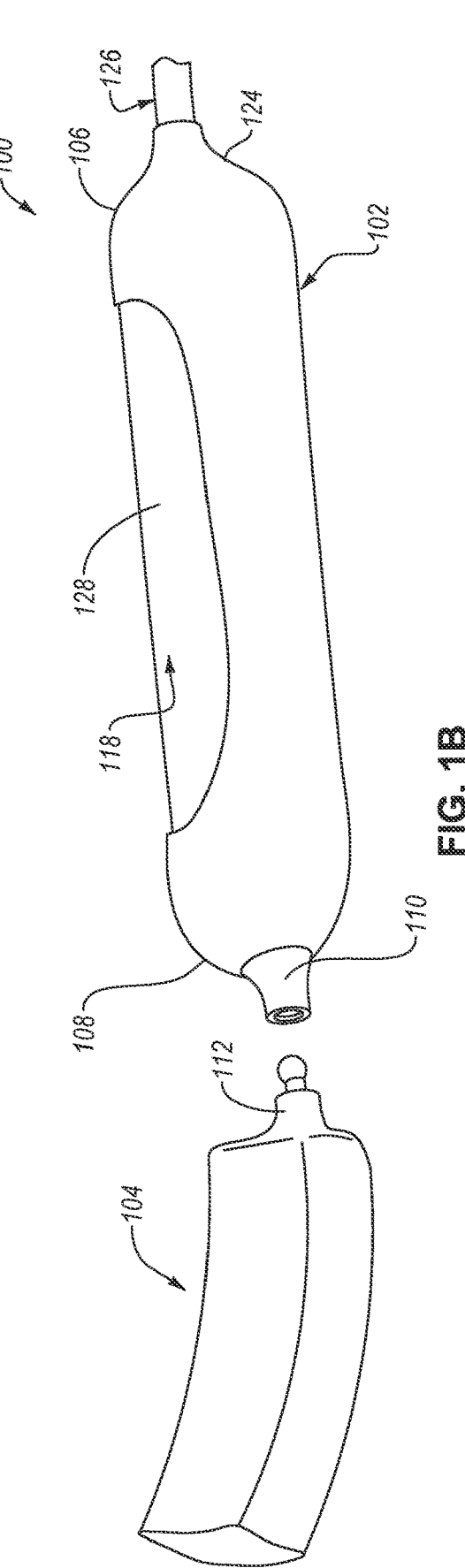
Figure 1C:
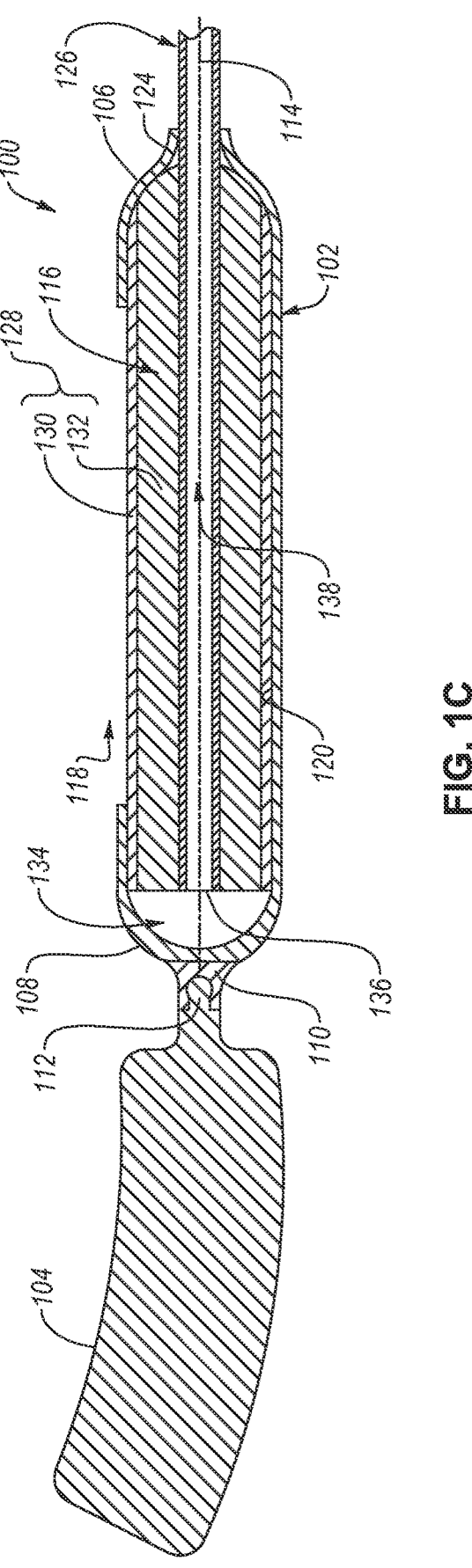
FIG. 1C is a cross-sectional schematic of the fluid collection assembly illustrated in FIG. 1A.

FIGS. 1A and 1B are isometric views of a fluid collection assembly 100 that includes a fluid impermeable layer 102 and an extension 104 reversibly attached to and reversibly detached from the fluid impermeable layer 102, respectively, according to an embodiment. FIG. 1C is a cross-sectional schematic of the fluid collection assembly 100 illustrated in FIG. 1A. The fluid impermeable layer 102 includes a proximal end region 106 and a distal end region 108 opposite and spaced from the proximal end region 106. When the extension 104 is attached to the fluid impermeable layer 102, the extension 104 may extend from or near the distal end region 108. For example, the distal end region 108 may be the closest portion of the fluid impermeable layer 102 to the gluteal cleft of the individual using the fluid collection assembly 100. As such, extending the extension 104 from or near the distal end region 108 allows the extension 104 to be more easily positioned in the gluteal cleft.

As previously discussed, the extension 104 is configured to extend from the fluid impermeable layer 102 and be positioned in the gluteal cleft of an individual to facilitate securing the fluid collection assembly 100 to the individual. For example, the extension 104 may secure the fluid collection assembly 100 to the individual to maintain an opening 118 adjacent to the urethral opening of the individual and to prevent the formation of gaps between the fluid collection assembly 100 and the individual. The extension 104 may exhibit any suitable shape that allows the extension 104 to be positioned in the gluteal cleft. In an example, as illustrated, the extension 104 exhibits a generally flat shape. The generally flat shape of the extension 104 allows the extension 104 to be positioned between the gluteal cleft while minimizing the distance that the extension 104 pushed the buttocks of the individual apart thereby increasing the individual's comfort. Also, the generally flat shape may increase the surface area of the extension 104 that contacts the buttocks of the individual which may better maintain the extension 104 in the gluteal cleft. In an example, the extension 104 may exhibit a generally cylindrical shape (e.g., generally rod-like shape) or a similar rounded shape (e.g., a shape exhibiting a generally oval or ellipsoidal cross-sectional shape). The generally cylindrical shape or rounded shape of the extension 104 may prevent the extension 104 from including corners that may uncomfortably press into the buttock of the individual. The shape of the extension 104 may be selected based on the size and shape of the individual's anatomy and/or based on the individual's preference.

In an embodiment, the extension 104 may exhibit a curved (e.g., a bent) shape. The curved shape of the extension 104 may allow the extension 104 to better conform to the shape of the anatomy of the individual than if the extension 104 was generally straight. For example, the gluteal cleft may extend along a generally curved path and the generally curved shape of the extension 104 may better correspond to the curved path of the gluteal cleft than if the extension 104 was generally straight. Configuring the extension 104 to generally correspond to the path of the gluteal cleft may prevent or at least inhibit the extension 104 extending out of the gluteal cleft which may increase the likelihood that the extension 104 becomes dislodged from the gluteal cleft.

The extension 104 may extend a distance d from the fluid impermeable layer 102. The distance d may be measured generally parallel to a longitudinal axis 114 of the fluid collection assembly 100 and/or parallel to a longitudinal axis of the extension 104. The distance d that the extension 104 extends from the fluid impermeable layer 102 may be about 1 cm or greater, about 2 cm or greater, about 3 cm or greater, about 5 cm or greater, about 7.5 cm or greater, about 10 cm or greater, about 12.5 cm or greater, about 15 cm or greater, about 17.5 cm or greater, about 20 cm or greater, about 22.5 cm or greater, about 25 cm or greater, or in ranges of about 1 cm to about 3 cm, about 2 cm to about 5 cm, about 3 cm to about 7.5 cm, about 5 cm to about 10 cm, about 7.5 cm to about 12.5 cm, about 10 cm to about 15 cm, about 12.5 cm to about 17.5 cm, about 15 cm to about 20 cm, about 17.5 cm to about 22.5 cm, or about 20 cm to about 25 cm. The distance d that the extension 104 extends from the fluid impermeable layer 102 may depend on a variety of factors. In an example, the distance d that the extension 104 extends from the fluid impermeable layer 102 may depend on the size of the anatomy the individual. For instance, the distance d that the extension 104 extends from the fluid impermeable layer 102 may be greater when used with a larger individual than with a smaller individual since the larger individual may have a larger (e.g., longer) gluteal cleft that can receive the extension 104 and the distance from the distal end region 108 to the gluteal cleft may be larger with the larger individual. In an example, the distance d that the extension 104 extends from the fluid impermeable layer 102 may depend on the individual's preference since some individuals may like extensions 104 that are extend further from the fluid impermeable layer 102 than other. In either example, reversibly attaching the extension 104 to the fluid impermeable layer 102 allows the fluid impermeable layer 102 to be chosen depending on the size of the individual and/or the individual's preference.

The extension 104 may exhibit a width W and a thickness t. The width W and the thickness t may be measured perpendicular to the distance d wherein the width W is equal to or greater than the thickness t. The width W and the thickness t may be about 0.5 mm or greater, about 1 mm or greater, about 2 mm or greater, about 3 mm or greater, about 4 mm or greater, about 5 mm or greater, about 6 mm or greater, about 7 mm or greater, about 8 mm or greater, about 1 cm or greater, about 1.2 cm or greater, about 1.5 cm or greater, about 2 cm or greater, or in ranges of about 0.5 mm to about 2 mm, about 1 mm to about 3 mm, about 2 mm to about 4 mm, about 3 mm to about 5 mm, about 4 mm to about 6 mm, about 5 mm to about 7 mm, about 6 mm to about 8 mm, about 7 mm to about 1 cm, about 8 mm to about 1.2 cm, about 1 cm to about 1.5 cm, or about 1.2 cm to about 2 cm. The width W and the thickness t may be selected based on the shape of the extension 104 (e.g., flat shape vs cylindrical shape) or for any of the same reasons discussed above with regards to the distance d.

Referring to FIG. 1A, the lateral and traverse directions refers to directions that are generally perpendicular to a longitudinal axis 114. The lateral direction is parallel to a direction that extends between the side surfaces of the fluid impermeable layer 102 (e.g., surface that are adjacent to the longitudinal edges of the opening 118). The traverse direction is perpendicular to the lateral direction and parallel to a direction that extends from the opening 118 to an opposing back surface of the fluid impermeable layer 102. In an embodiment, as shown, the extension 104 is positioned such that the width W is parallel to the lateral direction and the thickness t is parallel to the traverse direction. In such an embodiment, the width W controls how much pressure the gluteal cleft to the extension and, by extension, how securely the extension is positioned in the gluteal cleft. In other words, increasing the width W may cause the extension to be more securely positioned in the gluteal cleft. However, the individual may find positioning the extension such that the width W is parallel to the lateral direction to be uncomfortable. As such, in an embodiment, the individual may select and/or position the extension 104 such that the thickness t is parallel to the lateral direction and the width W is parallel to the traverse direction.

The extension 104 may be formed from any suitable material. In an embodiment, the extension 104 may be at least partially formed from a fluid impermeable material, such as silicone or neoprene. Forming the extension 104 from a fluid impermeable material may prevent or at least inhibit the extension 104 from receiving waste material present in the gluteal cleft. In an embodiment, the extension 104 may be at least partially formed from a porous or otherwise breathable material, such as a foam. In such an embodiment, the extension 104 may receive sweat or other bodily fluids (e.g., bodily fluids that leaked from the chamber 116) present in the gluteal cleft and allow air flow in the gluteal cleft. In an embodiment, the extension 104 may include a fluid impermeable material covered in a porous material (e.g., a disposable porous cover positioned over the fluid impermeable material) thereby allowing the extension 104 to exhibit the benefits of being formed from a fluid impermeable material and a fluid permeable material.

The extension 104 is reversibly attachable to the fluid impermeable layer 102. The extension 104 is reversibly attachable to the fluid impermeable layer 102 when the extension 104 may be attached and then detached from the fluid impermeable layer 102 substantially without damaging the fluid impermeable layer 102 and the extension 104. In an example, the extension 104 may be reversibly attachable to the fluid impermeable layer 102 when the extension 104 may be attached and detached from the fluid impermeable layer 102 on multiple occasions substantially without damaging the fluid impermeable layer 102 and the extension 104 and substantially without decreasing the strength of the attachment between the fluid impermeable layer 102 and the extension 104.

Reversibly attaching the extension 104 allows the individual using the fluid collection assembly 100 to determine when the fluid impermeable layer 102 and the extension 104 are attached together depending on the situation and the individual's preference. In an example, the individual may not prefer not to use the extension 104. In such an example, the individual may detach the extension 104 from the fluid impermeable layer 102 or leave the extension 104 detached from the fluid impermeable layer 102. In an example, the individual may only prefer to have the extension 104 attached to the fluid impermeable layer 102 when the individual is in at least one first position and may prefer to have the extension 104 detached from the fluid impermeable layer 102 when the individual is in at least one second position. As such, the ability of the fluid impermeable layer 102 and the extension 104 to be reversibly attached together allows the individual to attach the extension 104 to the fluid impermeable layer 102 when the individual is in the first position and remove the extension 104 when the individual is in the second position.

In an embodiment, as illustrated, the fluid impermeable layer 102 may include a first attachment device 110 at the distal end region 108 and the extension 104 may include a second attachment device 112. The first attachment device 110 and the second attachment device 112 may be configured to interact with each other in a manner that allows the first attachment device 110 and the second attachment device 112 to be reversibly attached together. The first and second attachment devices 110, 112 may include any attachment devices that allow the fluid impermeable layer 102 and the extension 104 to be reversibly attached together. It is noted that the distance d may be measured from the intersection between the first and second attachment devices 110, 112 when the first and second attachment devices 110, 112 are attached together.

In an embodiment, the first and second attachment devices 110, 112 are configured to be press-fitted together. In such an embodiment, at least one of the first and second attachment device 110, 112 includes a protrusion and the other of the first or second attachment device 110, 112 includes a recess that is configured to receive the protrusion. In the illustrated embodiment, the first attachment device 110 includes the recess and the second attachment device 112 includes the protrusion. At least a portion of the protrusion exhibits a lateral dimension that is equal to or slightly greater than a lateral dimension of at least a portion of the recess. As such, inserting the protrusion into the recess causes at least a portion of the protrusion to press against at least a portion of the recess. The friction between the protrusion and the recess may secure the protrusion in the recess thereby reversibly attaching the first and second attachment devices 110, 112 together. In an example, as illustrated, the protrusion may include a wider section and a narrowed section extending from the wider section to the rest of the attachment device and the recess may include a narrowed region and a wider region that is spaced further from an opening of the recess than the narrowed region. The wider section of the protrusion may exhibit a lateral dimension greater than a lateral dimension of the narrowed region of the recess and, thus, insertion of the wider section of the protrusion into the narrowed region of the recess may cause the protrusion to be press-fitted. However, insertion of the protrusion further into the recess may cause the wider section of the protrusion to be inserted into the wider region of the recess and the narrowed rejection of the recess may maintain the wider section of the protrusion in the wider region of the recess which, for simplicity, is referred to herein as a type of press-fitting. In an embodiment, as illustrated, the protrusion a generally spherical (e.g., generally semi-spherical) and the narrowed region exhibits a shape that is configured to receive the generally spherical protrusion (e.g., the narrowed region exhibits a generally spherical shape). In an embodiment, the protrusion exhibits a non-spherical shape (e.g., a generally conical shape, a generally semi-oval or elliptical shape, etc.) and the narrowed region exhibits a shape that is configured to receive the non-spherical shape of the protrusion (e.g., a shape that generally corresponds to the shape of the protrusion).

The first and second attachment devices 110, 112 of the fluid impermeable layer 102 and the extension 104 may be reversibly attached together using a technique other than press-fitting. In an example, one of the first attachment device 110 or the second attachment device 112 may include a magnet and the other of the first attachment device 110 or the second attachment device 112 may include an oppositely poled magnet or a magnetically-attracted material (e.g., iron, nickel, etc.). In an example, the first and second attachment devices 110, 112 may be configured to be threadedly attached together.

In an embodiment, only one of the fluid impermeable layer 102 or the extension 104 includes an attachment device. For example, only one of the fluid impermeable layer 102 or the extension 104 may include a suction cup or a plurality of nano-sized fibers (i.e., Gecko tape) that allows the fluid impermeable layer 102 and the extension to be reversibly attached together.

In an embodiment, the fluid collection assembly 100 may be provided with the fluid impermeable layer 102 and the extension 104 attached together (e.g., separately attached or integrally formed with each other). In such an embodiment, the individual may use the fluid collection assembly 100 without needing to attach the fluid impermeable layer 102 and the extension 104 together though the individual may decide to detach the fluid impermeable layer 102 from the extension 104 depending on the individual's preferences. In an embodiment, the fluid collection assembly 100 may be provided with the fluid impermeable layer 102 and the extension detached from each other. Depending on the individual's preference, the individual may attach the fluid impermeable layer 102 and the extension 104 together prior to using the fluid collection assembly 100. In an embodiment, the fluid collection assembly 100 may be provided with a plurality of extensions with one or none of the plurality of extensions reversibly attached to the fluid impermeable layer 102. In such an embodiment, at least some of the plurality of extensions may be different (e.g., exhibit different at least one of shapes, distances d, widths W, or thicknesses t) and the individual may select one of the plurality of extensions based on the individual's preference.

The individual may then reversibly attach the selected extension to the fluid impermeable layer 102.

The fluid impermeable layer 102 at least partially defines a chamber 116 (e.g., interior region) and an opening 118. For example, the interior surface(s) 120 of the fluid impermeable layer 102 at least partially defines the chamber 116 within the fluid collection assembly 100. The fluid impermeable layer 102 temporarily stores the bodily fluids in the chamber 116. The fluid impermeable layer 102 may be formed of any suitable fluid impermeable material(s), such as a fluid impermeable polymer (e.g., silicone, polypropylene, polyethylene, polyethylene terephthalate, neoprene, a polycarbonate, etc.), a metal film, natural rubber, another suitable material, any other fluid impermeable material disclosed herein, or combinations thereof. As such, the fluid impermeable layer 102 substantially prevents the bodily fluids from passing through the fluid impermeable layer 102. In an example, the fluid impermeable layer 102 may be air permeable and fluid impermeable. In such an example, the fluid impermeable layer 102 may be formed of a hydrophobic material that defines a plurality of pores. At least one or more portions of at least an outer surface 122 of the fluid impermeable layer 102 may be formed from a soft and/or smooth material, thereby reducing chaffing.

In some examples, the fluid impermeable layer 102 may be tubular (ignoring the opening), such as substantially cylindrical (as shown), oblong, prismatic, or flattened tubes. During use, the outer surface 122 of the fluid impermeable layer 102 may contact the individual. The fluid impermeable layer 102 may be sized and shaped to fit between the labia and/or the gluteal cleft between the legs of a female user.

The opening 118 provides an ingress route for bodily fluids to enter the chamber 116. The opening 118 may be defined by the fluid impermeable layer 102 such as by an inner edge of the fluid impermeable layer 102. For example, the opening 118 is formed in and extends through the fluid impermeable layer 102, from the outer surface 122 to the inner surface 120, thereby enabling bodily fluids to enter the chamber 116 from outside of the fluid collection assembly 100.

The opening 118 may be an elongated hole in the fluid impermeable layer 102. For example, the opening 118 may be defined as a cut-out in the fluid impermeable layer 102. The opening 118 may be located and shaped to be positioned adjacent to a female urethra. The opening 118 may have an elongated shape because the space between the legs of a female is relatively small when the legs of the female are closed, thereby only permitting the flow of the bodily fluids along a path that corresponds to the elongated shape of the opening 118 (e.g., longitudinally extending opening).

The fluid collection assembly 100 may be positioned proximate to the female urethral opening and the bodily fluids may enter the chamber 116 of the fluid collection assembly 100 via the opening 118. The fluid collection assembly 100 is configured to receive the bodily fluids into the chamber 116 via the opening 118. When in use, the opening 118 may have an elongated shape that extends from a first location below the urethral opening (e.g., at or near the anus or the vaginal opening) to a second location above the urethral opening (e.g., at or near the top of the vaginal opening or the pubic hair).

In some examples, the fluid impermeable layer 102 may define a fluid outlet 124 sized to receive the conduit 126. The at least one conduit 126 may be disposed in the chamber 116 via the fluid outlet 124. The fluid outlet 124 may be sized and shaped to form an at least substantially fluid tight seal against the conduit 126 or the at least one tube thereby substantially preventing the bodily fluids from escaping the chamber 116.

The fluid collection assembly 100 includes porous material 128 disposed in the chamber 116. The porous material 128 may cover at least a portion (e.g., all) of the opening 118. The porous material 128 may include a fluid permeable outer layer 130 (e.g., fluid permeable membrane) and a fluid permeable inner layer 132 (e.g., a fluid impermeable support). The porous material 128 is exposed to the environment outside of the chamber 116 through the opening 118. In an embodiment, the porous material 128 may be configured to wick any bodily fluids away from the opening 118, thereby preventing the bodily fluids from escaping the chamber 116. The permeable properties referred to herein may be wicking, capillary action, diffusion, or other similar properties or processes, and are referred to herein as "permeable" and/or "wicking." Such "wicking" and/or "permeable" properties may not include absorption of the bodily fluids into at least a portion of the porous material 128, such as not include adsorption of the bodily fluids into the fluid permeable inner layer 132. Put another way, substantially no absorption or solubility of the bodily fluids into the material may take place after the material is exposed to the bodily fluids and removed from the bodily fluids for a time. While no absorption or solubility is desired, the term "substantially no absorption" may allow for nominal amounts of absorption and/or solubility of the bodily fluids into the porous material 128 (e.g., absorbency), such as less than about 30 wt % of the dry weight of the porous material 128, less than about 20 wt %, less than about 10 wt %, less than about 7 wt %, less than about 5 wt %, less than about 3 wt %, less than about 2 wt %, less than about 1 wt %, or less than about 0.5 wt % of the dry weight of the porous material 128. The porous material 128 may also wick the bodily fluids generally towards an interior of the chamber 116, as discussed in more detail below. In an embodiment, the porous material 128 may include at least one absorbent or adsorbent material.

In an embodiment, at least a portion of the porous material 128 (e.g., one or more of the fluid permeable outer layer 130 or, more preferably, the fluid permeable inner layer 132) may be hydrophobic. The porous material 128 may be hydrophobic when the porous material 128 exhibits a contact angle with water (a major constituent of bodily fluids) that is greater than about 90°, such as in ranges of about 90° to about 120°, about 105° to about 135°, about 120° to about 150°, about 135° to about 175°, or about 150° to about 180°. The hydrophobicity of the porous material 128 may limit absorption, adsorption, and solubility of the bodily fluids in the porous material 128 thereby decreasing the amount of bodily fluids held in the porous material 128. In an embodiment, at least a portion of the porous material 128 is hydrophobic or hydrophilic. In an embodiment, the fluid permeable inner layer 132 is more hydrophobic (e.g., exhibits a larger contact angle with water) than the fluid permeable outer layer 130. The lower hydrophobicity of the fluid permeable outer layer 130 may help the porous material 128 receive the bodily fluids from the urethral opening while the hydrophobicity of the fluid permeable inner layer 132 limits the bodily fluids that are retained in the porous material 128.

In an embodiment, the porous material 128 may include the fluid permeable outer layer 130 disposed in the chamber 116. The fluid permeable outer layer 130 may cover at least a portion (e.g., all) of the opening 118. The fluid permeable outer layer 130 may be composed to wick the bodily fluids away from the opening 118, thereby preventing the bodily fluids from escaping the chamber 116.

In an embodiment, the fluid permeable outer layer 130 may include any material that may wick the bodily fluids. For example, the fluid permeable outer layer 130 may include fabric, such as a gauze (e.g., a silk, linen, or cotton gauze), another soft fabric, another smooth fabric, a non-woven material, or any of the other porous materials disclosed herein. Forming the fluid permeable outer layer 130 from gauze, soft fabric, and/or smooth fabric may reduce chaffing caused by the fluid collection assembly 100.

The fluid collection assembly 100 may include the fluid permeable inner layer 132 disposed in the chamber 116. The fluid permeable inner layer 132 is configured to inner layer the fluid permeable outer layer 130 since the fluid permeable outer layer 130 may be formed from a relatively foldable, flimsy, or otherwise easily deformable material. For example, the fluid permeable inner layer 132 may be positioned such that the fluid permeable outer layer 130 is disposed between the fluid permeable inner layer 132 and the fluid impermeable layer 102. As such, the fluid permeable inner layer 132 may inner layer and maintain the position of the fluid permeable outer layer 130. The fluid permeable inner layer 132 may include any material that may wick, absorb, adsorb, or otherwise allow fluid transport of the bodily fluids, such as any of the fluid permeable outer layer materials disclosed herein above. For example, the fluid permeable outer layer material(s) may be utilized in a more dense or rigid form than in the fluid permeable outer layer 130 when used as the fluid permeable inner layer 132. The fluid permeable inner layer 132 may be formed from any fluid permeable material that is less deformable than the fluid permeable outer layer 130. For example, the fluid permeable inner layer 132 may include a porous polymer (e.g., nylon, polyester, polyurethane, polyethylene, polypropylene, etc.) structure or an open cell foam, such as spun nylon fiber. In some examples, the fluid permeable inner layer 132 may include a nonwoven material. In some examples, the fluid permeable inner layer 132 may be formed from a natural material, such as cotton, wool, silk, or combinations thereof. In such examples, the material may have a coating to prevent or limit absorption of fluid into the material, such as a water repellent coating. In some examples, the fluid permeable inner layer 132 may be formed from fabric, felt, gauze, or combinations thereof.

In some examples, the fluid permeable outer layer 130 may be optional. For example, the porous material 128 may include only a fluid permeable layer that is substantially similar to the fluid permeable inner layer 132. In some examples, the fluid permeable inner layer 132 may be optionally omitted from the fluid collection assembly 100. For example, the porous material 128 may only include a single layer that is substantially similar to the fluid permeable outer layer 130. In an embodiment, the porous material 128 may include one or more additional fluid permeable layers instead of or in addition to the fluid permeable outer layer 130 and the fluid permeable inner layer 132.

The porous material 128 may at least substantially completely fill the portions of the chamber 116 that are not occupied by the conduit 126. In some examples, the porous material 128 may not substantially completely fill the portions of the chamber 116 that are not occupied by the conduit 126. In such an example, the fluid collection assembly 100 includes the reservoir 134 disposed in the chamber 116.

The reservoir 134 is a substantially unoccupied portion of the chamber 116. The reservoir 134 may be defined between the fluid impermeable layer 102 and one or both of the fluid permeable outer layer 130 and fluid permeable inner layer 132. The bodily fluids that are in the chamber 116 may flow through the fluid permeable outer layer 130 and/or fluid permeable inner layer 132 to the reservoir 134. The reservoir 134 may retain of the bodily fluids therein.

The bodily fluids that are in the chamber 116 may flow through the fluid permeable outer layer 130 and/or fluid permeable inner layer 132 to the reservoir 134. The fluid impermeable layer 102 may retain the bodily fluids in the reservoir 134. While depicted in the distal end region 108, the reservoir 134 may be located in any portion of the chamber 116 such as the proximal end region 106. The reservoir 134 may be located in a portion of the chamber 116 that is designed to be located in a gravimetrically low point of the fluid collection assembly when the fluid collection assembly is worn.

In some examples (not shown), the fluid collection assembly 100 may include multiple reservoirs, such as a first reservoir that is located at the portion of the chamber 116 closest to the inlet of the conduit 126 (e.g., distal end region 108) and a second reservoir that is located at the portion of the of the chamber 116 that is at or near proximal end region 106). In another example, the fluid permeable inner layer 132 is spaced from at least a portion of the conduit 126, and the reservoir 134 may be the space between the fluid permeable inner layer 132 and the conduit 126.

The conduit 126 may be at least partially disposed in the chamber 116. The conduit 126 may be used to remove the bodily fluids from the chamber 116. The conduit 126 includes at least one wall defining an inlet 136, an outlet (not shown) downstream from the inlet 136, and a passageway 138. The outlet of the conduit 126 may be operably coupled to a vacuum source, such as a vacuum pump for withdrawing fluid from the chamber 116 through the conduit 126. For example, the conduit 126 may extend into the fluid impermeable layer 102 from the proximal end region 106 and may extend to the distal end region 108 to a point proximate to the reservoir 134 therein such that the inlet 136 is in fluid communication with the reservoir 134. The conduit 126 fluidly couples the chamber 116 with the fluid storage container (not shown) or the vacuum source (not shown).

The conduit 126 may extend through a bore in the porous material 128. In an embodiment, the conduit 126 extends from the fluid outlet 124, through the bore, to a location that is proximate to the reservoir 134. In such an embodiment, the inlet 136 may not extend into the reservoir 134 and, instead, the inlet 136 may be disposed within the porous material 128 (fluid permeable outer layer 130 and/or fluid permeable inner layer 132) or at a terminal end thereof. For example, an end of the conduit 126 may be coextensive with or recessed within the fluid permeable outer layer 130 and/or fluid permeable inner layer 132. In an embodiment, the conduit 126 is at least partially disposed in the reservoir 134 and the inlet 136 may be extended into or be positioned in the reservoir 134. The bodily fluids collected in the fluid collection assembly 100 may be removed from the chamber 116 via the conduit 126.

Locating the inlet 136 at or near a location expected to be the gravimetrically low point of the chamber 116 when worn by a individual enables the conduit 126 to receive more of the bodily fluids than if inlet 136 was located elsewhere and reduce the likelihood of pooling (e.g., pooling of the bodily fluids may cause microbe growth and foul odors). For instance, the bodily fluids in the fluid permeable outer layer 130 and the fluid permeable inner layer 132 may flow in any direction due to capillary forces. However, the bodily fluids may exhibit a preference to flow in the direction of gravity, especially when at least a portion of the fluid permeable outer layer 130 and/or the fluid permeable inner layer 132 is saturated with the bodily fluids. Accordingly, one or more of the inlet 136 or the reservoir 134 may be located in the fluid collection assembly 100 in a position expected to be the gravimetrically low point in the fluid collection assembly 100 when worn by a individual, such as the distal end region 108.

The inlet 136 and the outlet of the conduit 126 are configured to fluidly couple (e.g., directly or indirectly) the vacuum source (not shown) to the chamber 116 (e.g., the reservoir 134). As the vacuum source (FIG. 4) applies a vacuum/suction in the conduit 126, the bodily fluids in the chamber 116 (e.g., at the distal end region 108 such as in the reservoir 134) may be drawn into the inlet 136 and out of the fluid collection assembly 100 via the conduit 126. In some examples, the conduit 126 may be frosted or opaque (e.g., black) to obscure visibility of the bodily fluids therein.

As previously discussed, the conduit 126 may be configured to be at least insertable into the chamber 116. In an example, the conduit 126 may be positioned in the chamber 116 such that a terminal end of the conduit 126 is spaced from the fluid impermeable layer 702 or other components of the fluid collection assembly 100 that may at least partially obstruct or block the inlet 136. Further, the inlet 136 of the conduit 126 may be offset relative to a terminal end of the porous material 128 such that the inlet 136 is closer to the proximal end region 106 of the fluid collection assembly 100 than the terminal end of the porous material 128. Offsetting the inlet 136 in such a manner relative to the terminal end of the porous material 128 allows the inlet 136 to receive bodily fluids directly from the porous material 128 and, due to hydrogen bonding, pulls more bodily fluids from the porous material 128 into the conduit 126.

Further examples of fluid collection assemblies are disclosed in U.S. patent application Ser. No. 15/612,325 filed on Jun. 2, 2017, U.S. patent application Ser. No. 15/260,103 filed on Sep. 8, 2016, and U.S. Pat. No. 10,390,989 filed on Sep. 8, 2016, the disclosure of each of which is incorporated herein, in its entirety, by this reference.

Figure 2A:
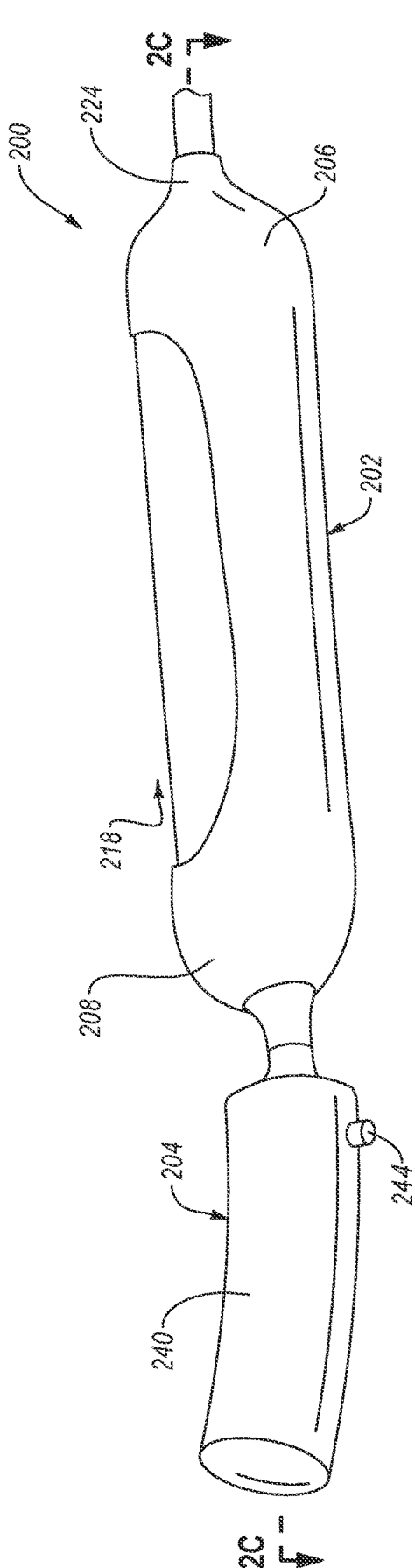
FIGS. 2A and 2B are isometric views of a fluid collection assembly that includes a fluid impermeable layer and an extension reversibly inflated and reversibly deflated, respectively, according to an embodiment.
Figure 2B:
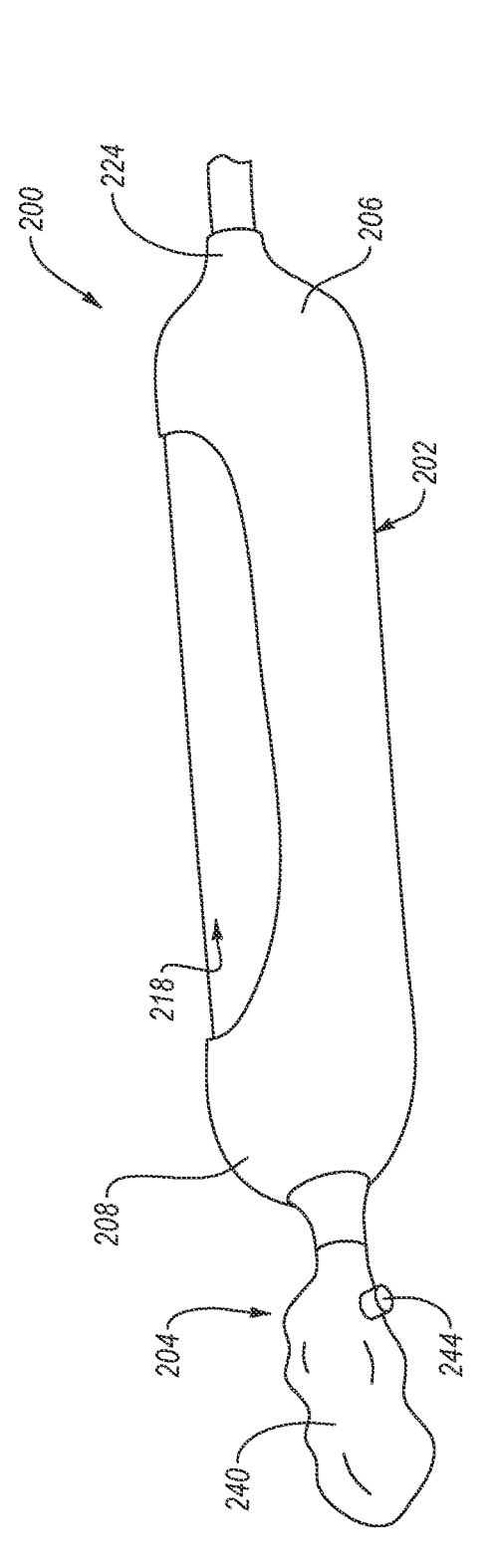
Figure 2C:
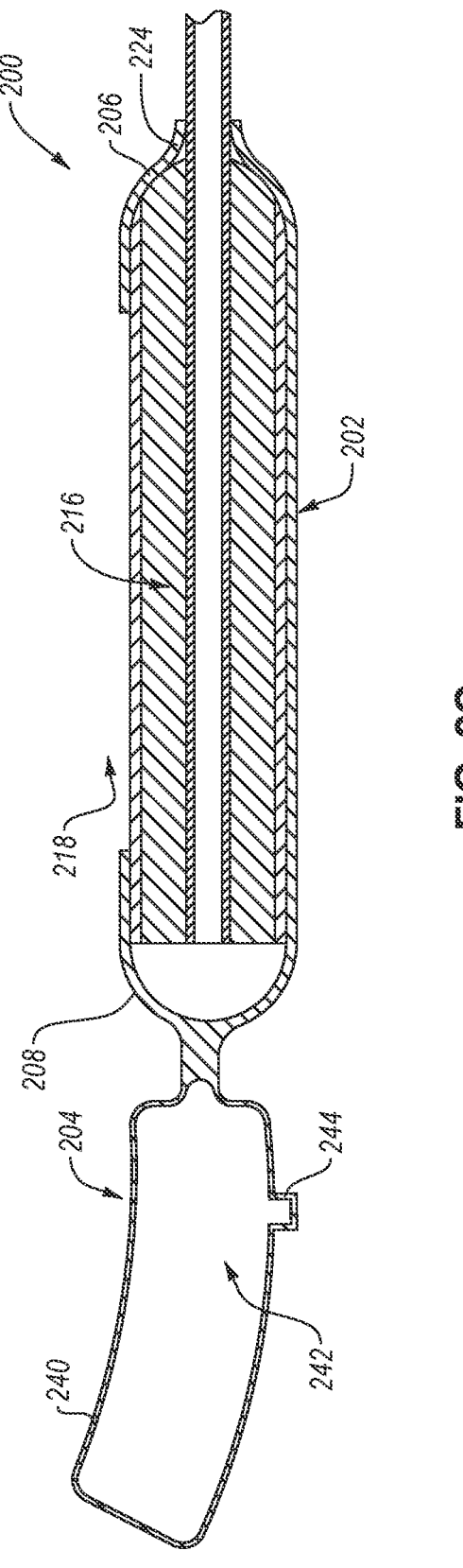
FIG. 2C is a cross-sectional schematic of the fluid collection assembly illustrated in FIG. 2A.

The extensions of the fluid collection assemblies disclosed herein may be inflatable and deflatable instead of or in addition to be reversibly attachable to the fluid impermeable layer. For example, FIGS. 2A and 2B are isometric views of a fluid collection assembly 200 that includes a fluid impermeable layer 202 and an extension 204 reversibly attached to and reversibly detached from the fluid impermeable layer 202, respectively, according to an embodiment. FIG. 2C is a cross-sectional schematic of the fluid collection assembly 200 illustrated in FIG. 2A. Except as otherwise disclosed herein, the fluid collection assembly 200 is the same or substantially similar to any of the fluid collection assemblies disclosed herein. For example, the fluid collection assembly 200 includes a fluid impermeable layer 202 including a proximal end region 206 and a distal end region 208. The fluid impermeable layer 202 may also define at least a chamber 216, at least one opening 218, and a fluid outlet 224. The fluid collection assembly 200 may also include at least one porous material 228 disposed in the chamber 216. The extension 204 may extend from or near the distal end region 208 of the fluid impermeable layer 202. The extension 204 may be configured to fit in the gluteal cleft of an individual.

The extension 204 includes at least one bladder 240 defining an interior region 242 and at least one valve 244 in fluid communication with the interior region 242. The valve 244 is configured to selectively permit flow of an inflation fluid into and/or out the interior region 242. For example, the valve 244 may allow an inflation fluid to enter the interior region 242 when it is desirable inflate the bladder 240 and remove the inflation fluid from the interior region 242 when it is desirable to deflate the bladder 240.

Disposing or removing the inflation fluids into and from the interior region 242 changes the state of the bladder 240. The bladder 240 may exhibit at least a first state (shown in FIG. 2A) and a second state (shown in FIG. 2B). The amount (volume or weight) of inflation fluids present in the interior region 242 is greater when the bladder 240 is in the first state than when the bladder 240 is in the second state. In an example, as shown in FIG. 2A, the bladder 240 is in the first state when the bladder 240 is in an at least partially inflated state. In an example, as shown in FIG. 2B, the bladder 240 is in the second state when the bladder 240 is in a deflated state (e.g., there are no or substantially no fluids in the interior region 242). However, it is noted that the bladder 240 may be in the second state when some inflation fluids are present in the interior region 242. The bladder 240 may exhibit one or more additional states (e.g., third state, fourth state, and so forth) besides the first and second states discussed above.

Switching the bladder 240 from the first state to the second state (or any of the other states thereof) changes the shape of the extension 204 and/or increase a distance that a portion of the extension 204 extends from the fluid impermeable layer 202. For example, the volume of the bladder 240 may be greater when the bladder 240 is in the first state than when the bladder 240 is in the second state. As such, when the bladder 240 is in the first state, the bladder 240 may at least one of extend a greater distance from the fluid impermeable layer 202 than, exhibit a width and/or thickness that is greater than, or exhibit a firmness that is greater than the bladder 240 in the second state. As such, an individual may inflate the extension 204 (e.g., switch the bladder 240 from the second state to the first state) and/or deflate the extension 204 (e.g., switch the bladder 240 from the first state to the second state) depending on the individual's preference or circumstance. In an example, the individual may inflate or deflate the extension 204 based on the individual's preference for at least one of the distance that the extension 204 extends from the fluid impermeable layer 202, the width and/or thickness of the extension 204, or the firmness of the extension 204. In an example, the individual may inflate and/or deflate the extension 204 depending on the position of the individual. For instance, the individual may desire the extension 204 to exhibit one or more characteristics (e.g., at least one of extend from the fluid impermeable layer 202 a certain distance, exhibit a width and/or thickness of the extension 204, or exhibit a firmness) that are different when the individual is in the first position (e.g., lying down) and in a second position (e.g., sitting up).

The bladder 240 is formed from a material is substantially impermeable to the inflation fluid (e.g., substantially impermeable to a gas and/or a liquid) which allows the bladder 240 to retain the inflation fluids without embarrassing leaks. The bladder 240 may also be formed from a flexible material. The flexible material of the bladder 240 allows the bladder 240 and, by extension, the fluid collection assembly 200 to at least one of increase in size or change a shape thereof. For example, the flexible material of the bladder 240 allow the interior region 242 to increase a volume thereof when the interior region 242 receives an inflation fluid and decrease a volume thereof when inflation fluids are removed from the interior region 242. Examples of materials that may form the bladder 240 include silicone, rubber, latex, polychloroprene, nylon fabric, polypropylene, polyvinyl chloride, nitrile rubber, other suitable polymers, a metal foil, a composite, or combinations thereof. In an embodiment, the bladder 240 are configured to stretch (e.g., elastically or plastically stretch) so the bladder 240 remain taut when the bladder 240 is at least partially inflated. In an embodiment, the bladder 240 forms a plurality of wrinkles when the bladder 240 is at least partially deflated and adding inflation fluid into the interior region 242 decreases the wrinkles, similar to an accordion.

The valve 244 may include any suitable valve configured to allow for the controllable addition and remove of inflation fluids from the interior region 242. In an embodiment, the valve 244 is a luer valve and includes a male-tapper fitting or a female-taper fitting. In an embodiment, the valve 244 includes a fluid impermeable membrane with a slit or opening formed. The slit or opening of the fluid impermeable membrane remains substantially closed when no external load is applied thereto but opens when an external load is applied thereto (e.g., an external load caused by pressing a syringe against the fluid impermeable membrane). In an embodiment, the valve 244 may include a mechanical valve, such as a ball valve, a butterfly valve, or any other suitable mechanical valve. The mechanical valve may be manually operated or controlled using a computer. In an embodiment, the valve 244 may include a check valve to limit leaks from the bladder 240 and to make the fluid collection assembly 200 easier to use. In such an embodiment, the valve 244 may only add or remove (but not both) inflation fluid from the interior region 242 and, as such, the fluid collection assembly 200 is configured for single use.

In an embodiment, the valve 244 extends from a portion of the extension 204 that is adjacent or proximate to the fluid impermeable layer 202 to prevent the valve 244 from being positioned in the gluteal cleft since positioning the valve 244 in the gluteal cleft may cause discomfort and pain.

In an embodiment, the extension 204 may only include a single a single bladder 240 and/or a single valve 244. In an embodiment, the fluid collection assembly 200 may include a plurality of bladders 240 and/or a plurality of valves 244. For example, the extension 204 may include a plurality of bladders 240 attached to each other. The plurality of bladders 240 may allow the individual to have greater control on the characteristics of the extension 204 than if the extension 204 only included a single bladder 240.

The at least one inflation fluid added or removed from the interior region 242 may include any suitable fluid, such as any suitable liquid or any suitable gas. In an embodiment, the inflation fluids are formed from a generally regarded as safe ("GRAS") material. Forming the inflation fluids from a GRAS materials may decrease health risks caused by inadvertently exposing the individual to the inflation fluids. Examples of GRAS materials that may form the inflation fluids includes water, saline solution, alcohol solution, atmospheric air, nitrogen, or combinations thereof.

Figures 3A, 3B, 3C:
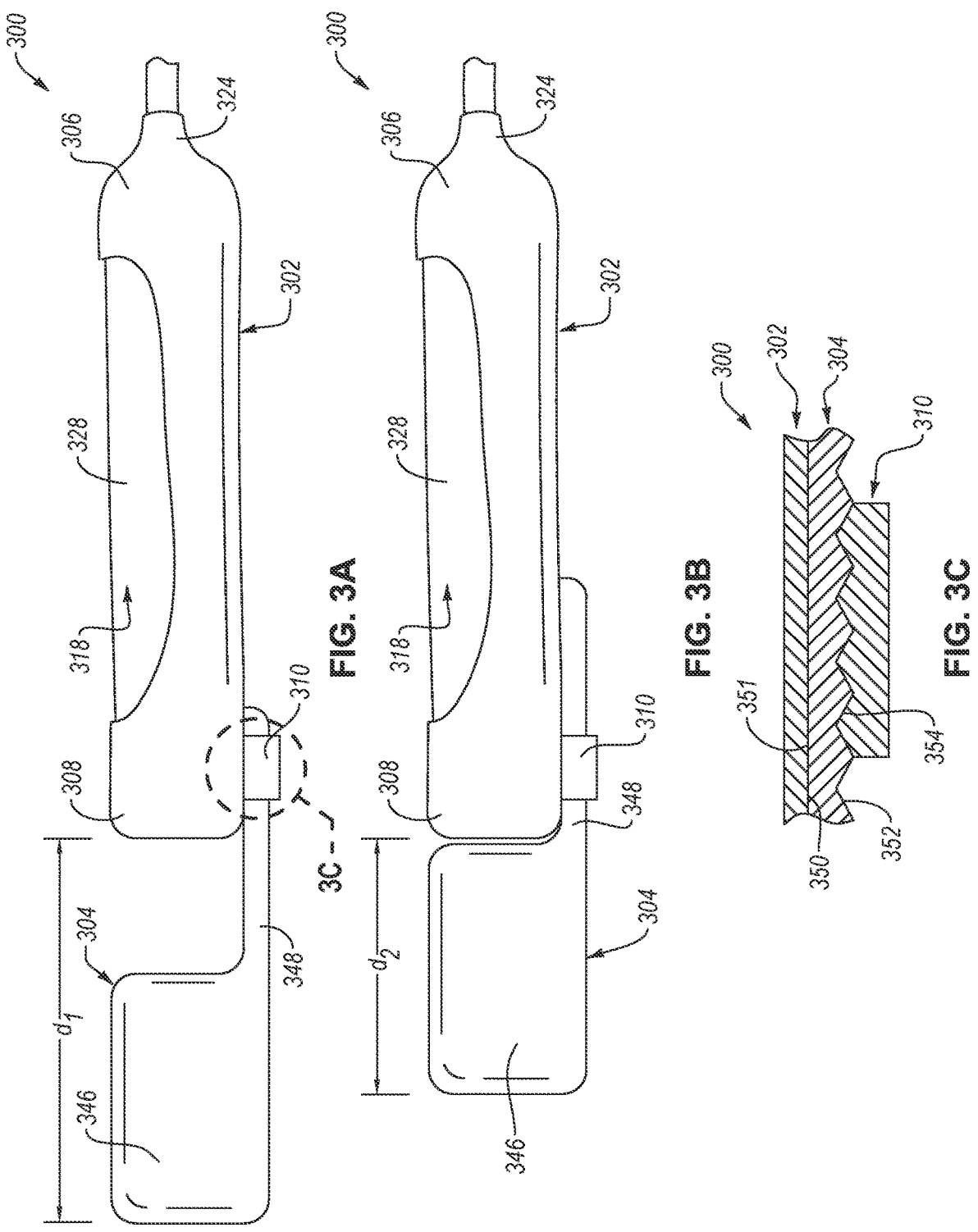
FIGS. 3A and 3B are isometric views of a fluid collection assembly including an extension extending different distances from the fluid impermeable layer, according to an embodiment.
FIG. 3C is an enlarged cross-sectional view of the fluid collection assembly taken from circle 3C illustrated in FIG. 3A illustrating how the extension may move relative to the fluid impermeable layer, according to an embodiment.

As previously discussed, the extension of the fluid collection assemblies disclosed herein may be configured to change a distance that the extension extends from the fluid collection assembly instead of or in addition to at least one of reversibly attaching the extension to the fluid impermeable layer or inflating and/or deflating the extension. For example, FIGS. 3A and 3B are isometric views of a fluid collection assembly 300 including an extension 304 extending different distances from the fluid impermeable layer 302, according to an embodiment. Except as otherwise disclosed herein, the fluid collection assembly 300 is the same or substantially similar to any of the fluid collection assemblies disclosed herein. For example, the fluid collection assembly 300 includes a fluid impermeable layer 302 including a proximal end region 306 and a distal end region 308. The fluid impermeable layer 302 may also define at least a chamber (not shown, obscured), at least one opening 318, and a fluid outlet 324. The fluid collection assembly 300 also includes at least one porous material 328 disposed in the chamber. The extension 304 may extend from or near the distal end region 308 of the fluid impermeable layer 302. The extension 304 may be configured to fit in the gluteal cleft of an individual.++

As shown in FIGS. 3A and 3B, the extension 304 may be configured to move relative to the fluid impermeable layer 302 such that a distance that the extension 304 extends from the fluid impermeable layer 302 may change. For example, the extension 304 may be configured to extend a first distance $d_1$ (FIG. 3A) and a second distance $d_2$ (FIG. 3B) from the fluid impermeable layer 302 that is less than the first distance $d_1$. The extension 304 may, optionally, be configured to extend one or more additional distances that are at least one of greater than the first distance $d_1$, between the first distance $d_1$ and the second distance $d_2$, or less than the second distance $d_2$. Allowing the extension 304 to move relative to the fluid impermeable layer 302 allows the individual to change the distance that the extension 304 extends from the fluid impermeable layer 302 depending on the individual's preference or the particular situations. In an example, the individual may change the distance that the extension 304 extends from the fluid impermeable layer 302 depending on what distance the individual finds most comfortable. In an example, the individual may prefer the extension 304 to extend from the fluid impermeable layer 302 by the first distance $d_1$ when the individual is in a first position (e.g., laying down) and the second distance de when the individual is in a second position (e.g., sitting up). As such, the individual may move the extension 304 between the first distance $d_1$ and the second distance $d_2$ when the individual switches between the first and second positions.

The first distance $d_1$ may be selected to be about 1 cm or greater, about 2 cm or greater, about 3 cm or greater, about 5 cm or greater, about 7.5 cm or greater, about 10 cm or greater, about 12.5 cm or greater, about 15 cm or greater, about 17.5 cm or greater, about 20 cm or greater, about 22.5 cm or greater, about 25 cm or greater, or in ranges of about 1 cm to about 3 cm, about 2 cm to about 5 cm, about 3 cm to about 7.5 cm, about 5 cm to about 10 cm, about 7.5 cm to about 12.5 cm, about 10 cm to about 15 cm, about 12.5 cm to about 17.5 cm, about 15 cm to about 20 cm, about 17.5 cm to about 22.5 cm, or about 20 cm to about 25 cm. The second distance $d_2$ may be selected to be less than the first distance $d_1$. The second distance $d_2$ may be selected to be 0 cm or greater, about 0.25 cm or greater, about 0.5 cm or greater, about 0.75 cm or greater, about 1 cm or greater, about 2 cm or greater, about 3 cm or greater, about 5 cm or greater, about 7.5 cm or greater, about 10 cm or greater, about 12.5 cm or greater, about 15 cm or greater, about 17.5 cm or greater, about 20 cm or greater, about 22.5 cm or greater, or in ranges of 0 cm to about 0.5 cm, about 0.25 cm to about 0.75 cm, about 0.5 cm to about 1 cm, about 0.75 cm to about 2 cm, about 1 cm to about 3 cm, about 2 cm to about 5 cm, about 3 cm to about 7.5 cm, about 5 cm to about 10 cm, about 7.5 cm to about 12.5 cm, about 10 cm to about 15 cm, about 12.5 cm to about 17.5 cm, or about 15 cm to about 20 cm. The first and second distances $d_1$ and $d_2$ may be selected based on the maximum and minimum distances that the extension 304 may move relative to the fluid impermeable layer 302 and the individual's preferences.

The extension 304 may be secured to the fluid impermeable layer 302 using an attachment device 310. The attachment device 310 does not rigidly attach the extension 304 to the fluid impermeable layer 302 which allows the extension 304 to move relative to the fluid impermeable layer 302. In an embodiment, as illustrated, only a portion of the extension 304 may interact with the attachment device 310 to secure the extension 304 to the fluid impermeable layer 302. In such an embodiment, for example, the extension 304 may include a first portion 346 and a second portion 348. The first portion 346 may be configured to be positioned between the gluteal cleft of the individual and the second portion 348 may be configured to interact with the attachment device 310 to secure the extension 304 to the fluid impermeable layer 302. The first portion 346 may exhibit a width or thickness that is greater than the second portion 348 which prevents the first portion 346 from being positioned within the attachment device 310. It is noted that the first portion 346 may limit the second distance de and prevent the second distance de from being zero or less than zero, as shown in FIG. 3B. The larger width of the first portion 346 may increase the surface area of the buttocks of the individual that the extension 304 contacts which allows the extension 304 to better secure the fluid collection assembly 300 to the gluteal cleft. Meanwhile, the smaller width of the second portion 348 decreases the size of the attachment device 310 needed to secure the extension 304 to the fluid impermeable layer 302 thereby decreasing any discomfort the attachment device 310 may cause the individual. In an embodiment, all of the extension 304 may be configured to interact with the attachment device 310.

The attachment device 310 may secure the extension 304 to the fluid impermeable layer 302 and allow the extension 304 to move relative to the fluid impermeable layer 302 using any suitable technique. FIG. 3C is an enlarged cross-sectional view of the fluid collection assembly 300 taken from circle 3C illustrated in FIG. 3A illustrating how the extension 304 may move relative to the fluid impermeable layer 302, according to an embodiment. The extension 304 may be positioned between the fluid impermeable layer 302 and the attachment device 310. The extension 304 may include a first surface 350 and a second surface 352. The first surface 350 may be positioned closer to (e.g., abuts) an outer surface 322 the fluid impermeable layer 302 (e.g., a back surface of the fluid impermeable layer 302 that is opposite the opening 318) than the second surface 352. The second surface 352 may be adjacent to (e.g. abuts) an inner surface 354 of the attachment device 310. The second surface 352 of the extension 304 and the inner surface 354 of the attachment device 310 may include one or more ridges and valleys formed therein. The ridges and valleys of the second surface 352 and the inner surface 354 may correspond to each other such that the ridges of the second surface 352 may be disposed in the valleys of the inner surface 354 and the ridges of the inner surface 354 may be disposed in the valleys of the second surface 352. The ridges and valleys of the second surface 352 and the inner surface 354 maintain the position of the extension 304 relative to the fluid impermeable layer 302 unless a sufficiently large force is applied to the extension 304. In other words, the sufficiently large force applied to the extension 304 allows the extension 304 to move relative to the fluid impermeable layer 302.

It is noted that the embodiment illustrated in FIG. 3C is merely one embodiment that may be used to secure the extension 304 to the fluid impermeable layer 302 that allows the extension 304 to move relative to the fluid impermeable layer 302. In another embodiment, the extension 304 may be positioned between the attachment device 310 and the fluid impermeable layer 302 as illustrated in FIG. 3C. However, in such an embodiment, the first surface 350 of the extension 304 and the outer surface 322 of the fluid impermeable layer 302 includes the ridges and valleys formed therein instead of or in addition to the second surface 352 of the extension 304 and the inner surface 354 of the attachment device 310. In another embodiment, the extension 304 may be positioned between the attachment device 310 and the fluid impermeable layer 302 as illustrated in FIG. 3C. However, in such an embodiment, none of the surfaces of the fluid impermeable layer 302, the extension 304, or the attachment device 310 includes ridges and valleys formed therein. Instead, the friction between the surfaces of the fluid impermeable layer 302, the extension 304, and the attachment device 310 may help maintain the position of the extension 304 relative to the fluid impermeable layer 302. In another embodiment, the attachment device 310 includes a layer between the extension 304 and the fluid impermeable layer 302. In another embodiment, at least two of the fluid impermeable layer 302, the extension 304, or the attachment device 310 are configured as a rack and pinion. In such an embodiment, at least one of the fluid impermeable layer 302, the extension 304, or the attachment device 310 includes a rack and at least one of the fluid impermeable layer 302, the extension 304, or the attachment device 310 includes a pinion that is configured to engage the rack. In another embodiment, the attachment device 310 may be moveable relative to the fluid impermeable layer 302 such that the extension 304 cannot move when the attachment device 310 is positioned relatively close to the fluid impermeable layer 302 and the extension 304 can move when the attachment device 310 is positioned relatively far from the fluid impermeable layer 302 (e.g., the attachment device 310 is a clamp). In an embodiment, fluid impermeable layer 302 and the extension 304 include one or more snaps and the position of the extension 304 relative to the fluid impermeable layer 302 depends on which snap(s) of the fluid impermeable layer 302 are attached to which snap(s) of the extension 304. In an embodiment, the fluid impermeable layer 302 and the extension 304 are attached together using Velcro and the position of the extension 304 relative to the fluid impermeable layer 302 depends on which portions of the Velcro of the fluid impermeable layer 302 are attached to the Velcro of the extension 304.

Figure 4:
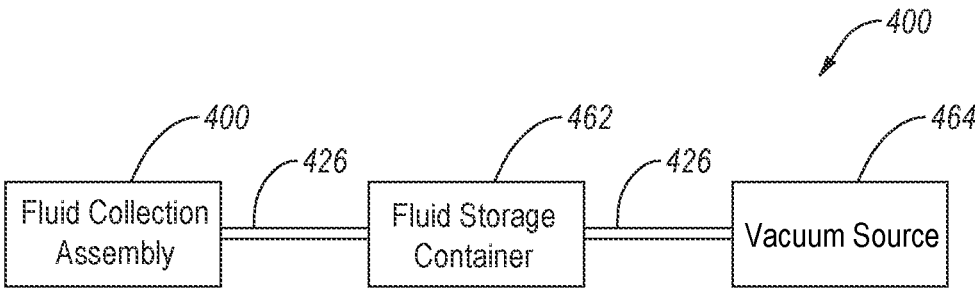
FIG. 4 is a block diagram of a fluid collection system for fluid collection, according to an embodiment.

FIG. 4 is a block diagram of a fluid collection system 460 for fluid collection, according to an embodiment. The fluid collection system 460 includes a fluid collection assembly 400, a fluid storage container 462, and a vacuum source 464. The fluid collection assembly 400 may be the same or substantially similar to any of the fluid collection assemblies disclosed herein. The fluid collection assembly 400, the fluid storage container 462, and the vacuum source 464 may be fluidly coupled to each other via one or more conduits 426. For example, fluid collection assembly 400 may be operably coupled to one or more of the fluid storage container 462 or the vacuum source 464 via the conduit 426. The bodily fluids collected in the fluid collection assembly 400 may be removed from the fluid collection assembly 400 via the conduit 426 which protrudes into the fluid collection assembly 400. For example, an inlet of the conduit 426 may extend into the fluid collection assembly 400, such as to a reservoir therein. The outlet of the conduit 426 may extend into the fluid collection assembly 400 or the vacuum source 464. Suction force may be introduced into the chamber of the fluid collection assembly 400 via the inlet of the conduit 426 responsive to suction (e.g., vacuum) force applied at the outlet of the conduit 426.

The suction force may be applied to the outlet of the conduit 426 by the vacuum source 464 either directly or indirectly. The suction force may be applied indirectly via the fluid storage container 462. For example, the outlet of the conduit 426 may be disposed within the fluid storage container 462 and an additional conduit 426 may extend from the fluid storage container 462 to the vacuum source 464. Accordingly, the vacuum source 464 may apply suction to the fluid collection assembly 400 via the fluid storage container 462. The suction force may be applied directly via the vacuum source 464. For example, the outlet of the conduit 426 may be disposed within the vacuum source 464. An additional conduit 426 may extend from the vacuum source 464 to a point outside of the fluid collection assembly 400, such as to the fluid storage container 462. In such examples, the vacuum source 464 may be disposed between the fluid collection assembly 400 and the fluid storage container 462.

The fluid storage container 462 is sized and shaped to retain bodily fluids therein. The fluid storage container 462 may include a bag (e.g., drainage bag), a bottle or cup (e.g., collection jar), or any other enclosed container for storing bodily fluids such as urine. In some examples, the conduit 426 may extend from the fluid collection assembly 400 and attach to the fluid storage container 462 at a first point therein. An additional conduit 426 may attach to the fluid storage container 462 at a second point thereon and may extend and attach to the vacuum source 464. Accordingly, a vacuum (e.g., suction) may be drawn through fluid collection assembly 400 via the fluid storage container 462. Bodily fluids, such as urine, may be drained from the fluid collection assembly 400 using the vacuum source 464.

The vacuum source 464 may include one or more of a manual vacuum pump, and electric vacuum pump, a diaphragm pump, a centrifugal pump, a displacement pump, a magnetically driven pump, a peristaltic pump, or any pump configured to produce a vacuum. The vacuum source 464 may provide a vacuum or suction to remove bodily fluids from the fluid collection assembly 400. In some examples, the vacuum source 464 may be powered by one or more of a power cord (e.g., connected to a power socket), one or more batteries, or even manual power (e.g., a hand operated vacuum pump). In some examples, the vacuum source 464 may be sized and shaped to fit outside of, on, or within the fluid collection assembly 400. For example, the vacuum source 464 may include one or more miniaturized pumps or one or more micro pumps. The vacuum sources 464 disclosed herein may include one or more of a switch, a button, a plug, a remote, or any other device suitable to activate the vacuum source 464.

While various aspects and embodiments have been disclosed herein, other aspects and embodiments are contemplated. The various aspects and embodiments disclosed herein are for purposes of illustration and are not intended to be limiting.

Terms of degree (e.g., "about," "substantially," "generally," etc.) indicate structurally or functionally insignificant variations. In an example, when the term of degree is included with a term indicating quantity, the term of degree is interpreted to mean±10%, ±5%, or ±2% of the term indicating quantity. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

What is claimed is:

1. A fluid collection assembly, comprising:
   a fluid impermeable layer including a proximal end region and a distal end region spaced from the proximal end region; the fluid impermeable layer defining at least a chamber, at least one opening, and a fluid outlet;
   at least one porous material disposed in the chamber; and
   an extension extending from or near the distal end region, the extension configured to be positioned in a gluteal cleft on an individual, the extension at least one of:
   reversibly attachable to the fluid impermeable layer;
   inflatable; or
   configured to change a distance that the extension extends from the distal end region of the fluid impermeable layer.

2. The fluid collection assembly of claim 1, wherein the extension is reversibly attachable to the fluid impermeable layer.

3. The fluid collection assembly of claim 2, wherein the fluid impermeable layer includes a first attachment device and the extension includes a second attachment device, the first attachment device and the second attachment device configured to be reversibly attached together.

4. The fluid collection assembly of claim 3, wherein one of the first attachment device or the second attachment device includes a protrusion and the other of the first attachment device or the second attachment device includes a recess configured to receive the protrusion.

5. The fluid collection assembly of claim 1, wherein the extension is inflatable.

6. The fluid collection assembly of claim 5, wherein the extension includes at least one bladder defining an interior region and at least one valve that allows for at least one inflation fluid to be disposed in or removed from the interior region.

7. The fluid collection assembly of claim 1, wherein the extension is configured to change a distance that the extension extends from the distal end region of the fluid impermeable layer.

8. The fluid collection assembly of claim 7, further comprising an attachment device, the extension positioned between the attachment device and a portion of the fluid impermeable layer or within the attachment device, the extension including a surface that abuts an interior surface of the attachment device, the surface of the extension of the interior surface of the attachment device including a plurality of ridges and valleys.

9. The fluid collection assembly of claim 1, wherein the extension extends a distance from the distal end region of the fluid impermeable layer that is 5 cm to 20 cm.

10. The fluid collection assembly of claim 1, wherein the extension exhibits a flat shape.

11. The fluid collection assembly of claim 1, wherein the extension exhibits a cylindrical or rounded shape.

12. The fluid collection assembly of claim 1, wherein the extension is curved.

13. The fluid collection assembly of claim 1, wherein the fluid outlet is at the proximal end region.

14. A fluid collection system, comprising:
    a fluid collection assembly including:
    a fluid impermeable layer including a proximal end region and a distal end region spaced from the proximal end region; the fluid impermeable layer defining at least a chamber, at least one opening, and a fluid outlet;

at least one porous material disposed in the chamber; and an extension extending from or near the distal end region, the extension configured to be positioned in a gluteal cleft on an individual, the extension at least one of:

reversibly attachable to the fluid impermeable layer;

inflatable; or configured to change a distance that the extension extends from the distal end region of the fluid impermeable layer;

a fluid storage container; and a vacuum source;

wherein the chamber of the fluid collection assembly is in fluid communication with the fluid storage container and the vacuum source via one or more conduits.

15. A method of using a fluid collection assembly, the method comprising:

positioning an opening of a fluid collection assembly adjacent to a urethral opening of an individual, the fluid collection assembly including:

a fluid impermeable layer including a proximal end region and a distal end region spaced from the proximal end region; the fluid impermeable layer defining at least a chamber, at least one opening, and a fluid outlet;

at least one porous material disposed in the chamber; and positioning an extension of the fluid collection assembly in a gluteal cleft of the individual, the extension extending from or near the distal end region of the fluid impermeable layer, the extension at least one of:

reversibly attachable to the fluid impermeable layer;

inflatable; or configured to change a distance that the extension extends from the distal end region of the fluid impermeable layer.

16. The method of claim 15, further comprising, when the individual changes positions, at least one of:

detaching the extension from the fluid impermeable layer;

deflating the extension; or decreasing a distance that the extension extends from the distal end region of the fluid impermeable layer.

17. The method of claim 15, further comprising, when the individual changes positions, at least one of:

attaching the extension to the fluid impermeable layer;

inflating the extension; or increasing a distance that the extension extends from the distal end region of the fluid impermeable layer.

18. The method of claim 15, further comprising attaching or detaching the extension from the fluid impermeable layer.

19. The method of claim 15, further comprising inflating or deflating the extension.

20. The method of claim 15, further comprising changing a distance that the extension extends from the distal end region of the fluid impermeable layer.

* * * * *